United States Patent
Hall et al.

(10) Patent No.: US 11,083,714 B2
(45) Date of Patent: Aug. 10, 2021

(54) SELECTIVE ANTI-CANCER AGENT EFFECTIVE FOR PREVENTION AND TREATMENT

(71) Applicant: Molecular International Research, Inc., New York, NY (US)

(72) Inventors: John L. Hall, New York, NY (US); Sylvie P. Beljanski, New York, NY (US)

(73) Assignee: Molecular International Research, Inc., New York, NY (US)

( * ) Notice: Subject to any disclaimer, the term of this patent is extended or adjusted under 35 U.S.C. 154(b) by 0 days.

(21) Appl. No.: 17/042,786

(22) PCT Filed: Apr. 1, 2019

(86) PCT No.: PCT/US2019/025234
§ 371 (c)(1),
(2) Date: Sep. 28, 2020

(87) PCT Pub. No.: WO2019/191776
PCT Pub. Date: Oct. 3, 2019

(65) Prior Publication Data
US 2021/0015803 A1 Jan. 21, 2021

Related U.S. Application Data

(60) Provisional application No. 62/651,133, filed on Mar. 31, 2018.

(51) Int. Cl.
*A61K 31/4375* (2006.01)
*A61P 35/00* (2006.01)

(52) U.S. Cl.
CPC .......... *A61K 31/4375* (2013.01); *A61P 35/00* (2018.01)

(58) Field of Classification Search
CPC ......... A61K 31/475; A61P 29/00; A61P 35/00
See application file for complete search history.

(56) References Cited

U.S. PATENT DOCUMENTS

| | | |
|---|---|---|
| 3,415,831 A | 12/1968 | Weisbach |
| 3,455,936 A | 7/1969 | Douglas et al. |
| 3,468,890 A | 9/1969 | Archer |
| 3,814,773 A | 6/1974 | Herbst et al. |
| 3,943,148 A | 3/1976 | Herbst et al. |
| 4,057,551 A | 11/1977 | Szantay et al. |
| 4,399,069 A | 8/1983 | Szantay et al. |
| 5,519,028 A | 5/1996 | Beljanski |
| 6,630,482 B1 | 10/2003 | Becq et al. |
| 7,341,749 B2 | 3/2008 | Hall et al. |
| 9,440,913 B2 | 9/2016 | Saimoto et al. |
| 2005/0266107 A1* | 12/2005 | Hall ........................ A61P 43/00 424/750 |
| 2007/0293527 A9 | 12/2007 | Din Belle et al. |
| 2009/0215853 A1 | 8/2009 | Hall et al. |
| 2010/0256177 A1 | 10/2010 | Seshagiri |

FOREIGN PATENT DOCUMENTS

| | | |
|---|---|---|
| DE | 689 09 019 T2 | 3/1994 |
| EP | 0 059 817 A1 | 3/1981 |
| EP | 0 373 986 A1 | 6/1990 |
| FR | 2 419 725 A1 | 10/1979 |
| FR | 2 450 607 A2 | 10/1980 |
| JP | 2004-231601 A | 8/2004 |
| WO | 94/02146 A1 | 2/1994 |
| WO | 02/094270 A2 | 11/2002 |
| WO | 2005/121143 A1 | 12/2005 |

OTHER PUBLICATIONS

Pan, et al, Synthesis and Cytoxicity of Sempervirine and Analogues, J. of Org. Chem., 81, 2194-2200 (2016). (Year: 2016).*
International Search Report issued in PCT/US2019/025234; dated Jul. 3, 2019, four pages.
Written Opinion of the ISA issued in PCT/US2019/025234; dated Jul. 3, 2019, five pages.
Pan & Bannister "Sequential Sonagashira and Larock indole synthesis reactions in a general strategy to prepare biologically active beta-carboline-containing alkaloids" Organic Lett (2014) 16 (23): 6124-6127.
Suarez et al. "Targeting DNA with small molecules: A comparative study of a library of azonia aromatic chromophores" Org & Biomol Chem (2015) 13 (2): 527-538.
Danieli et al. "Convenient and expeditious synthesis of some indoloquinolizine alkaloids" J Chem Soc Chem Comm (1980) 18: 860-861.
Fuerstner et al. "Syntheses of camalexin, indolopyridocoline and flavopereirine" Tetrahedron (1995) 51 (3): 773-786.
Abarca et al. "Efficient synthesis of an Indoloquinolizinium alkaloid selective DNA-binder by ring-closing metathesis" Org Lett, 16, 3464-3467 (2014).
Bassleer et al. "Effects of dihydroflavopereirine and sempervirine (ß-carbolinium alkaloids) on cancer cells in culture" Ann Pharm Fr, 43, 83-88 (1985).

(Continued)

*Primary Examiner* — Erich A Leeser
(74) *Attorney, Agent, or Firm* — Studebaker & Brackett PC

(57) ABSTRACT

De-ethylflavopereirine, a pharmaceutically acceptable salt thereof, a solvate or a hydrate thereof, or a pharmaceutically acceptable salt of a solvate or a hydrate thereof may be used as cancer therapy (i.e., prevention and/or treatment) in a subject in need thereof, including a pathological condition such as inflammation, especially chronic, or cancer (e.g., a carcinoma, a sarcoma, a melanoma, a leukemia, a lymphoma), especially a solid tumor and/or a metastasis thereof. In particular, systemic administration of such improved anti-cancer agents in effective amounts may selectively destroy cancer cells (including cancer stem cells) in a solid tumor and/or at a site of metastasis. They are well-tolerated by the subject, even at large systemic doses and their resulting high concentrations in the circulation, and provide safe and effective anti-cancer agents.

16 Claims, 28 Drawing Sheets

(56) References Cited

OTHER PUBLICATIONS

Beljanski & Beljanski "Selective inhibition of in vitro synthesis of cancer DNA by alkaloids of ß-carboline class" Expl Cell Biol, 50, 79-87 (1982).
Beljanski & Beljanski "Three alkaloids as selective destroyers of the proliferative capacity of cancer cells" IRCS Med Sci, 12, 587-588 (1984).
Beljanski "The anticancer agent PB-100, selectively active on malignant cells, inhibits multiplication of sixteen malignant cell lines, even multidrug resistant" Genet Mol Bio, 23, 29-33 (2000).
Beljanski Foundation "Pao Pereira Monograph" found at http://www.beljanski.org/engl/wp-content/uploads/Monograph_pa_pereira.pdf, seven pages (2015 or later?).
Bemis et al. "Anti-prostate cancer activity of a ß-carboline alkaloid enriched extract from Rauwolfia vomitoria" Int J Oncol, 29, 1065-1073 (2006).
Bemis et al. "ß-carboline alkaloid-enriched extract from the Amazonian rain forest tree pao pereira suppresses prostate cancer cells" J Soc Integr Oncol, 7, 59-65 (2009).
Brandao et al. "Medicinal plants and other botanical products from the Brazilian Official Pharmacopoeia" Rev Bras Farmacogn, 16, 408-420 (2006).
Calvez "Flavopereirine is an intercalating agent for non-supercoiled DNA" Cancer Detect Prev, 22 (suppl), abstract 623 (1998).
Camargo et al. "Chemical composition, ethnopharmacology and biological activity of *Geissospermum Allemão* species (Apocynaceae Juss.)" Revista Fitos, 8, 137-146 (2013).
Cao et al. "ß-carboline alkaloids: Biochemical and pharmacological functions" Curr Med Chem, 14, 479-500 (2007).
Chang et al. "Pao pereira extract suppresses castration-resistant prostate cancer cell growth, survival, and invasion through inhibition of NFκB signaling" Integr Cancer Ther, 13, 249-258 (2014).
Chen et al. "A potent derivative of indolizino[6,7-b]indole for treatment of human non-small cell lung cancer cells" Neoplasia, 18, 199-212 (2016).
Chen et al. "Flavopereirine inhibits autophagy via the AKT/p38 MAPK signaling pathway in MDA-MB-231 cells" Int J Mol Sci, 21, 5362, 9 pages (Jul. 2020).
Day et al. "Preclinical mouse cancer models: A maze of opportunities and challenges" Cell, 163, 39-53 (2015).
Dong et al. "Extract of the medicinal plant Pao Pereira inhibits pancreatic cancer stem-like cell in vitro and in vivo" Integr Cancer Ther, 17, 1204-1215 (Jul. 2018).
Frederick et al. "Novel trisubstituted harmine derivatives with original in vitro anticancer activity" J Med Chem, 55, 6489-6501 (2012).
Fuerstner "Low-valent transition metal induced C—C bond formations: Stoichiometric reactions evolving into catalytic processes" Pure Appl Chem, 70, 1071-1076 (1998).
Hall "DNA destabilization, cancer, and inflammation" Anti-Aging Therapeutics, XIII, 53-64 (2011).
Li et al. "Flavopereirine suppresses the growth of colorectal cancer cells through P53 signaling dependence" Cancers, 11, 1034, 15 pages (Jul. 2019).
Liu et al. "Pao Pereira extract attenuates testosterone-induced benign prostatic hyperplasia in rats by inhibiting 5α-reductase" Sci Rep, 9, 19703, 10 pages (Dec. 2019).
Manna et al. "Synthesis of indole alkaloids and alkaloidal precursors: An improved synthesis of flavopereirine" J Chem Res, S, 350-351 (1999).
Matia et al. "New uses of Westphal condensation: Synthesis of flavocorylene and related indolo[2,3-a]quinolizinium salts" Tetrahedron Letters, 32, 7575-7578 (1991).
Pubchem "De-ethylflavopereirine sulfate" at https://pubchem.ncbi.nlm.nih.gov/compound/De-ethylflavopereirine-sulfate, ten pages, downloaded Jan. 14, 2021.
Pubchem "Substance record 239-17-8" at https://pubchem.ncbi.nlm.nih.gov/substance/347718124 and ABCR's "De-ethylflavopereirine sulfate" at https://abcr.com/de_en/ab483826, six pages, downloaded Jan. 14, 2021.
Pubchem "Substance record 239-17-8" at https://pubchem.ncbi.nlm.nih.gov/substance/346569987 and Lab-Network's "12H-indolo[2,3-a]quinolizin-5-ium hydrogensulfate" at https://labnetwork.com/frontend-app/p/#!/moleculedetails/LN03246530, nine pages, downloaded Jan. 14, 2021.
Ren et al. "Flavonoids: Promising anticancer agents" Medicinal Res Rev, 23, 519-534 (2003).
Sajkowska-Kozielewicz et al. "Antioxidant, cytotoxic, and antiproliferative activities and total polyphenol contents of the extracts of Geissospermum reticulatum bark" Oxid Med Cell Longev, 2016, 2573580, eight pages (2016).
Silva et al. "Flavopereirine—an alkaloid derived from Geissospermum vellosii—presents leishmanicidal activity in vitro" Molecules, 24, 785, 13 pages (Feb. 2019).
Yu et al. "Inhibition of pancreatic cancer and potentiation of gemcitabine effects by the extract of Pao Pereira" Oncol Rep, 30, 149-156 (2013).
Yu & Chen "The plant extract of Pao pereira potentiates carboplatin effects against ovarian cancer" Pharm Biol, 52, 36-43 (2014).
Ahmad et al. "Targeting cell cycle by β-carboline alkaloids in vitro: Novel therapeutic prospects for the treatment of cancer" Chem-Biol Interact, 330, 109229, nine pages (2020).
Chabner "NCI-60 cell line screening: A radical departure in its time" J Natl Cancer Inst, 108, djv388, seven pages, (2016).
Eastman "Improving anticancer drug development begins with cell culture: Misinformation perpetrated by the misuse of cytotoxicity assays" Oncotarget, 8, 8854-8866 (2017).
Garnett & Mcdermott "The evolving role of cancer cell line-based screens to define the impact of cancer genomes on drug response" Curr Opin Genet Dev, 24, 114-119 (2014).
Johnson et al. "Relationships between drug activity in NCI preclinical in vitro and in vivo models and early clinical trials" Br J Cancer, 84, 1424-1431 (2001).
Kumar et al. "Recent insights into synthetic β-carbolines with anti-cancer activities" Eur J Med Chem, 142, 48-73 (2017).
Laine et al. "Pharmacological importance of optically active tetrahydro-β-carbolines and synthetic approaches to create the C1 stereocenter" Molecules, 19, 1544-1567 (2014).
López-Lázaro "A simple and reliable approach for assessing anticancer activity in vitro" Curr Med Chem, 22, 1324-1334 (2015).
Monga & Sausville "Developmental Therapeutics Program at the NCI: Molecular target and drug discovery process" Leukemia, 16, 520-526 (2002).
Newman & Cragg "Natural products as sources of new drugs over the 30 years from 1981 to 2010" J Nat Prods,75, 311-335 (2012).
Sayre & Watson "Final report on the alkaloids of Gelsemium" J Am Pharm Assoc, 8, 708-711 (1919).
Shang et al. "Biologically active quinoline and quinazoline alkaloids. Part I" Med Res Rev, 38, 775-828 (2018).
Shang et al. "Biologically active quinoline and quinazoline alkaloids. Part II" Med Res Rev, 38, 1614-1660 (2018).
Shoemaker "The NCI60 human tumour cell line anticancer drug screen" Nat Rev Cancer, 6, 813-823 (2006).
Stevenson & Sayre "Sempevirine from Gelsemium root" J Am Pharm Assoc, 4, 1458-1463 (1915).
Szabó et al. "Recent advances in the synthesis of β-carboline alkaloids" Molecules, 26, 66, 55 pages (2021).

* cited by examiner

Flavopereirine De-ethylflavopereirine

Figure 2
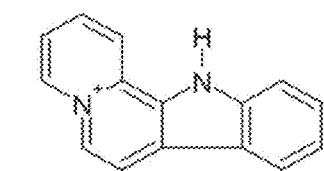
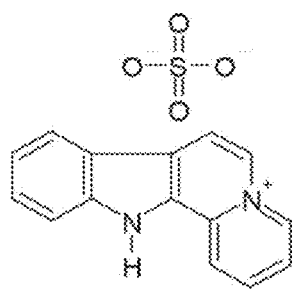
CHEMICAL FORMULA
$C_{30}H_{22}N_4O_4S$
MOLECULAR WEIGHT
534.60
Figure 3
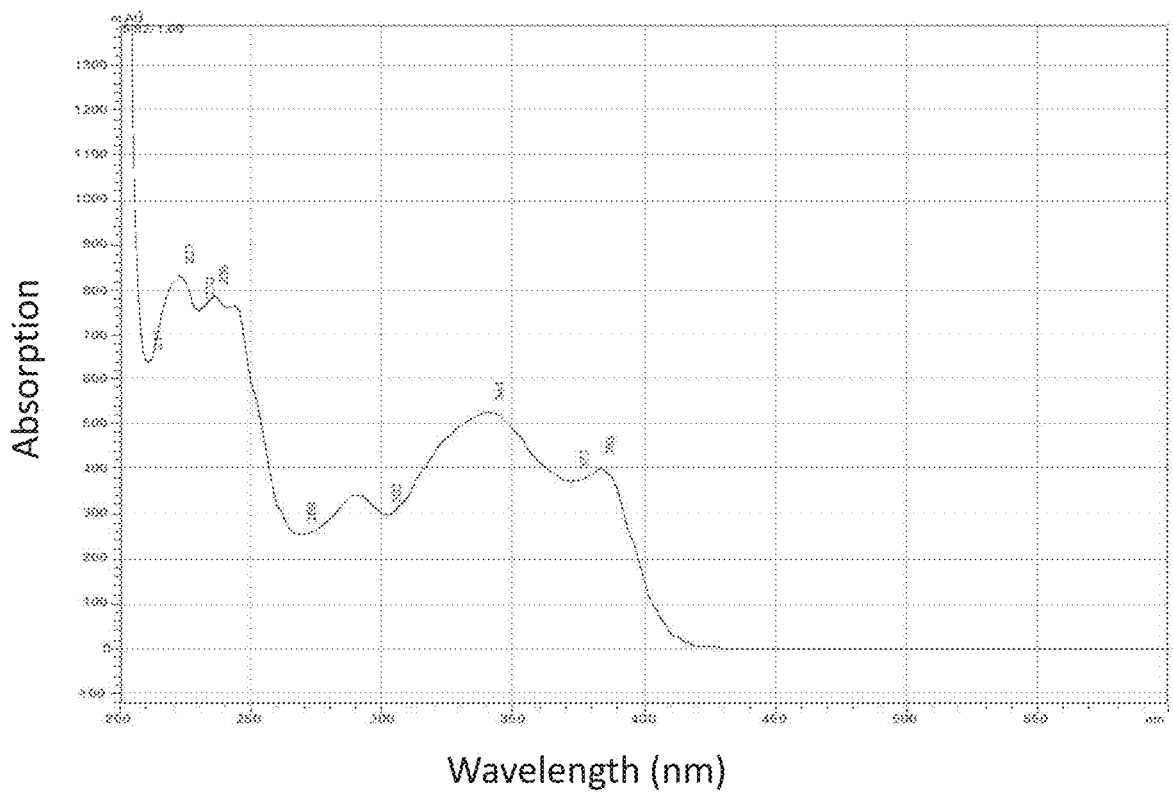

Figure 9
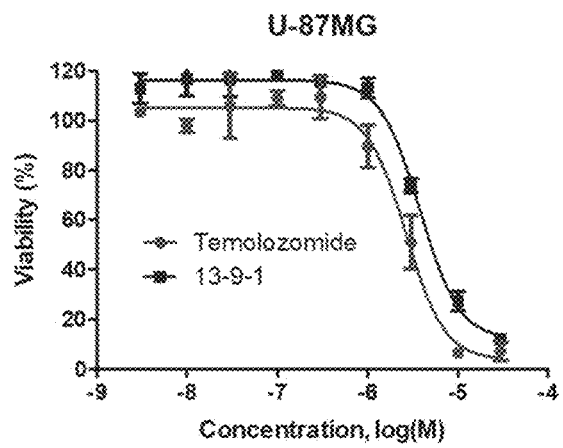
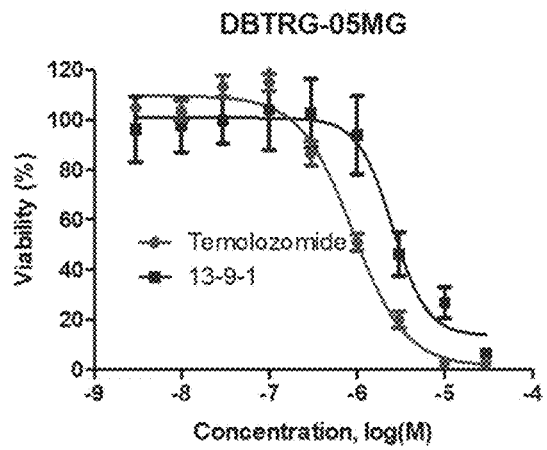
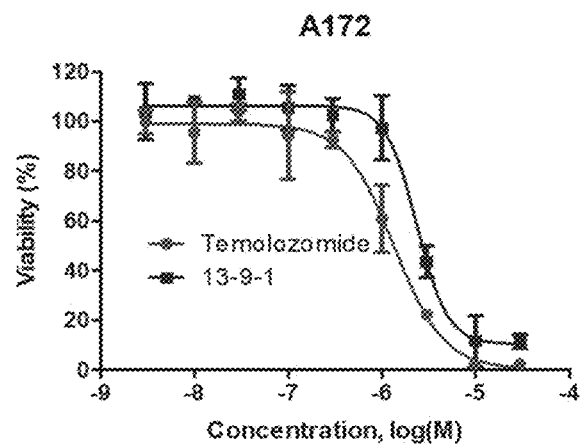
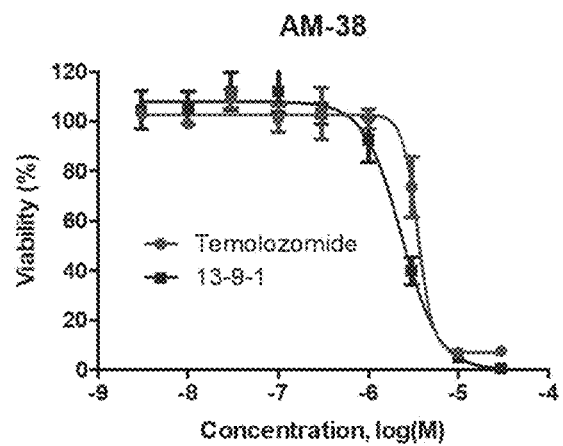

EFFECT OF 13-9-1 ON HT-29 COLON CANCER CELLS

Values are expressed as means ± SEM (n=3).
*p≤0.05, compared with control group using the Student's t-test.
**p≤0.01, compared with control group using the Student's t-test

Pancreatic Cancer PANC-1

Figure 16
A Tumor Burden Total Photon
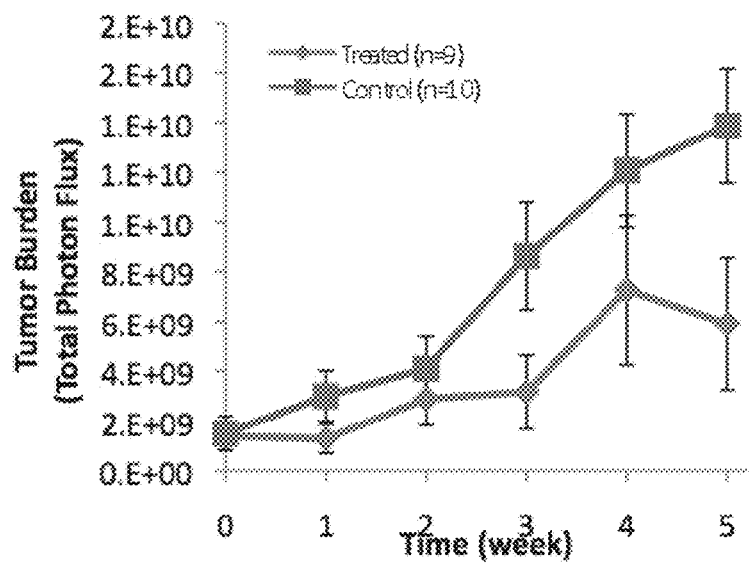
B Log Transform Total Photon
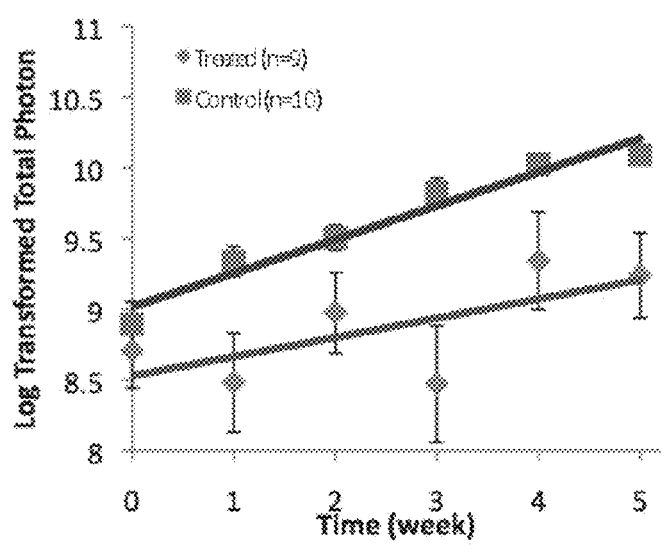

Figure 20
A
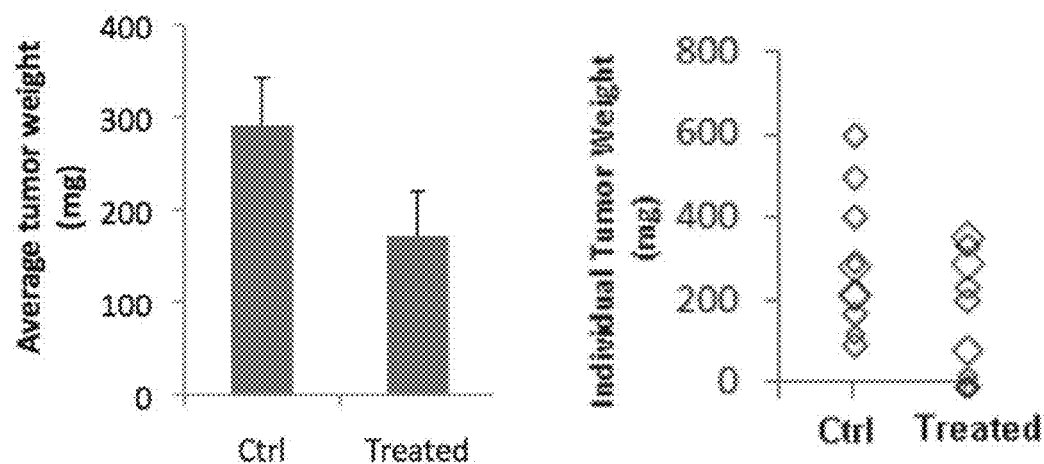
B
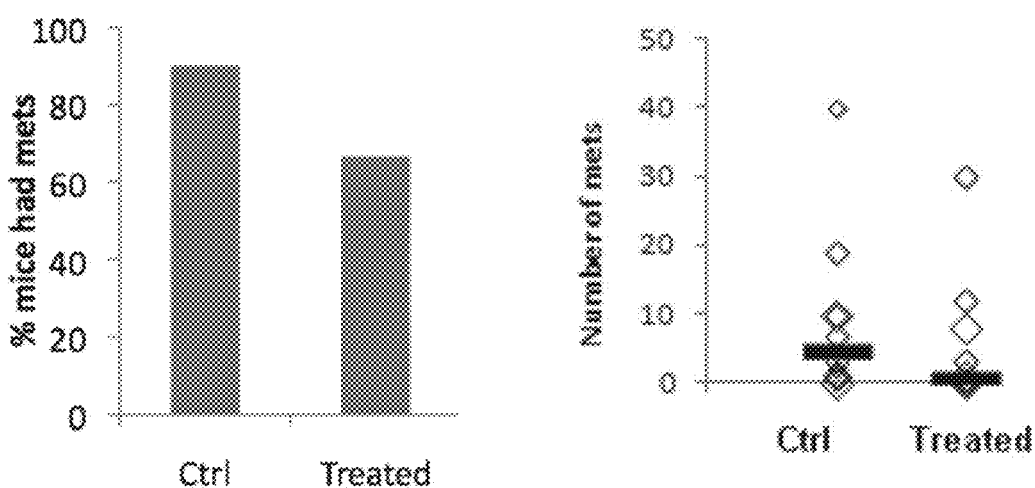

Figure 24
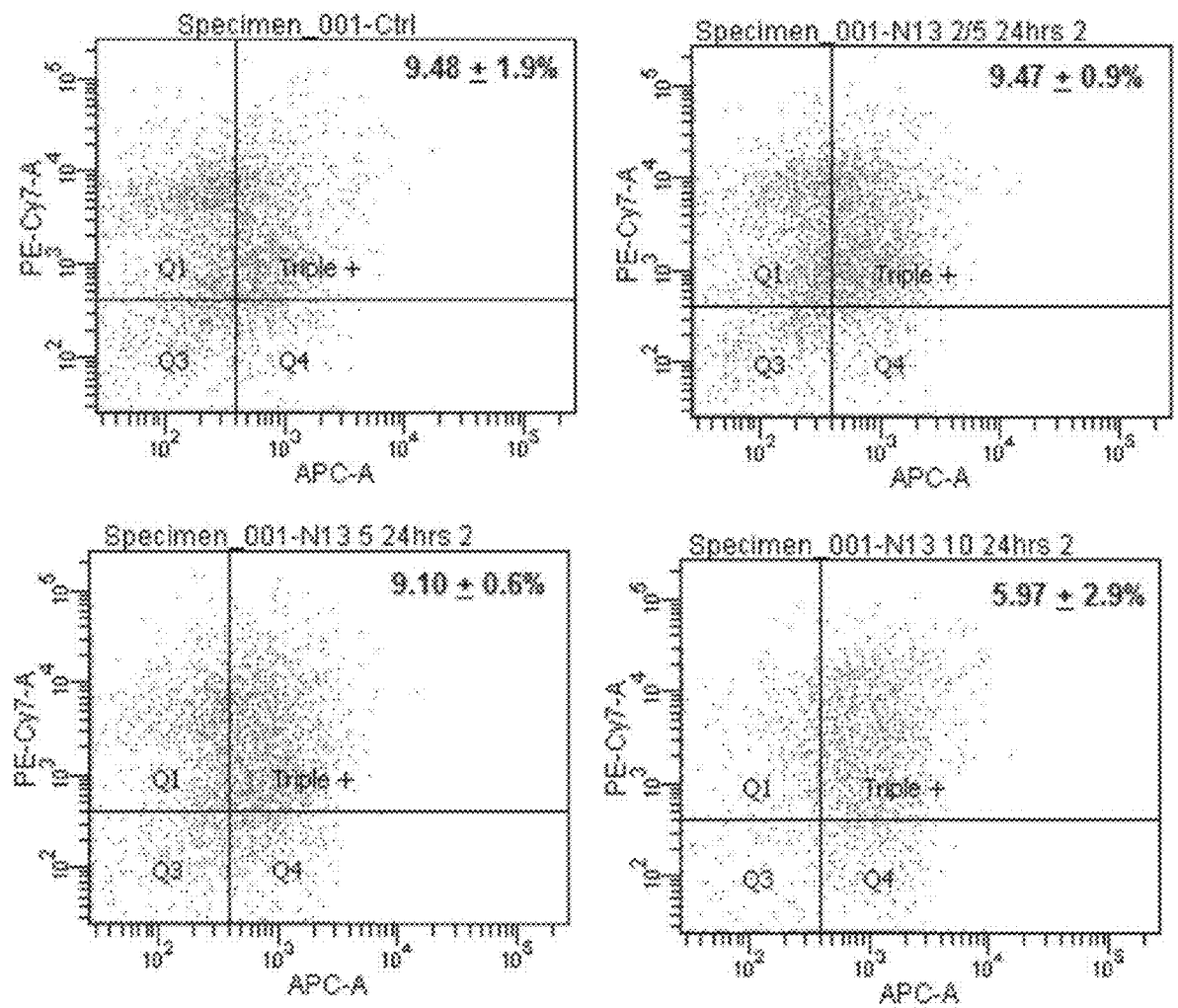
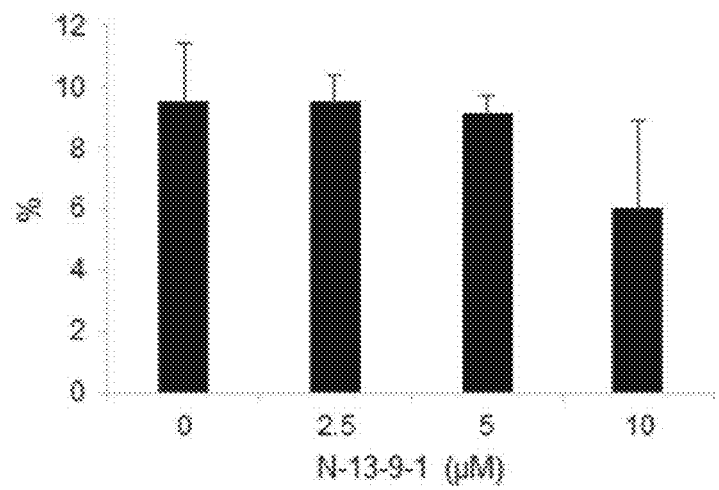

Figure 26
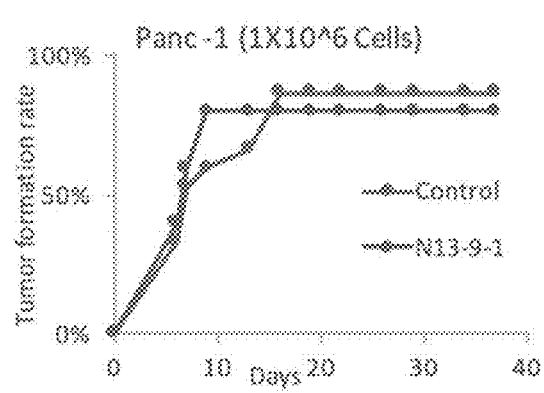 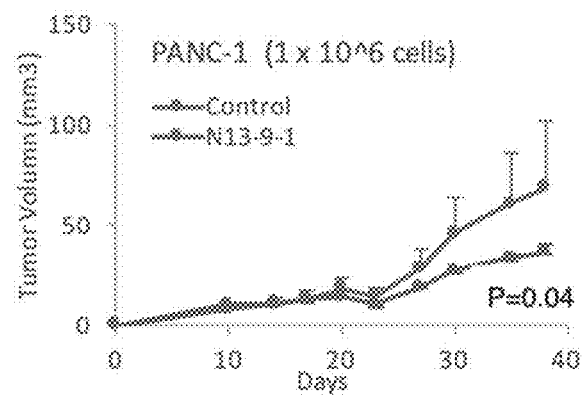
A.
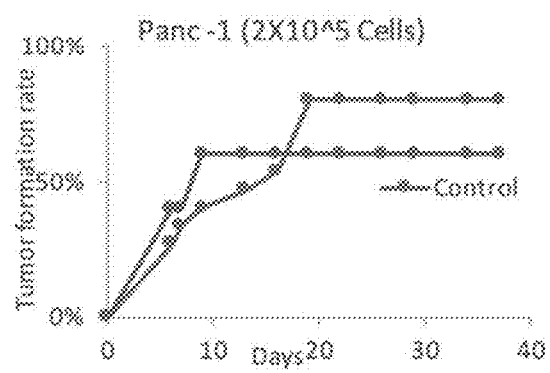 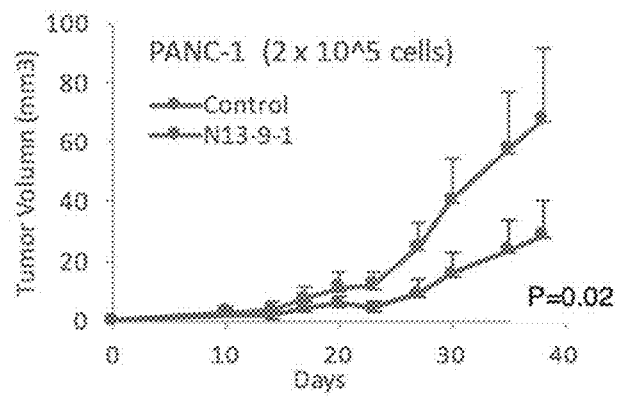
B.
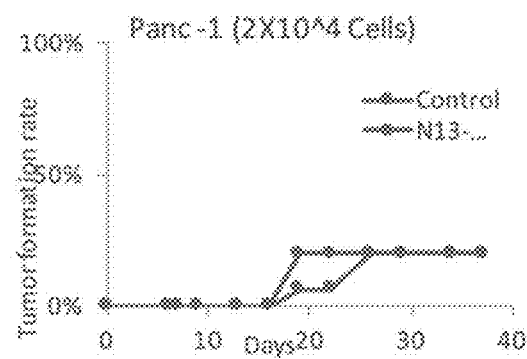 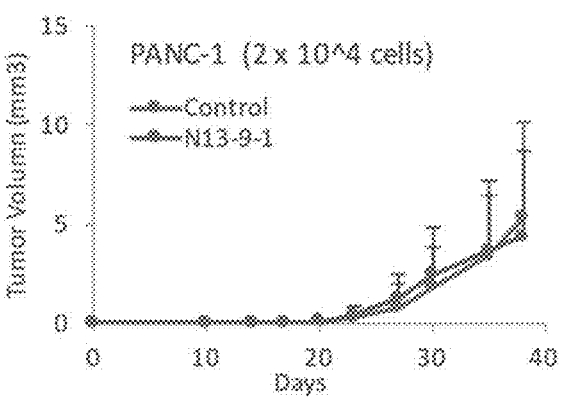
C.

Figure 29
A  Tissue Protection: Histology
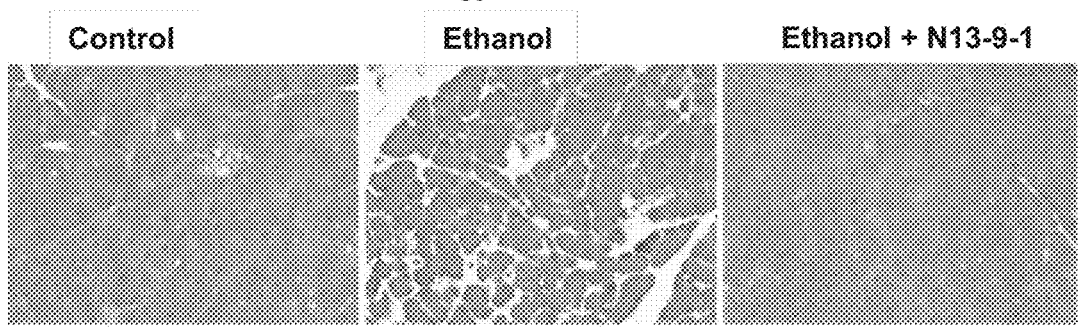
B  Injury Score
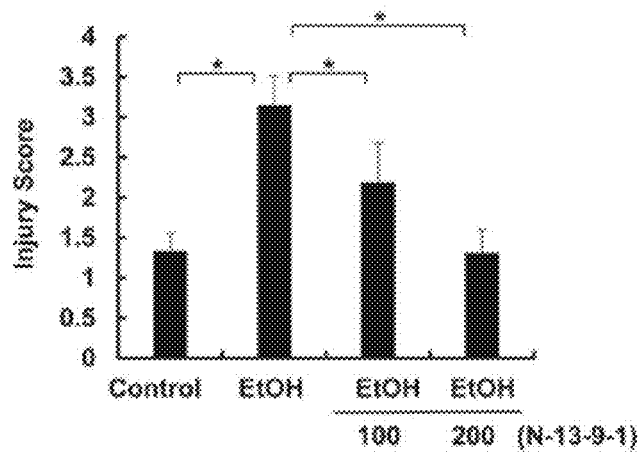
C  Anti-Inflammation
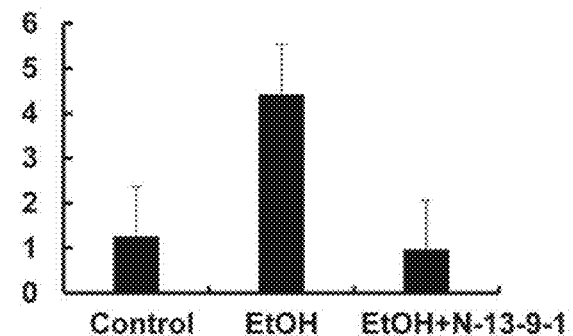

SELECTIVE ANTI-CANCER AGENT EFFECTIVE FOR PREVENTION AND TREATMENT

CROSS-REFERENCE TO RELATED APPLICATION

This application claims priority from U.S. Provisional Application No. 62/651,133, filed Mar. 31, 2018; which is incorporated herein by reference.

FIELD OF THE INVENTION

This invention generally relates to treatment of cancer, especially a solid tumor, and reduction of the risk for cancer recurrence. In particular, the invention relates to administration of de-ethylflavopereirine, or a salt, or a solvate (e.g., a hydrate), or a salt of a solvate or a hydrate thereof (i.e., compounds of the present invention) for therapy of cancer within a subject. A compound of the present invention may selectively destroy cancer cells, especially in a solid tumor and/or its metastases, with no noticeable harmful effects on noncancerous cells and without the side effects associated with other cytotoxic chemotherapeutic agents. The compound has been well tolerated when administered in large doses and achieving high systemic concentrations. Thus, it may be administered to a subject in remission, when other cytotoxic chemotherapeutic agents are withdrawn to improve the subject's quality of life, and thereby reduce the risk of relapse caused by growth of micrometastases, residual cancer cells, or cancer stem cells. One or more compounds of the present invention may be used alone or in combination with other therapeutic agents and cancer therapies.

BACKGROUND OF THE INVENTION

It has been established for decades that the DNA purified from a cancer cell is different from the DNA of a normal cell in its secondary structure as well as its primary structure. Secondary structure refers to the two strands of DNA that form a double helix stabilized by hydrogen bonds. Primary structure refers to the sequence of the DNA, the genetic code for proteins. Differences between cancer cell DNA and normal cell DNA have been almost exclusively associated with mutations in the DNA sequence of the tumor cells; that is, changes in the primary structure of the DNA that are thought to be and often prove to be causal factors in cancer progression.

Yet the secondary structure of cancer cell DNA is different from its normal structure: two independent laboratories using either UV or IR spectroscopy have shown that cancer DNA is physically changed from normal DNA. Their assays showed that in the DNA of cancer cells, hydrogen bonds that stabilize the DNA duplex are broken, molecular bonds are stretched, and atoms are substituted or absent. These laboratories provided evidence that this 'destabilized' or 'disordered' DNA occurs after long-term exposure to carcinogens and oxidative damage.

De-ethylflavopereirine targets the altered structures characteristic of cancer cell DNA. Since these structural alterations occur in the cancer cells of all tumors of both genders, the anti-cancer effect of de-ethylflavopereirine is broad spectrum. This is, of course, a tremendous advantage over other targeted therapies that may focus on mutated proteins with carcinogenic potential, with different types of cancer cells carrying various mutations. De-ethyl-flavopereirine does not target the altered proteins caused by mutations in DNA—rather it targets the damaged physical structure of cancer cell DNA itself.

The specific targeting of cancer DNA whose secondary structure is damaged is a major breakthrough in anti-cancer strategies. This phenomenon may explain the absence of toxicity or noticeable side effects associated with de-ethylflavopereirine because a healthy cell with normal DNA structure offers no target for this compound.

As shown herein, de-ethylflavopereirine exhibits the broad-spectrum activity of a chemotherapeutic agent that targets the altered DNA found in cancer cells. Here, the in vivo, preclinical studies focus on pancreatic and colon cancer. The former is usually aggressive and intractable; the latter is more common and often lethal. Both can be effectively prevented or treated with this new therapy. For these two cancers, pharmacokinetic data showed localization of de-ethylflavopereirine in the pancreas and colon, which justifies studying the compound's anti-cancer and anti-tumor activity in relevant animal models. De-ethylflavopereirine also accumulates and persists in other organs (e.g., lung, spleen, kidney, liver, and ovary). Such results indicate that these cancers are excellent targets for de-ethylflavopereirine-based therapies.

Pancreatic Cancer

Pancreatic cancer is the seventh leading cause of cancer deaths in the United States. In 2018, the American Cancer Society's estimates for pancreatic cancer in the United States are: about 55,440 people (29,200 men and 26,240 women) will be diagnosed with pancreatic cancer; about 44,330 people (23,020 men and 21,310 women) will die of pancreatic cancer. The rate for pancreatic cancer has been slowly increasing over the past 10 years. The lifetime risk of developing pancreatic cancer in 2013 was about 1 in 78 (1.47%) while the lifetime risk in 2017 was about 1 in 65 (1.5%).

As with most cancers, a person's risk of developing pancreatic cancer appears to depend on a combination of behavioral factors and genetic or environmental factors. Unlike most cancers, conventional treatments have little impact on the course of the disease; almost all patients diagnosed with pancreatic cancer develop metastases and die. The five-year survival rate is less than 4% and this rate has not changed significantly in 25 years.

Pancreatic cancer is often asymptomatic in its early stages so it is commonly diagnosed in later, more aggressive stages when it is no longer resectable. Gemcitabine, the front-line drug for pancreatic cancer, may slow progress of the disease when first administered, but tumors become resistant to the drug, rendering it ineffective. Treatment options are then reduced to palliative care.

Thus, there is an urgent need for a new anti-pancreatic cancer treatment that shrinks tumors, circumvents drug resistance, and prolongs life while having minimal impact on the quality of life. The present invention describes such a novel treatment.

Colorectal Cancer

Excluding skin cancers, colorectal cancer is the third most common cancer diagnosed in both men and women in the United States. The American Cancer Society's estimates for the number of colorectal cancer cases in the United States for 2018 are: 97,220 new cases of colon cancer and 42,030 new cases of rectal cancer. The lifetime risk of developing colorectal cancer is about 1 in 21 (4.7%) and when data for men and women are combined it is the third leading cause of cancer deaths in the United States. It is expected to cause about 50,630 deaths during 2018.

Screening techniques now enable early detection of polyps that can be removed prior to becoming cancerous. Cancers detected early are more amenable to treatment, generally, so the death rate (the number of deaths per 100,000 people per year) from colorectal cancer has dropped in both men and women over the past 20 years. Improvements in treatment over the last several years have enabled more than one million to survive colorectal cancer in the United States. Nevertheless, over 50,000 deaths are expected from colorectal cancer during 2018.

The present invention addresses the challenge of developing a next generation of cancer treatment that provides significantly better survival for patients with Stage II, III, and IV cancer, and avoids negative side effects associated with current treatment modalities by novel, structurally related compounds that are safe, well-tolerated, and effective anti-cancer agents. Although WO 2005/1211143, EP 1758905, and US 2010/0256177 were directed to flavopereirine derivatives for cancer therapy, a compound of the present invention was not disclosed therein. More importantly, the safety and efficacy of prior art compounds were not determined.

SUMMARY OF THE INVENTION

An active pharmaceutical ingredient (API) of the invention is a synthetic (i.e., artificial and not natural) compound that is exemplified by de-ethylflavopereirine, its pharmaceutically acceptable salts, its solvates (e.g., hydrates), and pharmaceutically acceptable salts of such solvates and hydrates, which is optionally in amorphous, crystalline, or other polymorphic dry forms, being relatively nontoxic and having at least anti-cancer activity for one or more types of neoplasia or malignancy. De-ethylflavopereirine has the chemical name 12H-indolo[2,3-a]quinolizin-5-ium or 12H-pyrido[2,1-a]β-carbolin-5-ium. A synthetic compound of the present invention is structurally related to a β-carboline alkaloid known as flavopereirine that is obtained from certain plants but more effective than the natural compound. A synthetic compound of the present invention can be in a dry form (e.g., compressed or loose powder, finely divided or granulated) or in a liquid form (especially dissolved or suspended in a solution, aqueous or oily, thin or thick, emulsified or multiphasic, isotropic or smectic) suitable for at least dissolving homogeneously into solvent, dispersing into suspension, mixing into a composition, blending, homogenizing, emulsifying, compressing, tableting, encapsulating, or any combination thereof. After synthesis, they can be processed by a further step to chemically or physically change their properties (but not their anti-cancer activity), formulated with inactive ingredients (e.g., a vehicle used as the carrier such as water for injection, a salt, a buffer, a sugar, a stabilizer, an antioxidant or other preservative, a liquid diluent or a solid filler, a binder, a lubricant, a surfactant, a dessicant, a dispersant, a coating, a polymeric matrix or support, or any combination thereof) under aseptic conditions into a pharmaceutical composition, optionally lyophilized or freeze dried, sterile packaged into a kit (e.g., hermetically sealed container for powder or granules, blister pack of multiple doses, single unit dose in container for reconstitution, device for infusion or injection) with a use label, and stored until needed in liquid or solid form suitable for future administration to a subject (i.e., human patient or animal subject).

De-ethylflavopereirine may be used as a medicament or other therapeutic substance. It is representative of a novel class of chemotherapeutic agents. Without being bound to any required mechanism of action for operation of the invention, but to understand how it could be understood in the context of multistep carcinogenesis and its usefulness in medical applications not specifically described herein, the compounds may selectively target physically-damaged DNA structures in cells that depend on genomic instability and/or genetic mutation to advance through the steps to malignancy. Therefore, this novel class of chemotherapeutic agents may exert a broad-spectrum effect against many different types of pre-cancerous conditions (e.g., chronic inflammation), cancers, solid tumors, metastases, and cancer stem cells. They may selectively kill cancer cells originating from or within colon, pancreas, lung, kidney, ovary, and brain as well as other organs.

The cancer may be a carcinoma (e.g., adenocarcinoma or squamous cell carcinoma), a sarcoma (e.g., bone or soft tissue), a melanoma, a leukemia, or a lymphoma. More particularly, the invention relates to therapy for cancer in which a primary tumor is derived from or in one of bone marrow, blood, lymph node, breast, prostate, colon, rectum, lung, uterus, ovary, bladder, skin, muscle, kidney, mouth, pancreas, liver, stomach, esophagus, cervix, thyroid, bone, brain, spinal cord, or testicle. While a primary solid tumor originates in one of the foregoing organs, a secondary tumor (i.e., a metastasis) would be found in another location. Imaging by nuclear medicine or radiology requires a tumor to be of sufficient size to be detected. Even careful pathological examination may not detect small tumors or micrometastases. Thus, after surgical removal of a primary tumor, systemic administration of a compound of the present invention enables coverage of a subject's body to the limits of its systemic circulation including locations where no cancer cells are apparent. Analogously, after treating a leukemia or a lymphoma until a subject is in remission, a compound of the present invention circulating in blood kills or at least suppresses growth of residual cancer cells. A method of cancer therapy as described herein may be performed as neoadjuvant before a definitive treatment (e.g., surgery alone, radiation alone, or one followed by the other), or as adjuvant during and/or after radiotherapy or chemotherapy, or by itself or as part of rescue treatment after relapse or recurrence of cancer, or by itself or as part of palliative treatment.

A compound of the present invention may be administered enterally (e.g., perorally), parenterally (e.g., intravenous or intra-arterial through a needle or tube inserted into vein or artery respectively, intraperitoneal or intra-vesical infusion, subcutaneous or intramuscular injection, intrathecal delivery, transdermal for diffusion through skin to achieve systemic distribution, transmucosal such as inhalation, insufflation, sublinguinal, or sublabial), or topically (e.g., transdermal for application on skin to achieve local distribution, inhalation). Enteral or parenteral administration is preferred; enteral administration is more preferred. Self-administration is preferred and may be once or twice daily in solid form (e.g., a pharmaceutical composition containing a compound of the present invention in tablets including coated tablets, capsules including delayed/sustained release capsules) or liquid form (e.g., an alcohol- or aqueous-based solution delivered as drops, emulsion, foam, gel, liposomes, rinse, or spray; lotion, cream, or ointment; absorbed into an artificial polymer, chewing gum, sponge, or suppository), which optionally may also include therein one or more other chemotherapeutic agents. Otherwise, a trained healthcare professional may administer a compound of the invention two or three times per day, or at daily, alternate day, weekly, biweekly, or monthly intervals.

Cancer may be treated by administration of a de-ethylflavopereirine compound in one or more doses to a subject in need of treatment. The therapeutic compound is de-ethylflavopereirine, a salt thereof, a solvate thereof, a hydrate thereof, or a salt of the solvate or the hydrate. Thus, the de-ethylflavopereirine compound may be used for the treatment of the subject or, alternatively, for the manufacture of a pharmaceutical composition and/or a medical device, including a kit of parts, for treatment of the subject.

Chronic inflammation may also be treated by administration of a de-ethylflavopereirine compound in one or more doses to a subject in need of thereof. The therapeutic compound is de-ethylflavopereirine, a salt thereof, a solvate thereof, a hydrate thereof, or a salt of the solvate or the hydrate. Thus, the de-ethylflavopereirine compound may be used for therapy of a subject or, alternatively, for the manufacture of a pharmaceutical composition and/or a medical device, including a kit of parts, for therapy of the subject. In particular, reduction of chronic inflammation in a subject may prevent cancer because the former causes DNA damage, genomic instability, genetic mutation, or any combination thereof, and is a risk factor for the development of cancer. For example, treating chronic pancreatitis, gastritis, hepatitis, or ulcerative colitis/Crohn disease by administration of at least the de-ethylflavopereirine compound, composition, or device may reduce the incidence of pancreatic, gastric, hepatic, or colon cancer, respectively.

Therapy may be for one, two, three, four, six, nine, 12, 18, 24, 36, or more months in solid or liquid form (e.g., a pharmaceutical composition containing a compound of the present invention may be distributed under aseptic and stabilized conditions from the manufacturer through a supply chain to a healthcare provider or compounder; the solid form is reconstituted in a form suitable for infusion, injection, or delivery via pump or reservoir; optionally, combined with one or more other chemotherapeutic agents). For example, daily administration for one or two months, then stopping for one or two months before starting again.

A pharmaceutical composition or a medical device, including a kit of parts, comprising a therapeutically effective amount of one or more de-ethylflavopereirine compounds may also be provided. The one or more therapeutic compounds are de-ethylflavopereirine, a salt thereof, a solvate thereof, a hydrate thereof, a salt of the solvate or the hydrate, or any combination thereof.

This invention is a major advance in cancer therapy, including the prevention and treatment of aggressive cancers. Negative side effects such as systemic toxicity may be minimized or even unnoticeable.

BRIEF DESCRIPTION OF THE DRAWINGS

Synthesis, Structure, and Purity of De-Ethylflavopereirine

FIG. 2. Chemical structures of de-ethylflavopereirine (top) and its sulfate salt (bottom); chemical formula and molecular weight of the latter.

FIG. 3. Characteristic ultraviolet (UV) absorption spectrum of synthetic de-ethylflavopereirine. Absorption (y-axis) is plotted against the wavelength in nanometers (x-axis).

Anti-Cancer Activity of De-Ethylflavopereirine: Ovarian, Pancreatic, Glioblastoma, and Colon Cancer Cell Lines FIG. 7. Dose-response curves for cell viability of human ovarian cancer cell lines OVCAR-5 (triangles), SHIN-3 (squares), and OVCAR-8 (lozenges) exposed to de-ethylflavopereirine. Cells were cultured in the presence of increasing concentrations of the compound for 48 hr and cell viability was determined by MTT assay. MRC-5 (crosses), an immortalized, normal human epithelial cell line, was used as a control.

Figure 8:
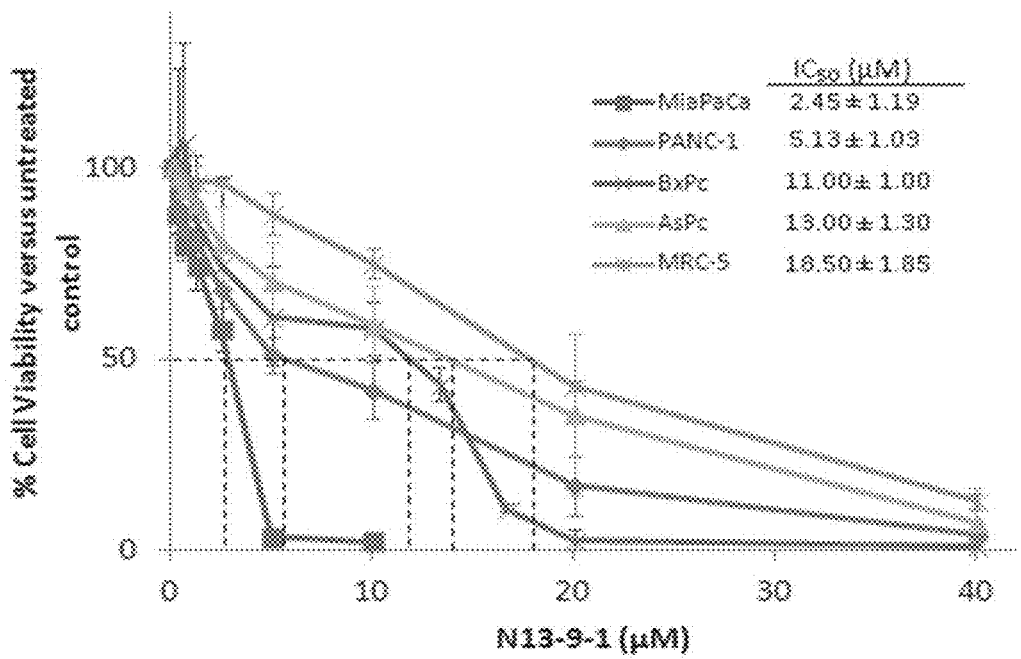

FIG. 8. Dose-response curves for cell viability of human pancreatic cancer cell lines MIA PaCa (squares), PANC-1 (lozenges), BxPc (crosses), and AsPc (triangles) exposed to de-ethylflavopereirine. Cells were cultured in the presence of increasing concentrations of the compound for 48 hr and cell viability was determined by MTT assay. MRC-5 (asterisks) was used as a control.

FIG. 9. Glioblastoma in vitro cell viability and proliferation assay after treatment with de-ethylflavopereirine. Glioblastoma cell lines U-87MG, DBTRG-05MG, A172, and AM-38 were tested. Temozolomide, an oral chemotherapy drug known to treat some brain cancers, was used as a control. The concentrations of temozolomide (circles) or compound 13-9-1 (squares) used were 3 nM, 10 nM, 30 nM, 100 nM, 1 uM, 3 uM, 10 uM, and 30 uM. Each of the cell lines was treated with de-ethylflavopereirine for 72 hr before measuring cytotoxicity and inhibition of cell proliferation. Number of viable cells in culture based on quantitation of ATP. IC50 was determined as indicated below each graph.

Figure 10:
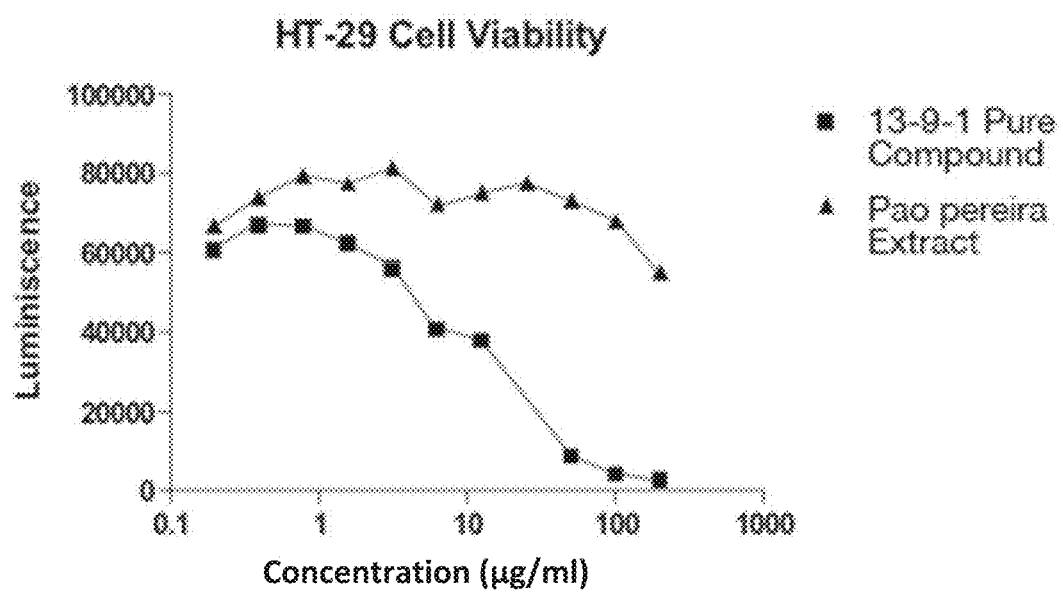

FIG. 10. Dose-response curve for human colon cancer cell line HT-29 exposed to either de-ethylflavopereirine (squares) or Pao pereira plant extract (triangles) containing flavopereirine and at least one other anti-cancer compound, dihydroflavopereirine. The bioluminescent HT-29 cell line was used.

Anti-Pancreatic Cancer Activity of De-Ethylflavopereirine

Figure 11:
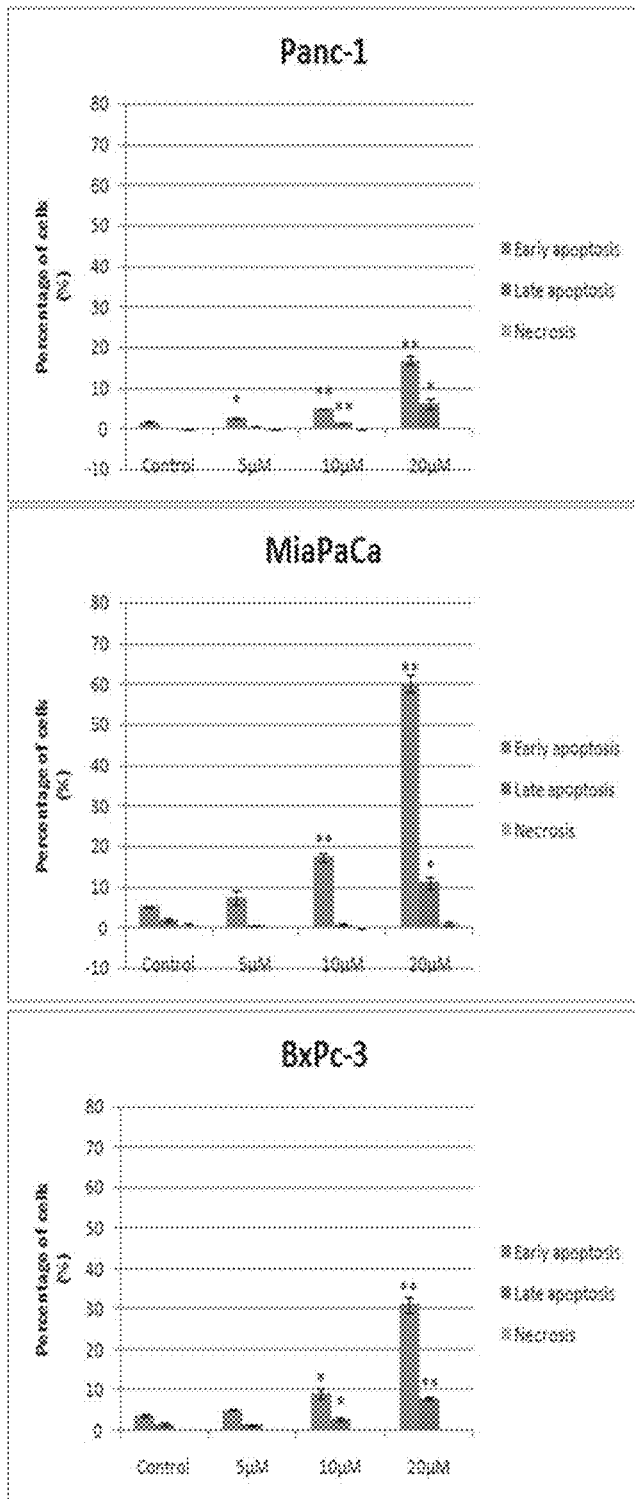

FIG. 11. De-ethylflavopereirine induces apoptosis in pancreatic cancer cell lines PANC-1 (top), MIA PaCa (middle), and BxPc (bottom). Following exposure of cells to de-ethylflavopereirine at concentrations of 0.5 μM, 10 μM, and 20 μM, flow cytometry was used to assess the percentage of cells undergoing early apoptosis (clear), late apoptosis (dark), or necrosis (stipple). Early apoptosis is the predominant result that is induced by de-ethylflavopereine as shown by the highest bar in the charts for all three cell lines at the 10 μM and 20 μM concentrations. Values are mean±SEM (n=3). *$p \leq 0.05$ compared with control group using Student's t-test; **$p \leq 0.01$ compared with control group using Student's t-test.

Figure 12:
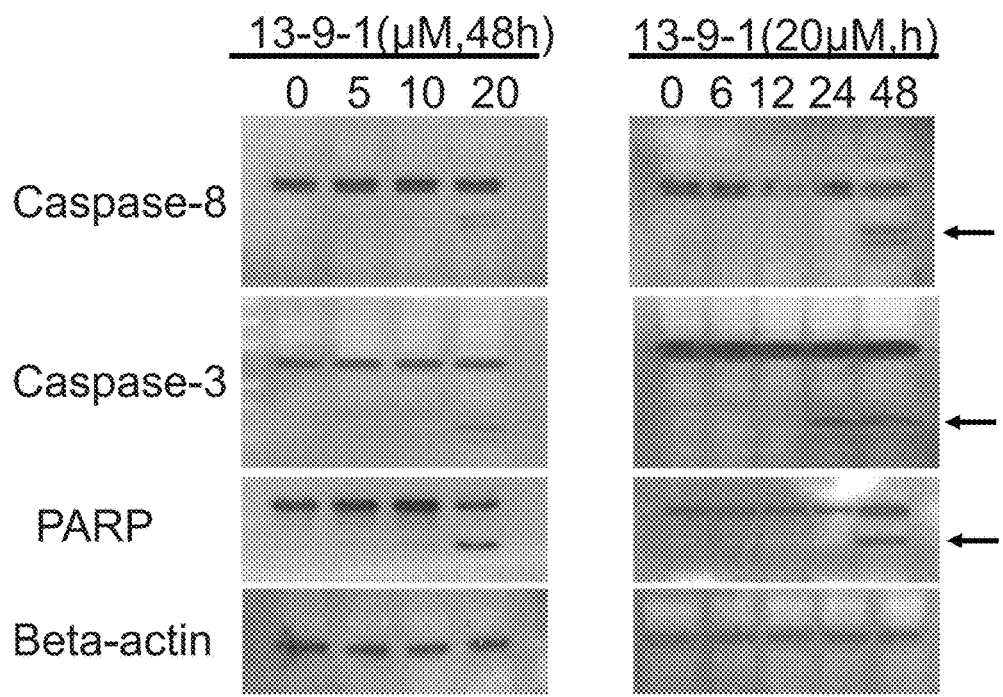

FIG. 12. Cleavage of Caspase-3, Caspase-8, and PARP confirms that de-ethylflavopereirine induces apoptosis in PANC-1 pancreatic cancer cells. Beta-actin was used as a control. The effect is dose- and time-dependent. Left panel shows results at 0, 5 μM, 10 μM, and 20 μM of compound for the same amount of time (48 hours); right panel shows results for 0, 6 hours, 12 hours, 24 hours, and 48 hours at the same concentration of compound (20 μM).

Figure 13:
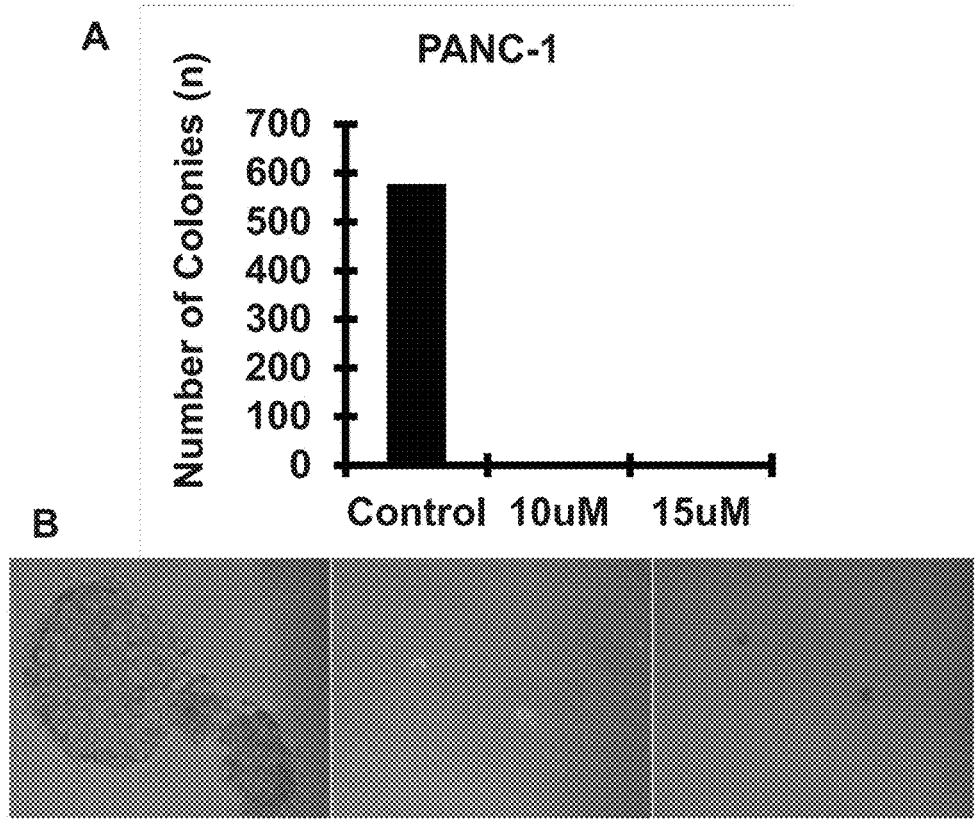

FIG. 13. Colony formation in soft agar of PANC-1 pancreatic cancer cells with or without de-ethylflavopereirine treatment. De-ethylflavopereirine completely inhibited colony formation by tumorigenic cancer cells at 10 μM or 15 μM concentration.

Figure 14:
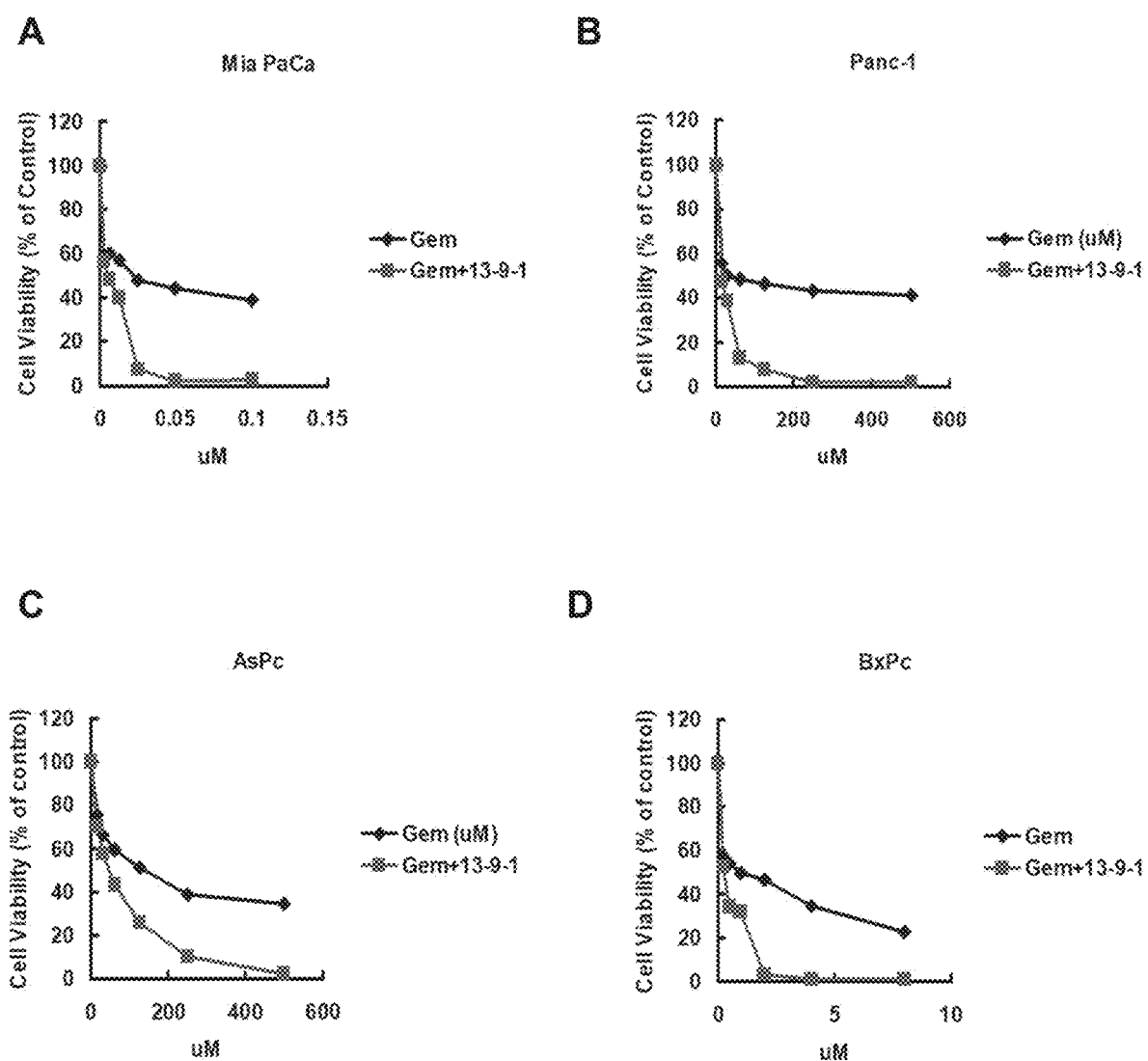

FIG. 14. Growth inhibition of pancreatic cancer cells treated with gemcitabine (Gem) alone compared to combination treatment with gemcitabine plus de-ethylflavopereirine (Gem+13-9-1). Pancreatic cancer cell lines MIA PaCa (upper left), PANC-1 (upper right), AsPc (lower left), and BxPc (lower right) showed some resistance to gemcitabine (lozenges) as shown by the top curve in each dose-response plot. The combination of gemcitabine and de-ethylflavopereirine (squares) provided close to 100% cytotoxic effect on the cancer cells as shown by the bottom curve in each dose-response plot regardless of their variable resistance to gemcitabine alone.

Figure 15:
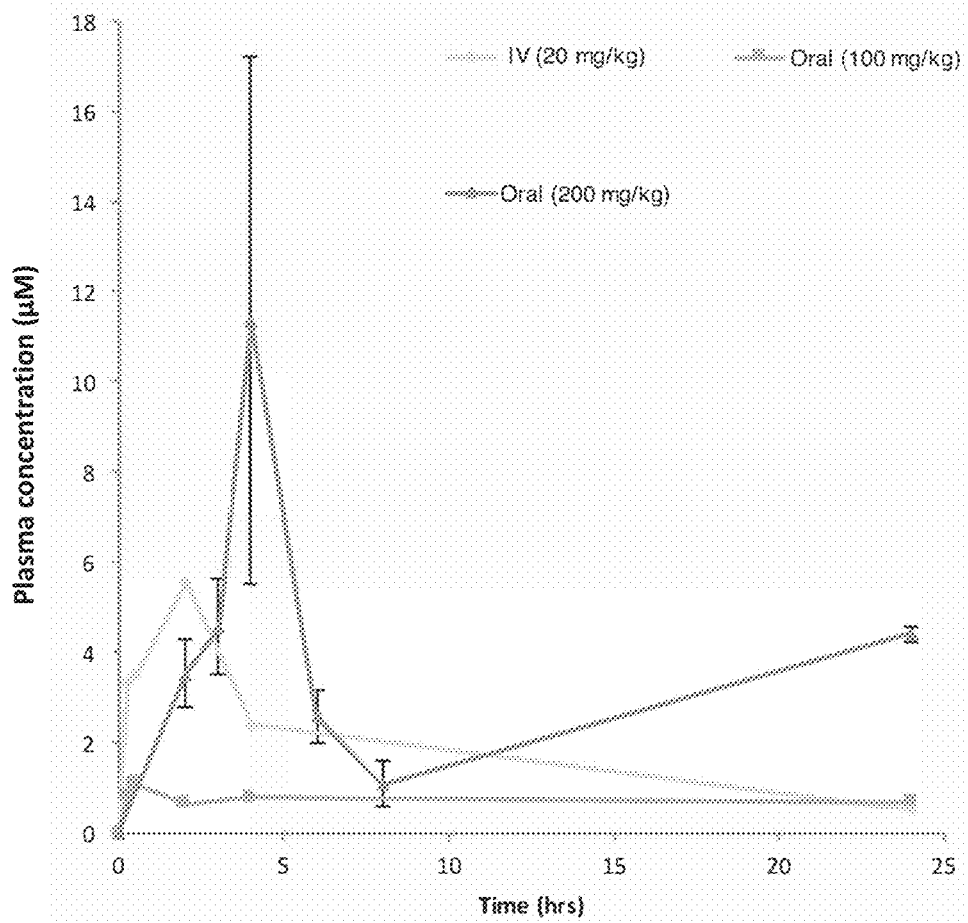

FIG. 15. Plasma concentrations of de-ethylflavopereirine following intravenous or oral administration: intravenous at 20 mg/kg (lozenges) having a peak at approximately 2 hours, oral at 100 mg/kg (squares), or oral at 200 mg/kg (triangles) having a peak at approximately 4 hours.

FIG. 16. Animal Study. PANC-1 cells with luciferase gene were orthotopically implanted into the pancreas of nude mice and the tumors were monitored by live-animal imaging. Longitudinal tumor growth shown by quantification of all images in the treated group (lozenges, n=9) and the untreated group (squares, n=10). Tumor burden is represented by average total photon flux (top) and its log transform (bottom).

Figure 17:
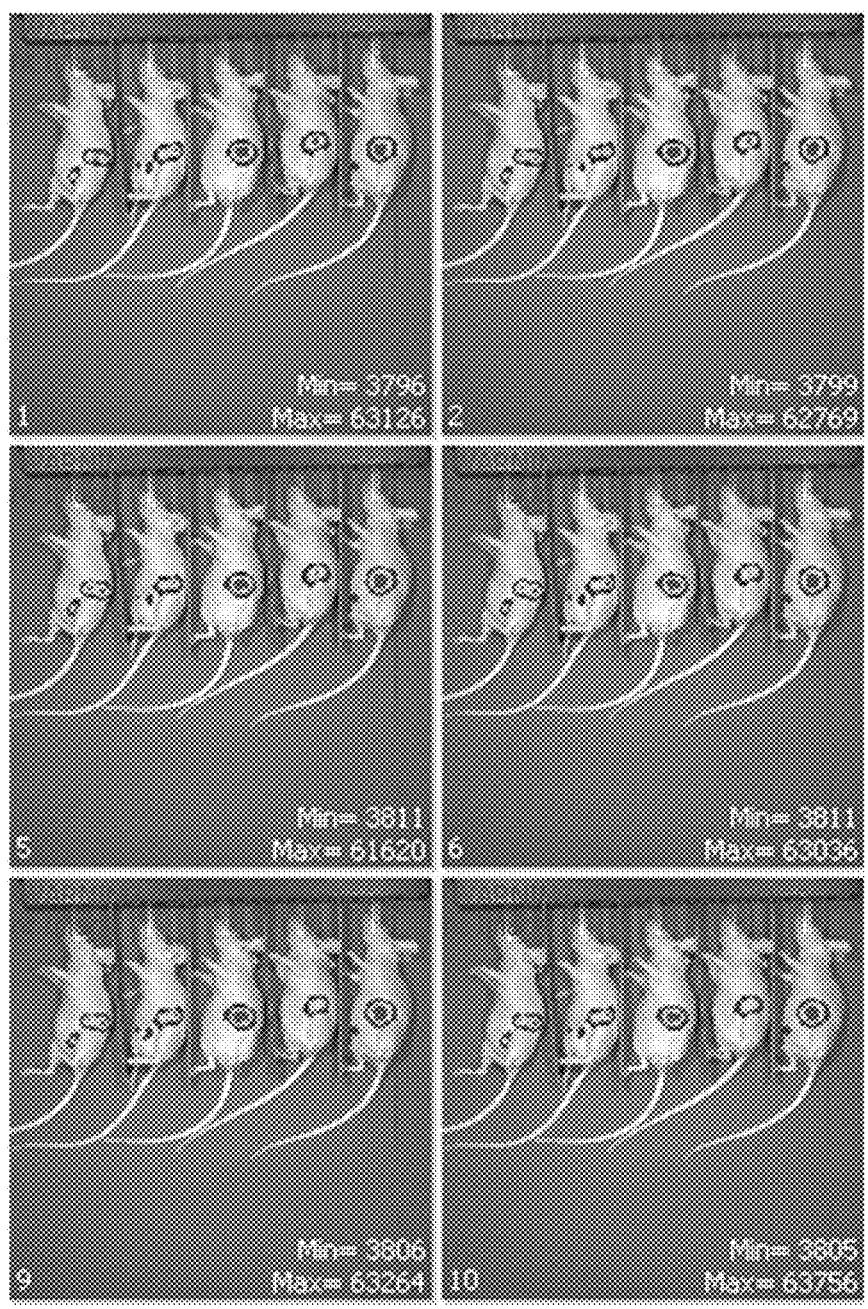

FIG. 17. Untreated animals. PANC-1 cells with luciferase gene were orthotopically implanted into the pancreas of six nude mice, and the tumors were monitored by luminescence imaging.

Figure 18:
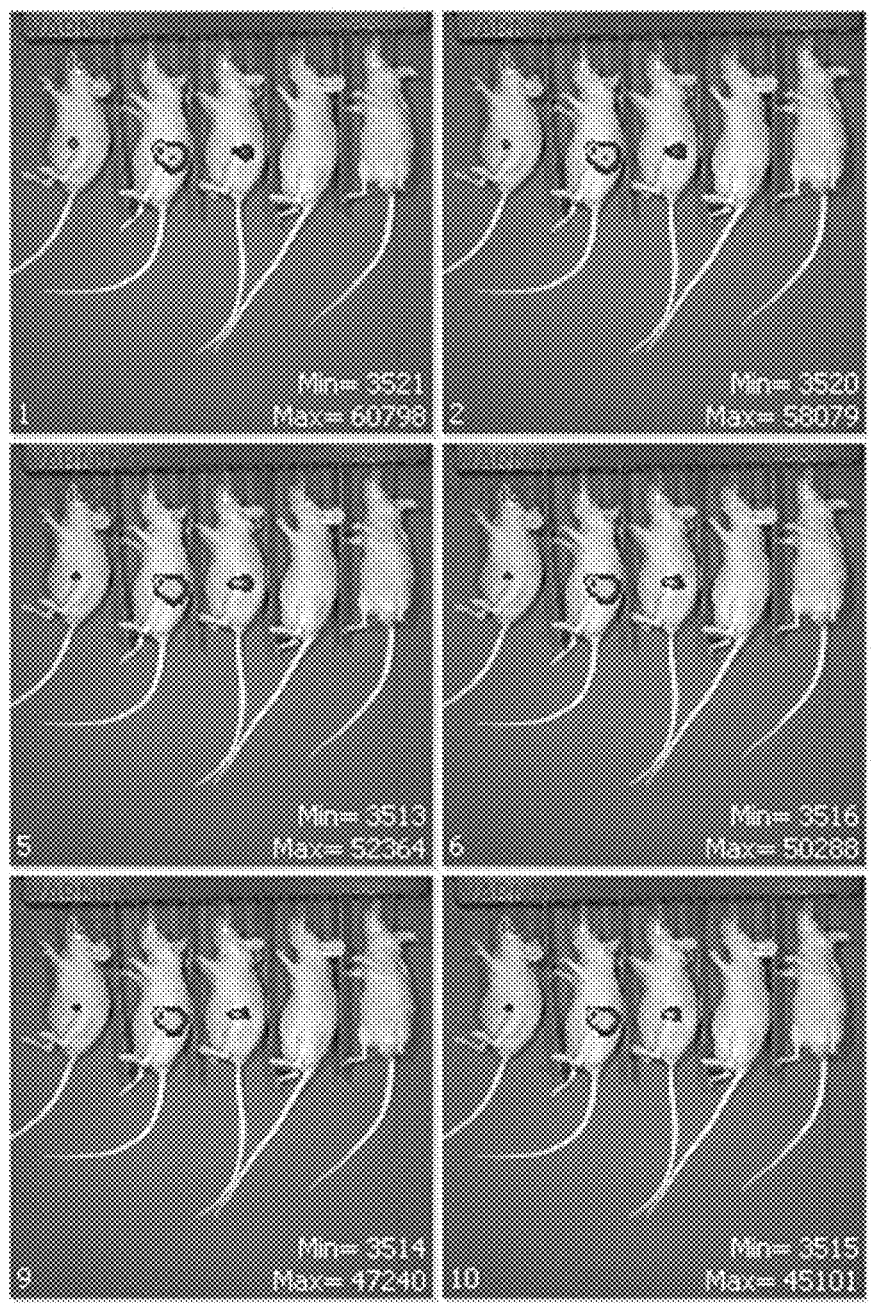

FIG. 18. Animals treated with de-ethylflavopereirine. PANC-1 cells with luciferase gene were orthotopically implanted into the pancreas of six nude mice, and the tumors were monitored by luminescence imaging.

Figure 19:
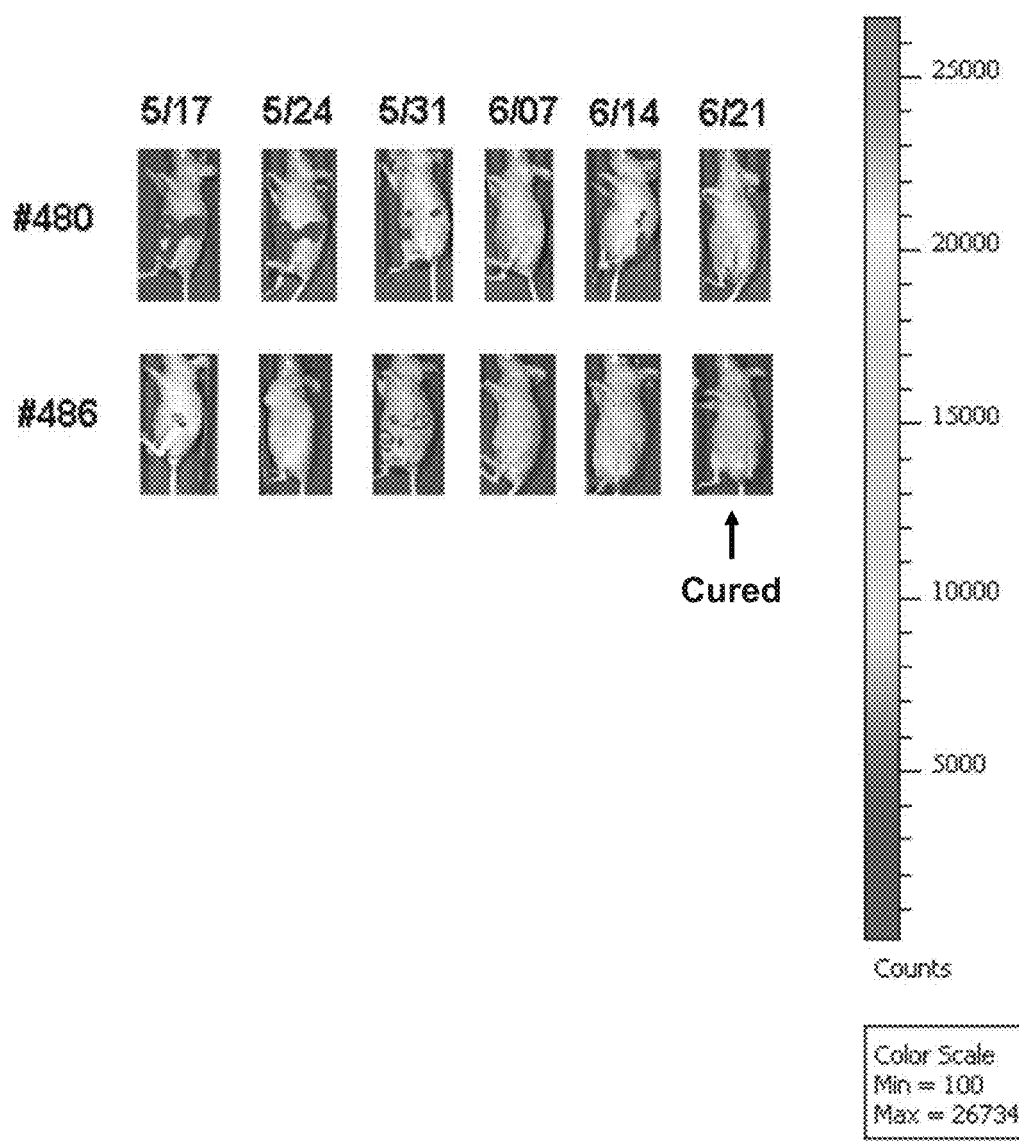

FIG. 19. Bioluminescence imaging of PANC-1 tumors in nude mouse #480 or #486 abolished by treatment with de-ethylflavopereirine. Thus, two of 21 animals were free of tumor (labeled "cured"). Images at weekly intervals are shown for each animal.

FIG. 20. Final PANC-1 tumor weights at necropsy in treated or untreated animals: average weights shown at left and individual weights shown at right (FIG. 20A). Final metastatic lesions count at necropsy in treated and untreated animals (FIG. 20B): percentage of mice with metastatic lesions at left and number of metastatic lesions at right.

Figure 21:
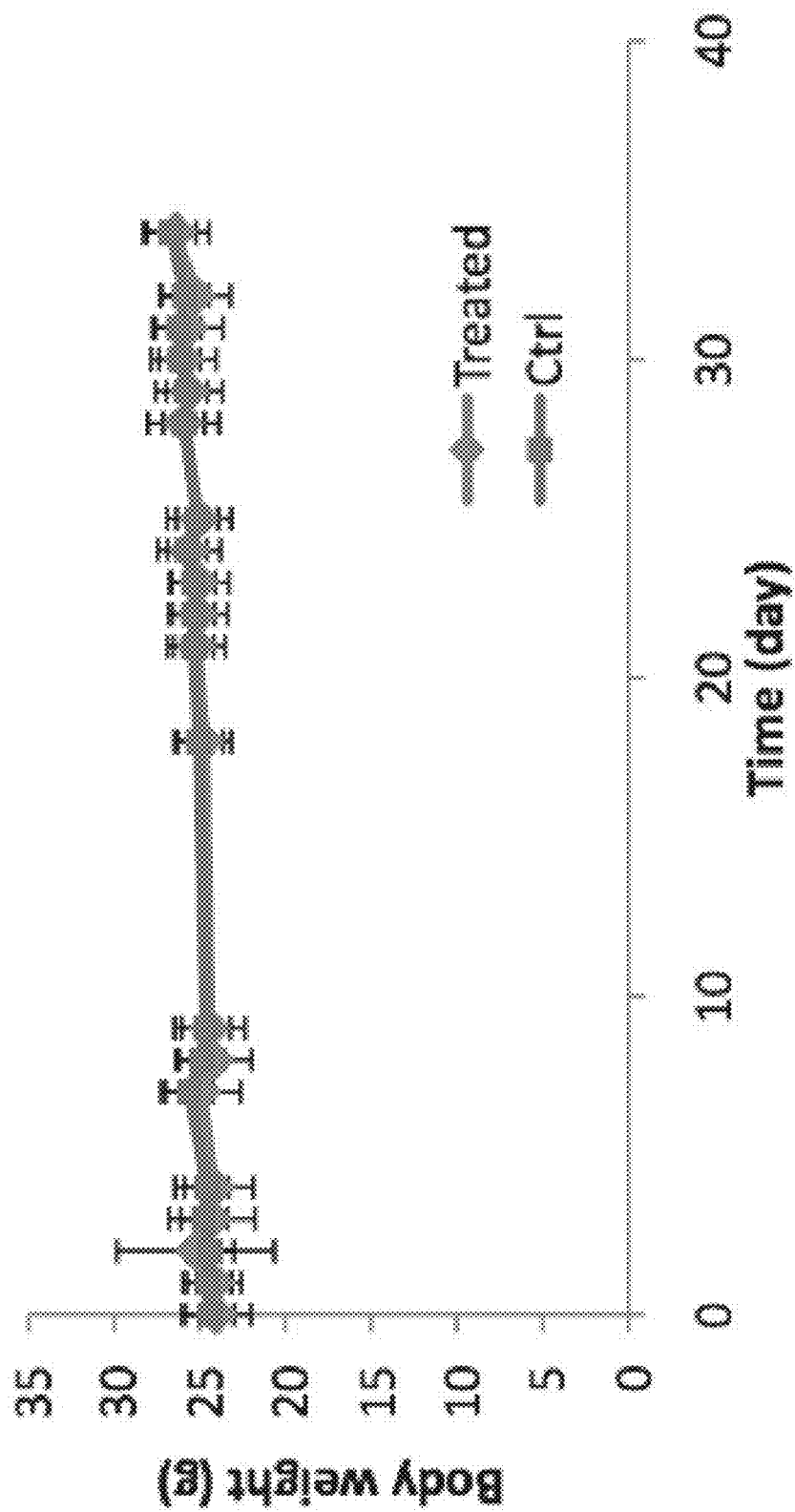

FIG. 21. Average body weight of mice bearing orthotopic PANC-1 tumors on day 0 through day 40 were not treated (squares) or treated with de-ethylflavopereirine (lozenges). Weights of mice in the control group and the treated group were indistinguishable.

Anti-Pancreatic Cancer Stem Cell Activity of De-Ethylflavopereirine

Figure 22:
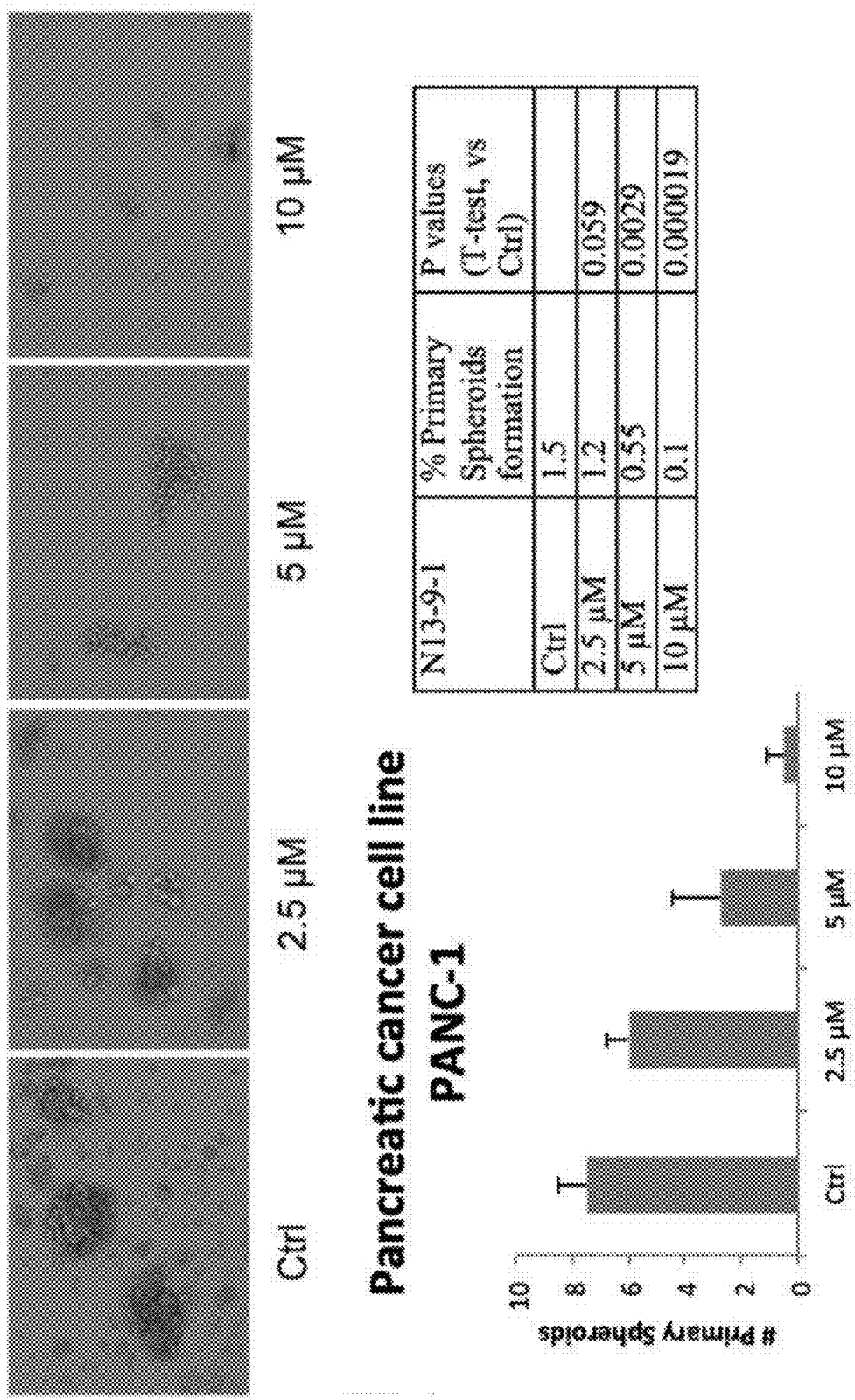

FIG. 22. PANC-1 cell suspensions were treated at concentrations of 0 μM (negative control), 2.5 μM, 5.0 μM, and 10.0 μM de-ethylflavopereirine then examined for the presence of spheroids. In this first round of treatment, the 5 μM and 10 μM concentrations significantly inhibited primary spheroid formation as shown by the bars in the graph and P values in the table beneath the images.

Figure 23:
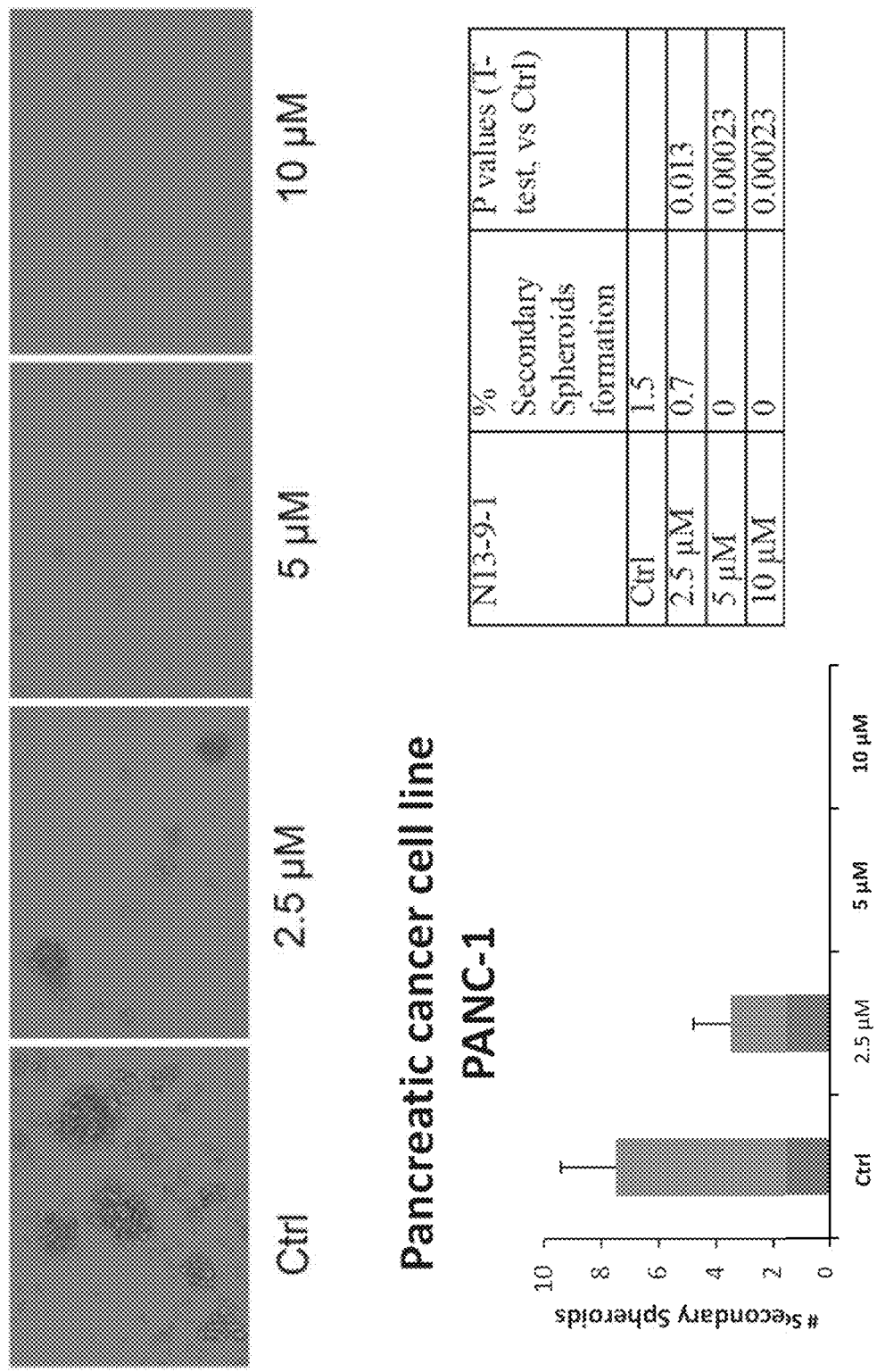

FIG. 23. Primary spheroids from first round were collected and seeded for secondary spheroid formation. Following treatment with concentrations of 0 μM (negative control), 2.5 μM, 5.0 μM, and 10.0 μM de-ethylflavopereirine, suspensions were examined. Formation of secondary spheroids was completely inhibited by the 5 μM and 10 μM treatments, while the 2.5 μM treatment showed significant inhibition as shown by the bars in the graph and P values in the table beneath the images.

FIG. 24. De-ethylflavopereirine decreased the percentage of cancer stem cells in a pancreatic cancer cell population (24 hours). The panels show CD44 (PE-Cy7) positive and EpCam (APC) positive cells in the CD24 (PE) gate at concentrations of 0 μM (upper left), 2.5 μM (upper right), 5 μM (lower left), and 10 μM (lower right) de-ethylflavopereirine after 24 hr. "Q1"=CD24$^+$/CD44$^+$, "Triple+"=CD24$^+$/CD44$^+$/EpCam$^+$, "Q3"=CD24$^+$, and "Q4"=CD24$^+$/EpCam$^+$. At 24 hr post-treatment, de-ethylflavopereirine reduced the CD24$^+$/CD44$^+$/EpCam$^+$ cell population in PANC-1 cells. The bar graph (bottom) shows the percentage of triple-positive cells in the bulk cell population following exposure to 0, 2.5 μM, 5 μM, and 10 μM of de-ethylflavopereirine.

Figure 25:
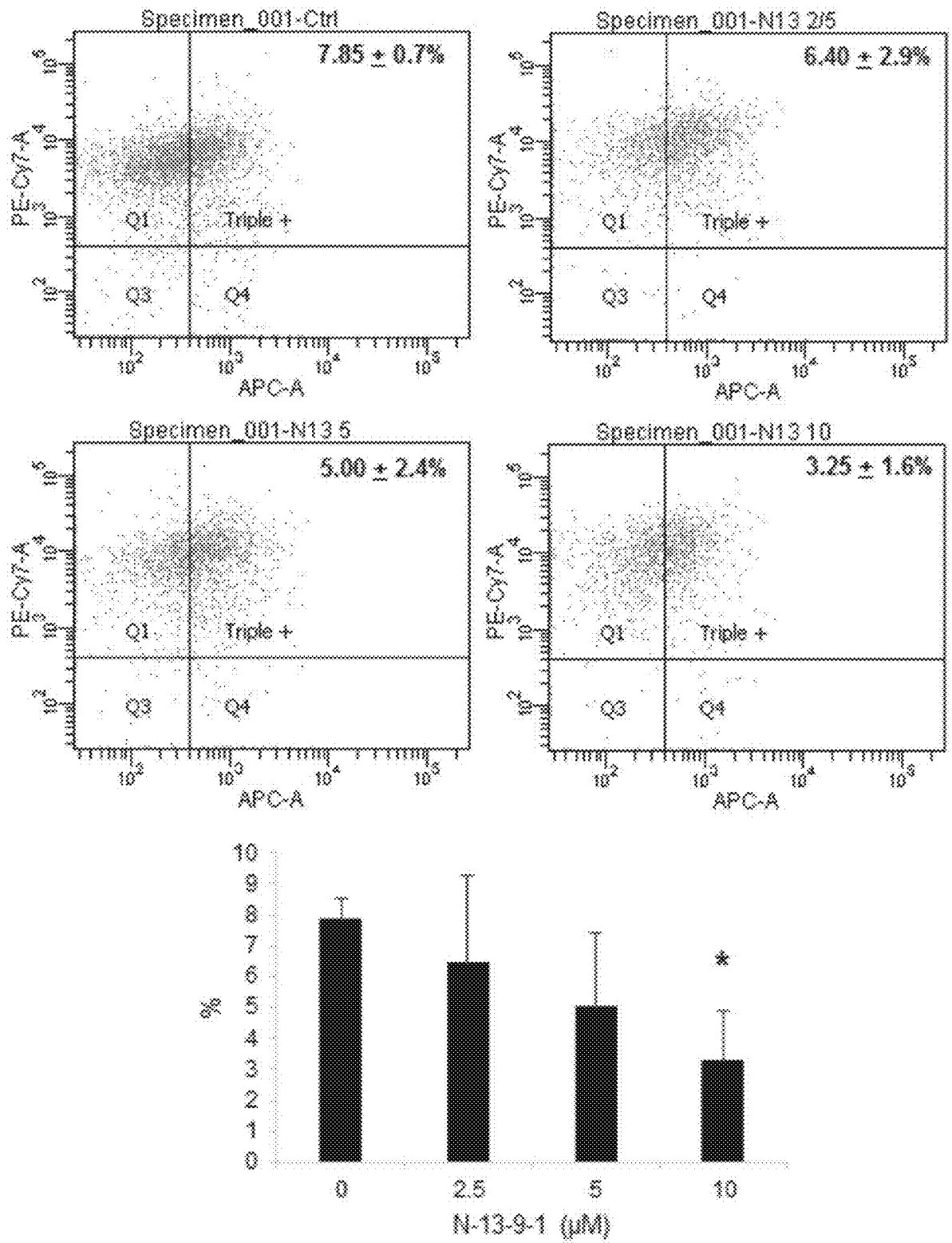

FIG. 25. De-ethylflavopereirine decreased the percentage of cancer stem cells in a pancreatic cancer cell population (48 hours). The panels show CD44 (PE-Cy7) positive and EpCam (APC) positive cells in the CD24 (PE) gate at concentrations of 0 μM (upper left), 2.5 μM (upper right), 5 μM (lower left), and 10 μM (lower right) de-ethylflavopereirine after 48 hr. "Q1"=CD24$^+$/CD44$^+$, "Triple+"=CD24$^+$/CD44$^+$/EpCam$^+$, "Q3"=CD24$^+$, and "Q4"=CD24$^+$/EpCam$^+$. At 48 hr post-treatment, compound 13-9-1 reduced the CD24$^+$/CD44$^+$/EpCam$^+$ cell population in PANC-1 cells. The bar graph (bottom) shows the percentage of triple-positive cells in the bulk cell population after exposure to de-ethylflavopereirine. Results for 10 μM of de-ethylflavopereirine are statistically significant (*P<0.05 by Student's t-test).

FIG. 26. Effect of de-ethylflavopereirine on pancreatic cancer formation and growth. FIG. 26A shows the rate of tumor formation (left) and tumor growth (right) after 1×10$^6$ PANC-1 cells were inoculated. In the control group (top line of left graph), 86.67% (13/15) of the untreated mice formed tumors. Compound 13-9-1 (10 μM) decreased the rate to 80% (4/5); there was no effect on the time of tumor formation (bottom line of left graph). Compound 13-9-1 reduced the growth of tumors formed by inoculation of 1×10$^6$ PANC-1 cells in treated mice (bottom line of right graph) compared to tumor growth in untreated mice of the control group (top line of right graph) significantly (P=0.04). After inoculation of 2×10$^5$ PANC-1 cells, FIG. 26B shows they were significantly inhibited by compound 13-9-1. In the control group (top line of left graph), 80% (12/15) of the untreated mice formed tumors. Compound 13-9-1 (10 μM) decreased the tumor formation rate to 60% (3/5); this indicated reduction in tumor formation initiated by pancreatic cancer stem cells (bottom line of left graph). Also, the single-dose treatment of compound 13-9-1 (10 μM) reduced the growth of tumors formed. Tumor volume increased in untreated mice of the control group (top line of right graph) while compound 13-9-1 in significantly reduced tumor growth in treated mice (bottom line of right graph) (P=0.02). In FIG. 26C, after 2×10$^4$ PANC-1 cells were inoculated, 20% of the mice formed tumors in both the control group (3/15) and the treated group (1/5) at 38 days of observation.

The growth of tumors in treated mice was not significantly different from that of untreated mice.

Figure 27:
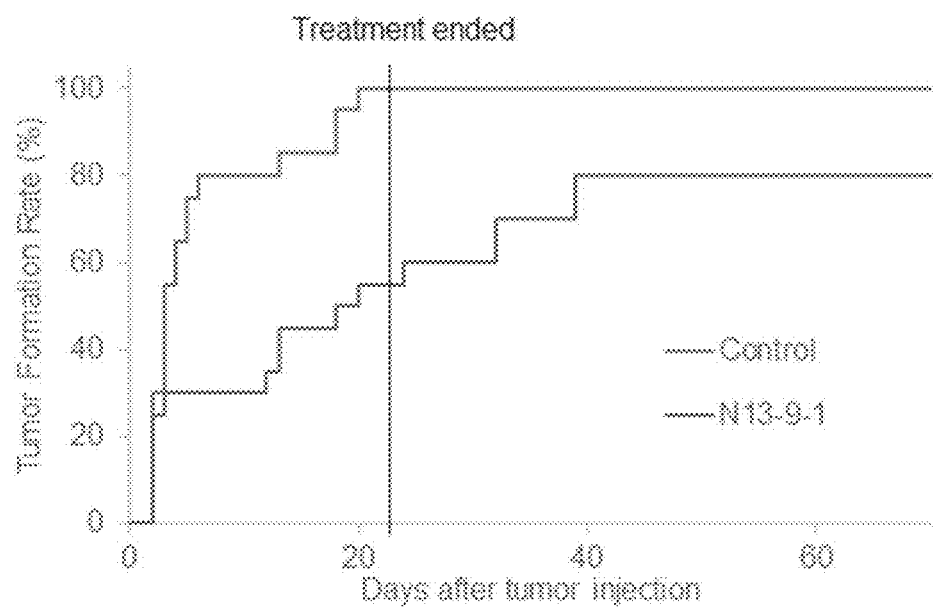

FIG. 27. Reduction of tumor formation by de-ethylflavopereirine. Compound 13-9-1 reduced tumor formation of PANC-1 cancer stem cells. After $2\times10^5$ of untreated PANC-1 cells were inoculated, 100% (20/20) tumor formation was observed for the control group (solid top line) at Day 20. Only 55% tumor formation was observed for the treatment group (dashed bottom line) at Day 20 when the inoculated PANC-1 cells were pre-treated with compound 13-9-1. The maximum tumor formation rate in the treatment group reached 80% at Day 39, which was highly significantly different compared to the control group ($P<0.001$ by log-rank test).

Figure 28:
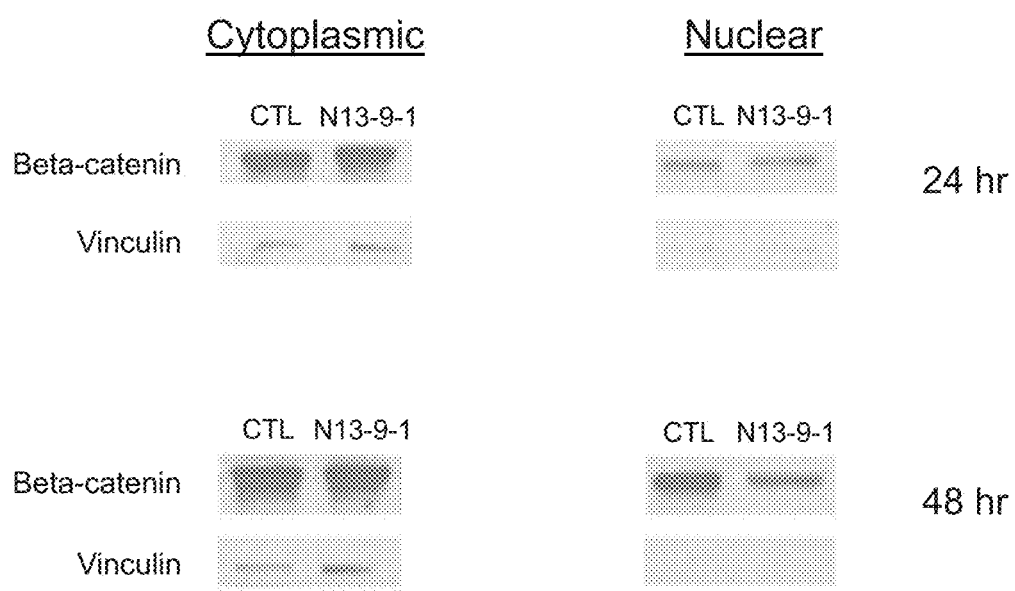

FIG. 28. Effect of de-ethylflavopereirine on β-catenin localization in the nucleus of PANC-1 cells. At 24 hr post-treatment, compound 13-9-1 showed no effect on β-catenin levels in the nucleus of PANC-1 pancreatic cancer cells. At 48 hr post-treatment, compound 13-9-1 significantly reduced β-catenin levels in the nucleus. Cytoplasmic β-catenin levels were not affected under these conditions. Vinculin provided a marker for a cytoplasmic protein that is present in very low amounts in the nucleus.

Anti-Inflammatory Effect of De-Ethylflavopereirine Reduces Pancreatitis and Subsequent Development of Pancreatic Cancer FIG. 29. Effects of de-ethylflavopereirine in a mice model of alcohol-induced chronic pancreatitis. Paraffin sections of the pancreas were stained with hematoxylin and eosin. FIG. 29A shows normal tissue (left panel), edema and infiltration of inflammatory cells in mice given ethanol (center panel), and no tissue damage in mice given ethanol and compound 13-9-1 (right panel). This tissue protection was quantitated with an injury score (FIG. 29B). Ly6G was elevated four-fold in the pancreas of mice given ethanol while the number of neutrophils was not elevated in mice given ethanol and compound 13-9-1 (FIG. 29C).

Anti-Colon Cancer Activity of De-Ethylflavopereirine

Figure 30:
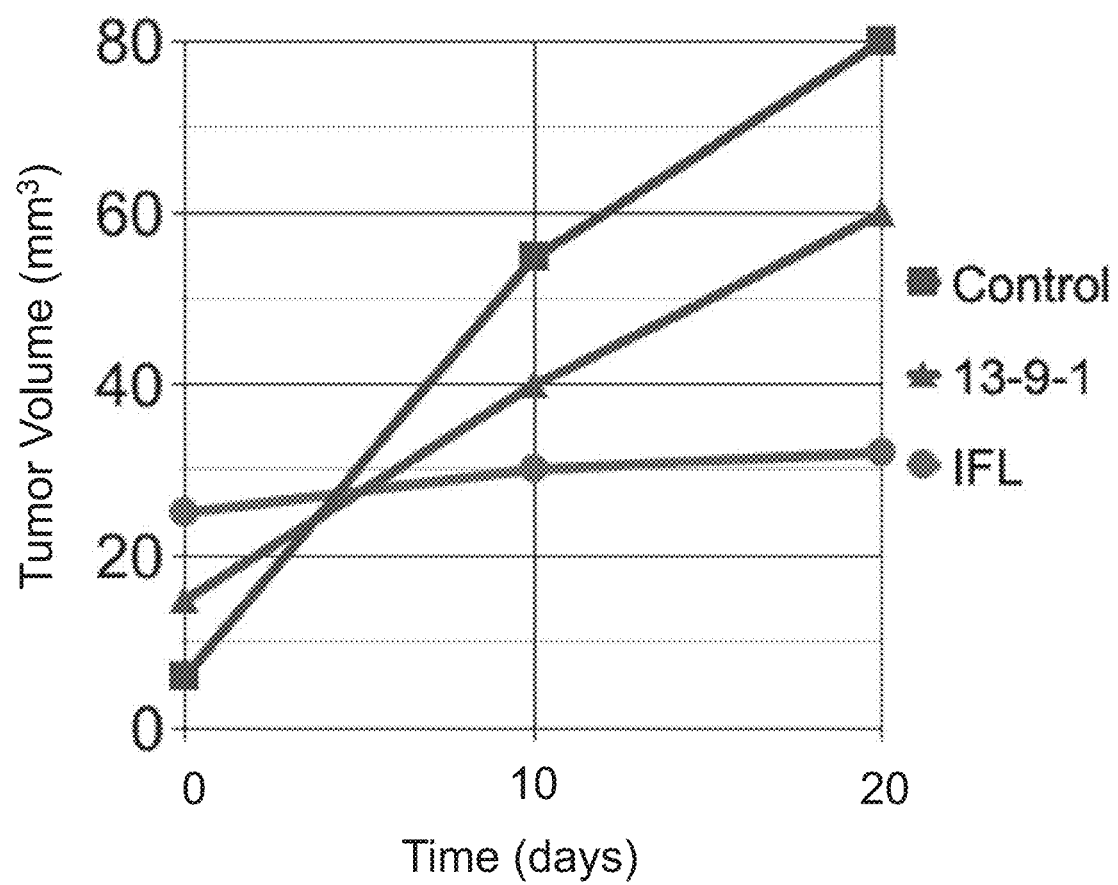

FIG. 30. Effect of de-ethylflavopereirine on HT-29 colon cancer tumor volume. Nude mice with subcutaneous xenografts of human HT-29 colon cancer cells were grouped as untreated control (squares), administered compound 13-9-1 (triangles), or administered IFL as conventional chemotherapy regimen (circles). IFL is a combination of irinotecan, fluorouracil, and leucovorin often used for treatment of colorectal cancer. The graph shows tumor volumes ($mm^3$) plotted against time in days. Animals were treated for two and a half weeks. The experiment was stopped then because animals in the IFL group started to die at two and a half weeks. No animals treated with compound 13-9-1 died.

Figure 31:
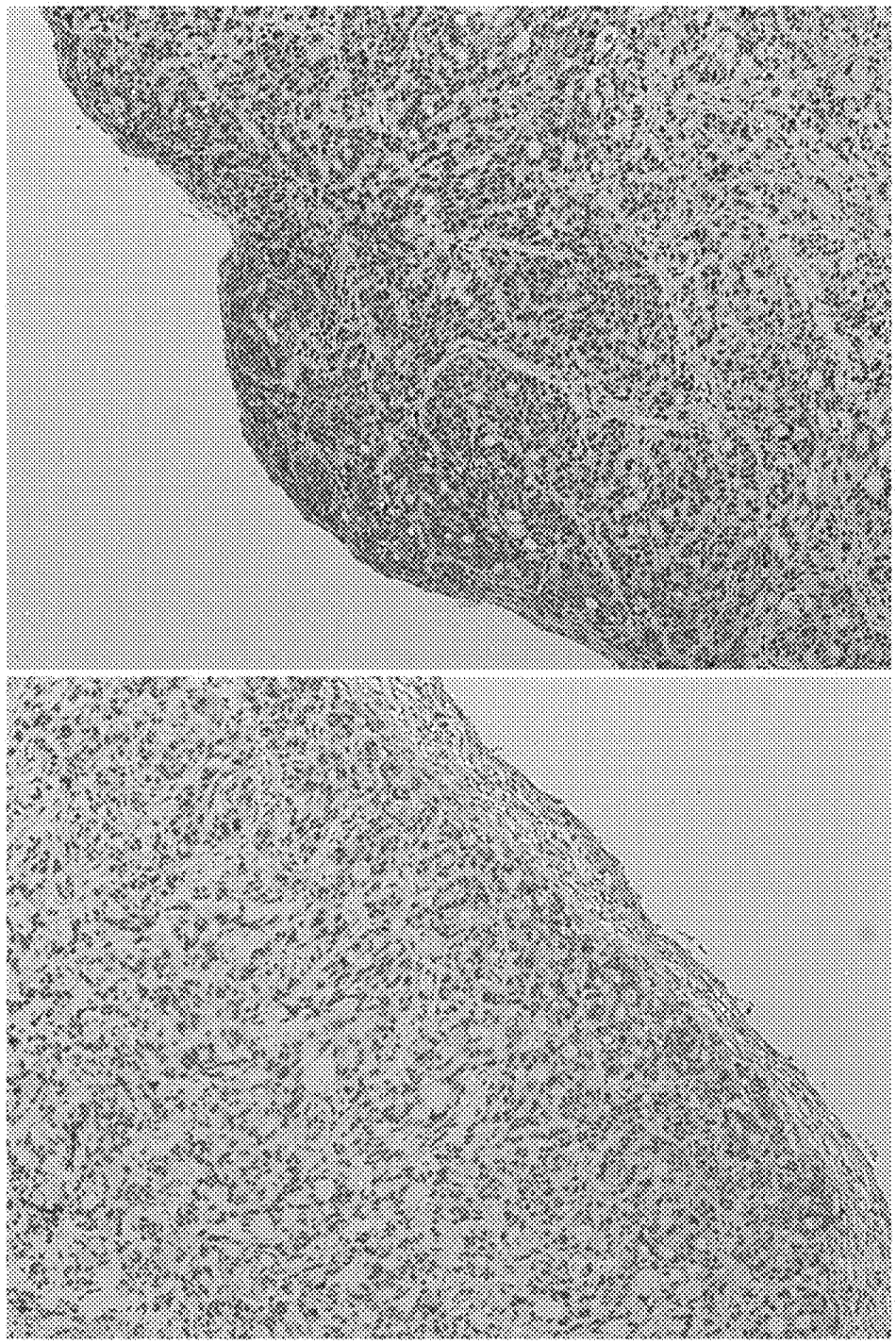
Figure 32:
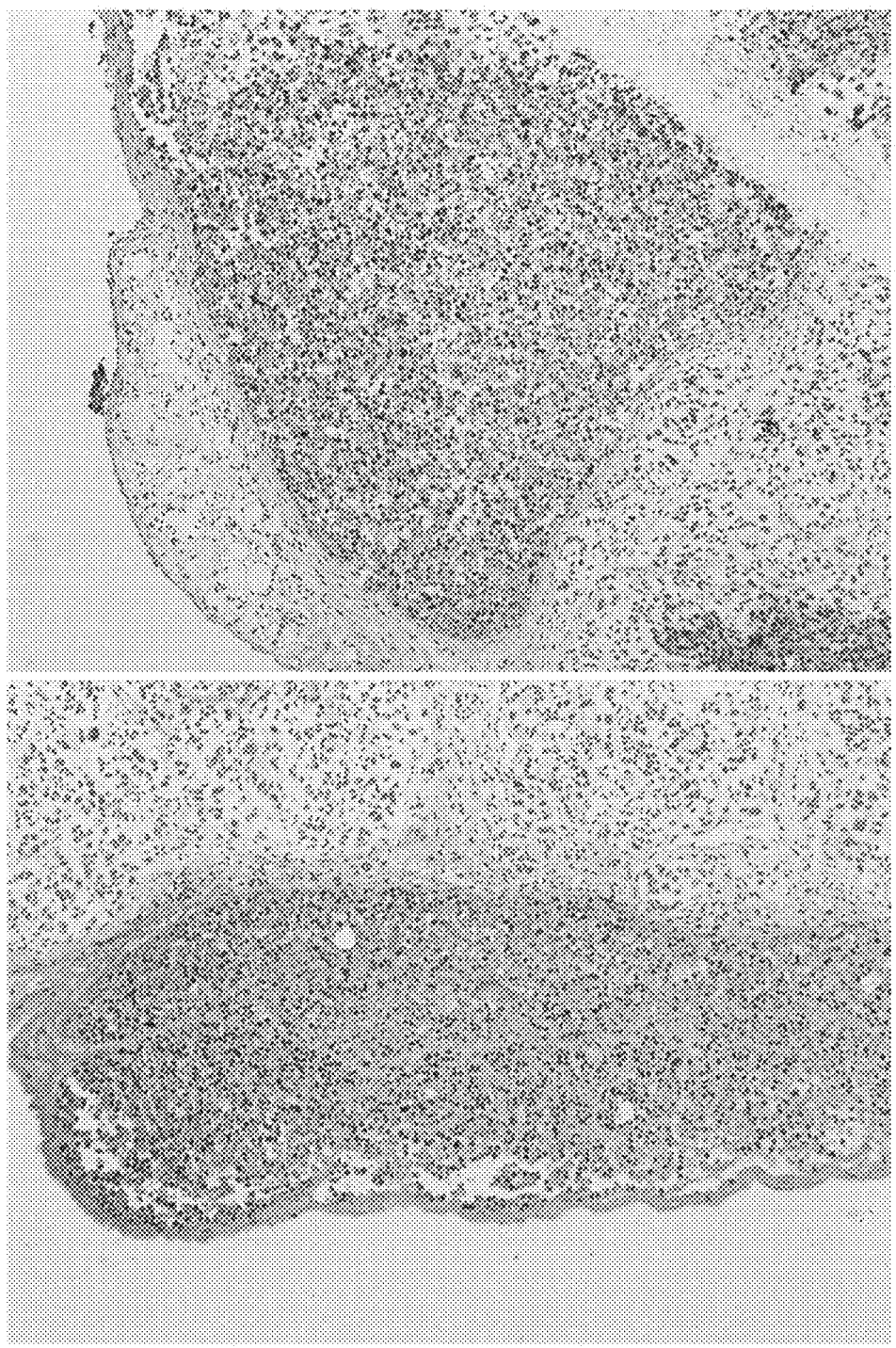
Figure 33:
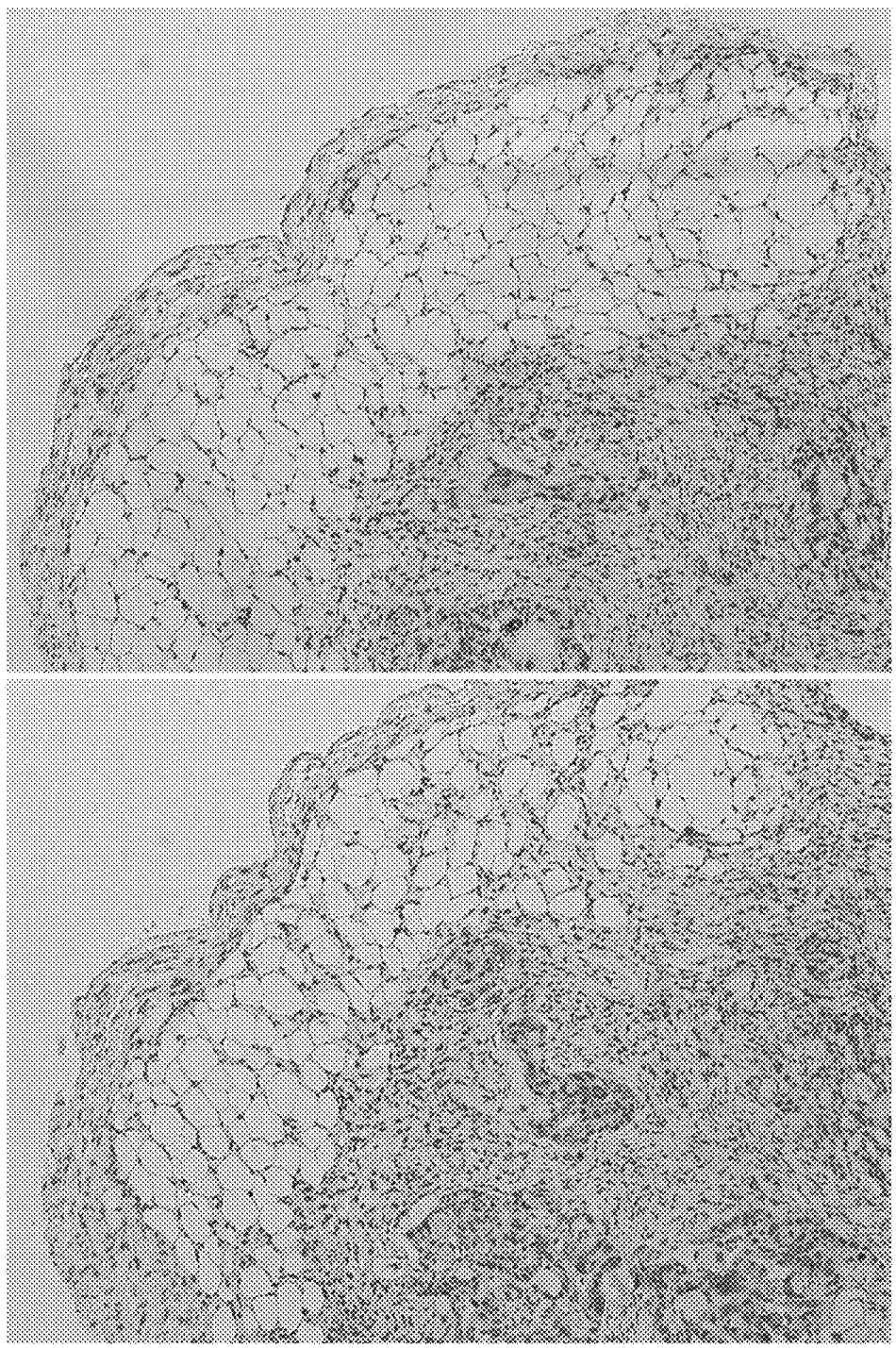

FIGS. 31 to 33 show TUNEL staining of HT-29 tumors removed from untreated mice (control) in FIG. 31, mice administered de-ethylflavopereirine in FIG. 32, or mice administered IFL in FIG. 33. Each of the FIGS. 31-33 shows two independent samples (top and bottom) from each treatment. After treatments were concluded, tumors were removed from the animals, fixed, thin sectioned, and stained by the TUNEL method to identify cells undergoing apoptosis. In FIG. 31, the borders of tumors from control animals show intact tissue and the absence of TUNEL staining. In FIG. 32, the borders of tumors from animals administered 13-9-1 show there was apoptosis in zones near the periphery of the tumors. The sample at FIG. 32 (top) also shows a region adjacent to the edge at the lower left of the tumor tissue that was destroyed following apoptosis of the cells. The color images clearly distinguish the dark purple/brown color of cells undergoing apoptotis from the blue color of intact tumor cells. In FIG. 33, borders of tumors from animals treated with IFL show that significant zones of tissue at the periphery were completely destroyed.

DETAILED DESCRIPTION OF SPECIFIC EMBODIMENTS

Carcinogenesis is understood to be a multistep process. Thus, targeting early times and events in the development of dysregulated proliferation was an objective of the present invention because of the difficulty of eliminating residual disease or cancer stem cells, especially in a cancer's advanced stages when cytotoxic agents are less or no longer effective. For this reason, we believe de-ethylflavopereirine and its derivatives as described herein may provide therapy (e.g., simultaneously in a drug cocktail) that complements another chemotherapeutic agent by having them target different aspects of cancer cell metabolism, sensitizing cancer cells to the other chemotherapeutic agent's activity, permitting the effective use of a lower dose of the other chemotherapeutic agent to lessen one or more of its undesirable side effects, extending the usefulness of another chemotherapeutic agent that has lost its effectiveness in an advanced cancer, or any combination thereof.

Development of the cancer cell phenotype follows DNA destabilization, which can be targeted by de-ethylflavopereirine. For example, a carcinogen changes normal DNA structures long before a tumor is observed. Malins et al. showed that detection of structural changes in DNA of prostate cells can distinguish normal tissue, benign prostatic hyperplasia (BPH), and adenocarcinoma caused by alterations in their deoxyribose and phosphodiester structures (*Proc. Nat'l Acad. Sci. USA* 94:259-264, 1997). Progression of normal cells to BPH or adenocarcinoma may be tracked with the same structural modifications in DNA. They also showed in sarcoma that a known carcinogen produced structural changes in the nucleotide bases and the phosphodiester backbone of cellular DNA (*Proc. Nat'l Acad. Sci. USA* 101:10721-10725, 2004). The effect of this chemical DNA damage on the hydrogen bonds that stabilize the DNA double helix was originally shown in an indirect assay for carcinogens (Beljanski, *IRCS Med. Sci. Biochem.* 7:476, 1979). The synthetic compound described herein can delay or reduce the rate of tumor formation by specifically targeting cells with destabilized DNA and inducing apoptosis therein.

Without being bound to a particular mechanism of action, de-ethylflavopereirine and its derivatives may be effective as anti-cancer agents at an early step of carcinogenesis by blocking proliferation of cells, for example, at an early stage of the DNA destabilization process. Given the lack of toxicity, even at high doses, it may be possible to administer de-ethylflavopereirine and its derivatives to a subject at high or elevated risk for cancer, such as exposed to a mutagen, carcinogen, or other environmental hazard; bearing an inherited mutation in a proto-oncogene or tumor suppressor gene, DNA damage response, or DNA repair machinery; or having precancerous lesions detected by cancer screening for whom treatments with serious side effects are not warranted. A similar use of low-dose acetylsalicylic acid for primary prevention of cardiovascular disease (CVD) and colon cancer in certain people having high CVD risk (*Ann. Intern. Med.* 164:836-845; see also *JAMA Oncol.* 2:762-769, 2016), presumably by inhibiting long-term effects of inflammation, has been recommended by the U.S. Preventive Services Task Force. There is also weaker support for decreasing risks for ovarian cancer (*J. Nat'l Cancer Inst.* 106:djt431, 2014), pancreatic cancer (*Cancer Epidemol. Biomarkers Prev.* 26:68-74, 2017), and others such as gastric, esophageal, endometrial, breast, and prostate cancers (*BMC Cancer* 18:288, 2018).

Because such DNA destabilization is a continuing pathologic process throughout carcinogenesis, the present invention is effective (as shown in the examples herein) throughout the different stages of cancer progression. One possibility is that compounds of the present invention can target cells containing destabilized DNA (cf. *PLOS Genet.* 11:e1004901, 2015) and induce apoptosis in them (cf. *J. Cell Biochem.* 117:279-288, 2016) more effectively than existing cancer protocols.

Cell-based assays showed that the synthetic compound selectively inhibited the growth of cancer cells in a dose dependent manner. The synthetic compound appeared to act selectively against cancer cells by causing their destruction without harming noncancerous cells. In vitro and in vivo studies demonstrated that de-ethylflavopereirine also destroyed the cancer stem cells that enable the persistence and recurrence of malignancies even after tumor volumes have been reduced by anti-cancer therapy.

In preclinical studies using mice xenografted with human pancreatic or colon cancer cells, the synthetic compound shrank tumors significantly, sometimes completely eradicating them. It also inhibited the appearance of metastases, but caused no detectable toxicity in the animals as shown by their normal weight gain and normal histology of their internal organs.

De-ethylflavopereirine may be administered enterally or parenterally (preferably orally, intravenously, or by infusion), and appeared to be well-tolerated over a broad range of doses. At similar or lower concentrations, it was as active against cancer cells as the natural compound (flavopereirine) it is structurally related to, but de-ethylflavopereirine was less toxic. Thus, while removal of the ethyl group from flavopereirine did not alter its anti-tumor activity, toxicity may be significantly reduced. Unlike flavopereirine, de-ethylflavopereirine can be administered in oral doses of hundreds of milligrams per kilogram of a subject's mass without noticeable toxicity. Thus, as a solution to the problem of having to limit the dose of flavopereirine, de-ethylflavopereirine can be a more effective anti-cancer agent than flavopereirine because higher systemic concentrations can be achieved albeit the chemical modification does not significantly increase activity.

In the context of enteral administration, encapsulating the pharmaceutical composition may be used to protect de-ethylflavopereirine from degradation by acid or enzymes encountered in the digestive tract and/or to enhance de-ethylflavopereirine absorption into the systemic circulation. The advantage of administering a liposomal composition may be shown by comparing the circulating amount of de-ethylflavopereirine or a metabolite thereof.

De-ethylflavopereirine and its salts, in solution or solid form, answer the need for chemotherapeutic agents that are safe and effective. The physiological effects of de-ethylflavopereirine appeared to be selective: it could selectively target cancer cells for elimination (e.g., apoptosis or killing by external actors), but did not noticeably interfere with the viability of noncancerous cells, including those that are rapidly dividing. De-ethylflavopereirine was also effective when combined with other chemotherapeutic drugs. Such combinations were synergistic, and triggered cell death in cancer cells (including cells that have become drug resistant). Because of its unique mechanism and broad spectrum of useful effects, de-ethylflavopereirine will become an anchor compound in a new generation of chemotherapeutic combinations that enhance the efficacy of cancer therapy and reduce harm to a subject receiving the compound, its pharmaceutically acceptable salt, a solvate (e.g., hydrate), or a pharmaceutically acceptable salt of a solvate or a hydrate.

Definitions

Unless defined otherwise herein, technical terms have the same meaning as would be understood by a person skilled in the arts related to the invention (i.e., an oncologist or other cancer specialist). Depending on the specific technology, such person may also have knowledge, training, and experience in medicinal chemistry and/or pharmacology.

As used in the specification and claims, the term "a" includes the singular and plural forms of its nouns unless either is contrary to the context in which the term is used. For example, a compound may be one or more compounds while a compound of Formula (I) means de-ethylflavopereirine.

When ranges are used herein for physical properties, such as molecular weight, or chemical properties, such as chemical formulae, all combinations and subcombinations of ranges and specific embodiments therein are intended to be included. As used herein, the term "about" or the symbol "~" when used in the context of a numeric value or range thereof means that the value or range may deviate by an amount deemed reasonable under the circumstances by a person skilled in the art, e.g., within the variability of measurement or observation (or within experimental error). Alternatively, the numeric value or range can vary by 10% of the stated value or range. For example, "about 23° C." can mean a temperature in the range from 22° C. to 24° C. for the observed variation in a thermometer's readings or, alternatively, 23° C.±2.3° C.

The term "an agent" refers to one or more biologic or chemical compounds. Nonlimiting examples include a small (less than 1000 Da) organic or inorganic molecule, an oligopeptide (20 or fewer amino acids), a mimetic thereof, a polypeptide (including, but not limited to, antibodies, enzymes, soluble receptors, or ligands thereof), an oligonucleotide (50 or fewer nucleotides), an aptamer thereof, or a polynucleotide. An agent can be synthesized or obtained from a natural source, such as plant or animal extracts, and the like. An agent other than a compound of the present invention may be termed "another agent" or "a second agent" hereinafter.

The term "anti-cancer agent" or "anti-tumor agent" refers to an agent useful in the treatment of cancer, a malignant tumor, or another neoplastic condition. Chemotherapeutic agents comprise such anti-cancer or anti-tumor agents. The administration of one or more chemotherapeutic agents as the active pharmaceutical ingredients (API) to a subject comprises cancer chemotherapy. Here, a novel use of one or more chemotherapeutic agents in chemotherapy and pharmaceutical products for its administration are among the several embodiments of the invention.

The term "agonist" refers to a compound able to increase a target in a cell in vitro or a body in vivo, whether by activating or potentiating the target's biological activity or by initiating or enhancing expression of the target. In contradistinction, the term "antagonist" refers to a compound able to decrease a target's biological activity in a cell in vitro or a body in vivo, whether by inactivating or inhibiting the target's biological activity or by terminating or silencing expression of the target. In the physiological context of the target, it may be an enzyme involved in metabolism or catabolism, a component of the enzyme complex, either of a ligand or its receptor, a component of the ligand-receptor's signaling pathway, and other cell regulatory or structural component without limitation. While an agonist or an antagonist may specifically interact with (e.g., bind to) the target directly, such compounds might also interact with the complex or the signaling pathway through other components that are not the target. Without committing to any particular mechanism or theory, the one or more chemotherapeutic agents used in the invention may act on a target within the cancer cell or through a target in noncancerous cells. The target's biological activity may relate to determination of a stem cell to become a committed cell, a cancer cell's differentiation, a cancer cell's proliferation as well as metastasis of a cancer cell. Depending on the mechanism of action, the one or more chemotherapeutic agents used in the invention may act as antagonist or agonist for a single target, or some combination of antagonist and/or agonist for multiple different targets.

The term "cell proliferation" refers to a phenomenon by which the number of cells has increased as a result of enhanced cell division (as well as cell growth and DNA replication) and/or diminished programmed cell death (i.e., apoptosis). In in vitro cancer cell culture, cell proliferation can be measured by the nuclear division index, the rate of increasing numbers of cells, the number of cell doublings or the rate thereof. In some cases, cell proliferation may be accompanied by abnormal growth control and/or morphology, genomic instability, genetic mutation, and/or epigenetic alteration; neoantigen expression, overexpression of a tumor-associated self-antigen, an activating mutation of a proto-oncogene and/or its expression, an inactivating mutation of a tumor suppressor gene and/or its underexpression, or a change in another cancer/tumor biomarker consistent with cell proliferation.

The terms "co-administration" and "administered in combination" are used interchangeably and encompass administration of two or more agents to a subject either simultaneously or sequentially. For example, the two or more agents and/or their metabolites are present in the animal at the same time. In one embodiment, co-administration includes simultaneous administration in separate compositions, administration at different times in separate compositions, or administration in a composition in which both agents are present.

Used interchangeably, the terms "effective amount" and "therapeutically effective amount" refer to an amount of a compound of the present invention that is sufficient to result in an intended application or effect, including, but not limited to, therapy of a cancer or a tumor (or a neoplasm, especially malignant) as defined herein. The therapeutically effective amount may vary depending upon the intended application (in vivo or in vitro culture of cancer cells), or the subject and cancerous condition being treated, e.g., weight and/or age of the subject in need of treatment, type and/or staging of cancer, its aggressiveness and/or severity (especially for metastases), number of cancer cells or size of tumor (i.e., tumor load), route and/or frequency of administration, etc. or any combination thereof, which can be determined by a person skilled in the art. The terms can apply to a dose administered to subjects or a concentration achieved therein that will induce a particular response in the proliferative index, the nuclear division index, the change with time of the absolute numbers of cells and/or their doubling, apoptosis, behavior of an implant, or any combination thereof. The specific dose or concentration will vary depending on the particular treatment regimen chosen, whether a cancer agent is administered in combination with another agent, use of an adjuvant, timing or frequency of administration, the target cell or tissue of the agent, and the physical delivery system in which the agent is carried.

As used herein, the term "therapy" includes treating a subject diagnosed with cancer, preventing relapse or worsening in a treated subject, and ameliorating or palliating symptoms in a treated subject, and refer to an approach for obtaining a beneficial or therapeutic effect, including, but not limited to, remission, prevention of relapse, partial remission, reducing the number and/or severity of symptoms, and palliation. The terms "first line treatment" and "primary treatment" are used interchangeably to describe the initial treatment planned for a subject, which can be chosen according to the particular type of cancer, with or without consideration of cancer staging, being treated. Related to them but different, is the term "definitive treatment" used to describe the treatment plan chosen as the best one for a subject from among different alternative treatments based on the subject's particular diagnosis. Relative to such, a compound of the present invention is being used as a "neoadjuvant" and, often, is part of the standard of care (or best practice).

A "therapeutic benefit" means at least reducing or eliminating the cancer and/or tumor, at least improving a physiological symptom associated with the cancer or tumor, at least decreasing risk as measured by a biomarker of the cancer and/or tumor, or a combination thereof. Thus, a therapeutic benefit may be achieved such that it is observed in a subject, notwithstanding that cancer cells and/or the tumor can still be detected or are still present in the subject. For prevention, a subject who has already responded to therapy by the invention or other therapy, been diagnosed as having increased risk for developing cancer, or having a precancerous lesion receives a therapeutic benefit by avoiding relapse for a longer period, reducing risk of developing cancer, increasing disease-specific survival, or otherwise improving prognosis. It will be understood by a person skilled in the art that the therapeutic benefit may be difficult to determine in a particular individual and might require studying a large population of at-risk individuals, for example in a clinical trial.

As used herein, a "therapeutic effect" encompasses a therapeutic benefit and/or a prophylactic benefit as described herein. A prophylactic effect includes delaying or eliminating the appearance of a disease or condition; delaying or eliminating the onset of symptoms of a disease or condition; slowing, halting, or reversing the progression of a disease or condition; or any combination thereof. Reducing chronic inflammation in an organ (e.g., pancreatitis, gastritis, hepatitis, or ulcerative colitis/Crohn disease) may prevent cancer (e.g., pancreatic, gastric, hepatic, or colon cancer) because the former has a DNA damage phenotype and is a risk factor for the development of cancer. Inhibition of carcinogenesis can be seen at the cellular level by histopathology, genetic analysis, or monitoring markers of inflammation. As is known in the art, a therapeutic effect may be achieved without necessarily curing disease or totally preventing disease in every treated subject.

The terms "in vivo" and "in vitro" refer to an event that takes place inside or outside a subject's intact body respectively. For example, an in vitro assay encompasses any assay run outside of a subject assay. In vitro assays encompass cell-based assays in which cells, alive or dead, are employed. In one embodiment, in vitro assays also encompass a cell-free assay in which no intact cells are employed.

The term "subject" may be human: i.e., a male or a female, e.g., a pediatric subject (e.g., an infant from birth to ~2 years, a child from ~2 to ~12 years, adolescent from ~12 to ~18 years) or an adult subject (e.g., a young adult from ~18 to ~25 years, a mature adult from ~25 to ~40 years, a middle-aged adult from ~30 to ~60 years, or a senior adult from ~60 and older). Alternatively, it may be an animal like another (nonhuman) primate or another (nonhuman) mammal including, but not limited to, cattle, pig, horse, sheep, goat, rabbit, rodent (e.g., mouse, hamster, guinea pig, or rat), cat, and/or dog.

The term "radiotherapy" means exposing a subject, using methods and compositions known to a person skilled in the art, to high-energy radiation, including without limitation, X-ray or gamma ray photons, electrons, protons, and neutrons using external beam therapy or brachytherapy. Radiation can be targeted to the particular cancerous organ or tumor and, if present, may also be directed to metastases. The kind of radiation and the protocol for delivering it are chosen depending on the type of cancer. Radiotherapy may be performed with various intents (e.g., curative, neoadjuvant before chemotherapy, adjuvant after chemotherapy or surgery, or palliative).

The term "reacting" refers to a chemical process in which the molecular or ionic structure of one or more reactants are rearranged by loss, gain, transfer, or sharing of electrons as opposed to a mere change in physical form. A chemical reaction may include, but is not limited to, the process of one or more compounds reacting (e.g., by bond formation or cleavage, salt formation, solvate formation, chelation, or other nonbond altering association) with another one or more compounds (the same or other chemical entities). A chemical reaction may be followed by steps of further chemical reactions, separation and collection (including, but not limited to, crystallization to separate crystals from mother liquor, precipitation to recover precipitates from solution, filtration to separate solids and filtrate, decanting to separate solids and solution, distillation to separate by boiling points, evaporation to separate solute and solvent), washing, and purification. A product of the chemical reaction can be isolated as a mixture of compounds or a substantially pure compound in solid form (e.g., powder, particulate) or in solution (e.g., solute dissolved in solvent). Isolating one or more chemotherapeutic compounds can involve the preparation of a salt, a solvate, a hydrate, or another complex of a chemotherapeutic agent, then collecting or separating as described above.

The term "pharmaceutically acceptable form" of a chemotherapeutic agent includes, but is not limited to, a pharmaceutically acceptable salt, solvate, hydrate, noncovalent complex, prodrug, or an isotopically-labeled derivative thereof, and mixtures thereof. The pharmaceutically acceptable form may comprise a pharmaceutically acceptable salt, referring to salts that are suitable, in the judgment of a person skilled in the art, for administration to a subject without undue toxicity, irritation, allergic response, and the like, and are commensurate with a reasonable benefit/risk ratio. Pharmaceutically acceptable salts are known in the art (see, for example, *J. Pharmaceutical Sciences* 66:1-19, 1977). Pharmaceutically acceptable salts may be derived from suitable inorganic or organic acids. The inorganic acids include, but are not limited to, hydrochloric acid, hydrobromic acid, sulfuric acid, nitric acid, phosphoric acid, and the like. The organic acids include, but are not limited to, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Examples of pharmaceutically acceptable, nontoxic acid addition salts are salts of an amino group formed with an inorganic acid such as hydrochloric acid, hydrobromic acid, phosphoric acid, sulfuric acid, or perchloric acid or with an organic acid such as acetic acid, oxalic acid, maleic acid, tartaric acid, citric acid, succinic acid, or malonic acid or by using other processes used in the art such as ion exchange. Other pharmaceutically acceptable salts include adipate, alginate, ascorbate, aspartate, benzene-sulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethane sulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or one to about 2, 3 or 4, solvent or water molecules. In some embodiments, the solvate can be a channel solvate. It will be understood that the term "a compound" as used herein encompasses the compound and solvates of the compound, as well as a mixture thereof.

As used herein, the terms "solvent," "organic solvent," or "inert solvent" each mean a solvent inert under the conditions of the reaction being described in conjunction therewith, including, without limitation, benzene, toluene, acetonitrile, ethyl acetate, isopropyl acetate, hexanes, heptanes, dioxane, tetrahydrofuran ("THF"), dimethylformamide ("DMF"), dimethylacetamide ("DMA"), chloroform, methylene chloride (dichloromethane), diethyl ether, methanol, butanol, methyl t-butyl ether ("MTBE", or "TBME"), 2-butanone ("MEK"), N-methylpyrrolidone ("NMP"), pyridine, and the like. Unless specified to the contrary, the solvents used in reactions described herein are inert organic solvents. Unless specified to the contrary, for each gram of a limiting reagent, one cubic centimeter (or mL) of solvent constitutes a volume equivalent.

The term "pharmaceutically acceptable carrier" or "pharmaceutically acceptable excipient" includes but is not limited to a vehicle (e.g., water for injection, isotonic saline), a salt, a buffer, a sugar, a stabilizer, an antioxidant or other preservative, a liquid diluent or a solid filler, a binder, a lubricant, a surfactant, a dessicant, a dispersant, a coating, and a polymeric matrix or support. Use of such pharmaceutically acceptable carriers and/or excipients is known in the art. See, e.g., *Remington: The Science and Practice of Pharmacy* and *The United States Pharmacopeia*.

The term "solid form" describes a chemotherapeutic agent in a physical state that is substantially not liquid or gaseous. The solid form may be crystalline, amorphous, or any mixture thereof. A crystal form is a solid form that is crystalline and includes, but is not limited to, a polymorph, a solvate, or a hydrate as well as salts, solvates of salts, hydrates of salts, and polymorphs thereof. A polymorph has two or more crystal forms that consist essentially of the same chemotherapeutic agent. A solvate is a crystal form that contains a solvent; a hydrate is a solvate in which the solvent comprises water. A polymorph of a solvate has more than one crystal form for a particular solvate composition. Similarly, a polymorph of a hydrate has more than one crystal form for a particular hydrate composition. A desolvated solvate is a crystal form prepared from a solvent by removing its solvent.

Specific functional groups and chemical terms are described herein more detail below. The chemical elements are identified in accordance with the periodic table (CAS version) on the inside cover of *Handbook of Chemistry and Physics*, and specific functional groups are generally defined as described therein. Additionally, general principles of organic chemistry, as well as specific functional moieties and reactivity, are described in organic chemistry textbooks, Carey's *Advanced Organic Chemistry*, Carruther's *Modern Methods of Organic Synthesis*, Greene's *Protective Groups in Organic Synthesis*, Harrold's *Basic Concepts in Medicinal Chemistry*, Larock's *Comprehensive Organic Transformations*, and March's *Advanced Organic Chemistry*.

Pharmaceutically acceptable solids may be provided in a crystalline or an amorphous form, or a mixture thereof. The desirability of each may depend on the specific application: an amorphous solid may be easier to dissolve while a crystalline solid may be more stable. A change in solid form may affect a variety of physical and chemical properties, which may provide benefits or drawbacks in processing, formulation, stability, and/or bioavailability.

A pharmaceutical composition comprising one or more chemotherapeutic agents may be administered to a subject. A solid form isolated from a synthetic process with or without a pharmaceutically acceptable carrier and/or excipient may be administered directly to a subject. Alternatively, a solid form may be may be a powder compressed into a tablet, a tablet coated for delayed release, or grains filling a capsule. In the form of a unit dose, the tablet or capsule may be self-administered by a subject.

In some embodiments, provided herein are one or more solid forms of a compound of Formula (I):

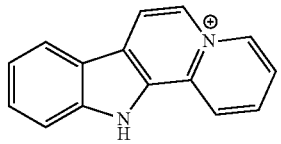 [SMILES: c1ccc2c(c1)[nH]c1c2cc[n+]2ccccc12]

or a salt, or a solvate, or a hydrate, or a salt of a solvate or a hydrate, or any mixture thereof. In one embodiment, the solid form of a compound of Formula (I) can be a crystalline form, an amorphous form, or a mixture of crystalline and amorphous forms. A solid form may comprise a crystalline form of a compound of Formula (I), or a salt, or a solvate, or a hydrate, or a salt of a solvate or a hydrate thereof, or any mixture thereof.

One or more salts of the compound of Formula (I) or a solvate (e.g., hydrate) thereof are provided. The salt is a pharmaceutically acceptable salt. The salt may be a salt of H—X, wherein X is F, Cl, Br, I, RSO$_3$, or RCO$_2$, wherein R is alkyl, aryl, substituted alkyl, or substituted aryl. One or more salts of a compound of Formula (I), wherein the salt is a hydrobromic acid salt, a hydrochloric acid salt, a sulfuric acid salt, an 1,2-ethane disulfonic acid salt, a p-toluenesulfonic acid salt, a methane sulfonic acid salt, an oxalic acid salt, a salt of 2-hydroxypropyl ethanesulfonic acid (i.e., an isethionate salt), an L-aspartic acid salt, a maleic acid salt, a phosphoric acid salt, or an ethane sulfonic acid salt.

In other embodiments, a solid form of a free base of a compound of Formula (I) or a solvate (e.g., hydrate) thereof is provided. Herein, the terms "free" and "uncharged" can be used interchangeably. A solid form provided herein may be a solvate of a free base of a compound of Formula (I). In one embodiment, the solvate is a hydrate. In some embodiments, provided herein is a pharmaceutical composition comprising a solid form of a compound of Formula (I):

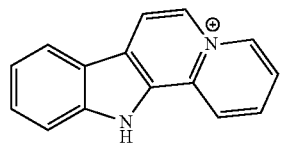 [SMILES: c1ccc2c(c1)[nH]c1c2cc[n+]2ccccc12]

or a salt, or a solvate, or a hydrate, or a salt of a solvate or a hydrate, or any mixture thereof, and one or more pharmaceutically acceptable carriers and/or excipients. Further, a pharmaceutical composition comprising a therapeutically effective amount of a solid form of a compound of Formula (I), or a salt, or a solvate, or a hydrate, or a salt of a solvate or a hydrate, or any mixture thereof, and one or more pharmaceutically acceptable carriers and/or excipients is provided.

A solid form useful in the production of medicinal preparations and can be obtained by means of a crystallization process to produce crystalline and semicrystalline forms or a solidification process to obtain the amorphous form. In certain embodiments, the crystallization is carried out by either generating a compound of Formula (I) or a salt thereof in a reaction mixture and recovering a solid form from the reaction mixture, or by dissolving a compound of Formula (I) or a salt thereof in a solvent, optionally with heat, followed by crystallizing/solidifying the product by cooling and/or by the addition of an anti-solvent for a period of time. The crystallization or solidification can be followed by drying carried out under controlled conditions until a certain solvent or water content is reached in the end solid form.

In one embodiment, the process comprises recovering a solid form after synthesis of a compound of Formula (I) or a salt thereof. In another embodiment, the method comprises recovering a solid form as a transition from a prior solid form of a compound of Formula (I) or a salt thereof (e.g., first recovering a first solid form of a compound of Formula (I) or a salt thereof, and converting the recovered first solid form to a second solid form under suitable conditions). A transition from one (e.g., first) solid form to another (e.g., second) solid form is a process within the scope of the invention. Such a transition can be used as a manufacturing process to obtain a solid form for producing a pharmaceutical composition.

In some embodiments, provided herein is a process for preparing a solid form of a salt of a compound of Formula (I) or a solvate (e.g., a hydrate) thereof, comprising: (a) contacting a compound of Formula (I) with an acid in a solvent system, and (b) producing and/or recovering a solid form of the salt of a compound of Formula (I) from the mixture resulting from step (a).

In some embodiments, provided herein is a process for preparing a solid form of a salt of a compound of Formula (I) or a solvate (e.g., a hydrate) thereof, comprising: (a) exposing a material comprising a salt of a compound of Formula (I) to a solvent system, and (b) producing and/or recovering the solid form of the salt of a compound of Formula (I) from the mixture resulting from step (a).

In some embodiments, provided herein is a process for preparing a solid form of a free base of a compound of Formula (I) or a solvate (e.g., a hydrate) thereof, comprising: (a) exposing a material comprising a salt or a free base of a compound of Formula (I) to a solvent system and (b) producing and/or recovering a solid form of the free base of a compound of Formula (I) from the mixture resulting from step (a).

In certain embodiments, step (b) may comprise one or more of the following: (i) cooling a solution containing a salt or a free base of a compound of Formula (I); (ii) adding an anti-solvent, with or without a cooling step, to cause precipitation of a solid material comprising a salt or a free base of a compound of Formula (I); (iii) evaporating a solution containing a salt or a free base of a compound of Formula (I); (iv) slurrying a material comprising a salt or a free base of a compound of Formula (I) in a solvent system; and/or (v) subjecting a material comprising a salt or a free base of a compound of Formula (I) to maturation in a solvent system.

Sulfuric Acid Salt of a Compound of Formula (I)

In some embodiments, provided herein is a sulfuric acid salt of a compound of Formula (I). It is contemplated that a sulfuric acid salt of a compound of Formula (I) can exist in a variety of solid forms. Such solid forms include a crystalline solid, such as a polymorph, a solvate, and a hydrate of crystalline sulfuric acid salt of a compound of Formula (I), as well as an amorphous solid, or any mixture thereof. All such solid forms of sulfuric acid salt of a compound of Formula (I) are contemplated under the present invention.

As used here, "a sulfuric acid salt" refers to a salt comprising at least one counterion derived from sulfuric acid ($H_2SO_4$). A counterion derived from sulfuric acid includes, but is not limited to, $HSO_4^-$ (e.g., hydrogen sulfate, hydrosulfate, or bisulfate) and $SO_4^{2-}$ (e.g., sulfate). The molar ratio of the cation to the counterion derived from sulfuric acid in a sulfuric acid salt can be any ratio known in the art. Exemplary molar ratios include, but are not limited to, about 1:2 (i.e., bis-sulfuric acid salt), about 1:1 (i.e., mono-sulfuric acid salt), and about 2:1 (i.e., hemi-sulfuric acid salt). The term "a sulfuric acid salt" includes all forms of the salt, including, but not limited to, a crystalline form, an anhydrous form, a solvate (e.g., a hydrate) form of the salt, an amorphous form, or any of the mixtures thereof.

In one embodiment, provided herein is a solid form comprising a sulfuric acid salt of a compound of Formula (I) or a solvate (e.g., hydrate) thereof. In one embodiment, provided herein is a solid form comprising a solvate of a sulfuric acid salt of a compound of Formula (I). In one embodiment, provided herein is a solid form comprising a hydrate of a sulfuric acid salt of a compound of Formula (I). In one embodiment, provided herein is a solid form comprising a crystalline form of a sulfuric acid salt of a compound of Formula (I), or a solvate (e.g., hydrate) thereof. In one embodiment, provided herein is a solid form comprising a crystalline form of a solvate of a sulfuric acid salt of a compound of Formula (I). In one embodiment, provided herein is a solid form comprising a crystalline form of a hydrate of a sulfuric acid salt of a compound of Formula (I). In one embodiment, the sulfuric acid salt of a compound of Formula (I) is a sulfate salt. In another embodiment, the sulfuric acid salt of a compound of Formula (I) is a bisulfate (i.e., hydrosulfate) salt.

Pharmaceutical Compositions

A pharmaceutical composition comprises one or more compounds as provided herein, a stereoisomer of such compound(s), an enantiomer, a mixture of enantiomers or diastereomers, or any combination thereof (e.g., a pharmaceutically acceptable salt, a hydrate, a solvate) as the active ingredient(s) and a pharmaceutically acceptable excipient including an inert vehicle (e.g., water or organic solvent), carrier, solid filler, liquid diluent, buffer, salt, sugar, and the like. In some embodiments, the composition may include a second active ingredient such as an additional chemotherapeutic agent.

Formulations

A pharmaceutical composition may be formulated for administration in liquid or solid form, including solutions, suspensions, capsules, creams, emulsions, foams, ointments, pastes, granules, micronized powders, or tablets; by a route such as oral, enteral, parenteral (e.g., intravenous, intra-arterial, subcutaneous, intramuscular, intravascular, intraperitoneal, intrathecal), ophthalmic, sublingual, transdermal, or topical; intravaginally or intrarectally; and by a medical device such as inhaler, nebulizer, patch, pessary, stent, or suppository.

A pharmaceutical vehicle may be aqueous or nonaqueous, including water, glycerol, oils, alcohols, polyols (e.g., a glycerol, a polypropylene glycol, a polyethylene glycol), and mixtures thereof. Examples of carriers include liposomes, hydrogels, stable emulsions, polymeric micelles, cyclodextrins, dendrimers, microspheres, and nanoparticles or nanofibers.

The composition can also contain excipients such as preservatives, surfactants, wetting agents, binders, dispersants, lubricants, stabilizers, and/or dessicants. The action of microorganisms upon the compounds described herein can be prevented by including an antimicrobial agent, for example, paraben, chlorobutanol, phenol sorbic acid, and the like. It can also be desirable to include isotonic agents, such as dextrose and/or sodium chloride, into the composition. In addition, prolonged absorption of an infused or injected pharmaceutical composition can be brought about by the inclusion of an agent that delays absorption.

Methods of formulating a pharmaceutical composition comprise a step of bringing into association a compound of the present invention and an excipient. More particularly, a pharmaceutical composition can be formulated by bringing into contact a compound of the present invention with a vehicle or carrier and, optionally, other excipients. A liquid form may be aseptically dispensed into a sterile container with or without an intervening step of drying the composition. Alternatively, a dry form may be aseptically dispensed to a sterile container with or without an intervening step of forming the composition into a plurality of unit doses. Lot testing may be performed to confirm the absence of viruses, pyrogen, or other contaminants. Processes for formulating a pharmaceutical composition or further processing into downstream products (e.g., unit doses of tablets or capsules for enteral self-administration, multidose blister pack, unit dose reconstitutable for single parenteral administration) is conventional in the art. Except insofar as a carrier or an excipient is incompatible with a chemotherapeutic agent such as by resulting in an undesirable physiological effect or otherwise interacting in a deleterious manner with another component of a pharmaceutical composition, the carrier or the excipient's use is contemplated to be within the scope of the invention.

Formulations for Oral Administration

A pharmaceutical composition comprising a compound of Formula (I) and a pharmaceutically acceptable carrier and/or excipient may be formulated for oral administration. The pharmaceutical composition for oral administration contains an effective amount of one or more compounds of Formula (I); optionally, an effective amount of one or more second agents; and one or more pharmaceutical carriers and/or excipients suitable for oral administration. Sometimes, the pharmaceutical composition further contains an effective amount of a third agent.

A pharmaceutical composition suitable for oral administration can be presented in a discrete dosage form, such as a tablet or a capsule, or an elixir or a syrup containing a predetermined amount of an active ingredient as a fine or granulated powder, a solution, a suspension, or an emulsion. The pharmaceutical composition can be formulated by a conventional procedure comprising bringing the active ingredient into association with a pharmaceutically acceptable carrier and/or excipient, which constitutes one or more inactive ingredients. For example, the active ingredient may be uniformly and intimately admixed with a finely divided solid carrier, a liquid carrier, or both and then, if necessary, shaping the product into the desired dosage form. For example, a tablet can be made by compression or molding. Compressed tablets can be prepared by compressing in a suitable machine the API in a free-flowing form such as powder or granules, optionally mixed with an excipient such as, but not limited to, a salt, a buffer, a stabilizer, a preservative, a filler, a binder, a lubricant, a surfactant, and/or a dispersant. Optionally, a carrier can be added to the mix. Tablets can be made by molding in a suitable machine a similar mixture of API, inert excipients, and optional carrier moistened with a vehicle. If desirable for improved drug delivery or storage, a coating can be added for delayed or sustained release to make a coated tablet.

An anhydrous pharmaceutical compositions comprising an active ingredient may be preferred because water can facilitate the degradation of some compounds. For example, water can be added (e.g., about 5%) in the pharmaceutical arts as a means of simulating long-term storage in order to determine characteristics such as shelf-life or the stability of formulations over time. An anhydrous pharmaceutical composition can be prepared using anhydrous or low moisture containing ingredients and low moisture or low humidity conditions. For example, a pharmaceutical composition that contains lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed containers, blister packs, vials and bottles, bags, and the like.

An active ingredient can be combined in an admixture with a pharmaceutically acceptable carrier according to conventional pharmaceutical compounding techniques. The carrier can take a wide variety of forms depending on the form of preparation desired for administration. In preparing the pharmaceutical compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as an elixir, a syrup, or a suspension); or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. In some embodiments, tablets can be coated by standard aqueous or nonaqueous techniques.

A binder suitable for a pharmaceutical composition includes, but is not limited to, corn or potato starch, gelatin, gum arabic, alginic acid or a salt thereof, gum tragacanth, guar gum, pre-gelatinized starch, cellulose or a derivative thereof (e.g., methyl cellulose, ethyl cellulose, cellulose acetate, carboxymethyl cellulose, hydroxypropylmethyl cellulose, microcrystalline cellulose), polyvinyl pyrrolidone, and any mixture thereof.

Examples of a suitable filler for use in a pharmaceutical composition include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

A disintegrant may be used to form a pharmaceutical composition to provide tablets that disintegrate when exposed to an aqueous environment. Too much disintegrant can produce tablets that are easily broken during transport; too little can be insufficient for disintegration to occur and, thus, alter the rate and extent of release of the active ingredient. Thus, a sufficient amount of disintegrant that is neither too little nor too much to detrimentally alter the release of the active ingredients can be used to form a unit dose of a compound of Formula (I). The amount of disintegrant used can vary based upon the type of formulation and mode of administration. About 0.5 to about 15 weight percent of disintegrant, or about 1 to about 5 weight percent of disintegrant, can be used in the pharmaceutical composition. A disintegrant that can be used to form a pharmaceutical composition includes, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

A lubricant that can be used to form a pharmaceutical composition includes, but is not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When an aqueous suspension, syrup, or elixir is desired for oral administration, the active ingredient therein can be combined with various sweetening or flavoring agents, coloring matter or dyes and, for example, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be used. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

A surfactant that can be used to form a pharmaceutical composition includes, but is not limited to, hydrophilic or lipophilic surfactants, and mixtures thereof. That is, a mixture of hydrophilic surfactants can be employed, a mixture of lipophilic surfactants can be employed, or a mixture of at least one hydrophilic surfactant and at least one lipophilic surfactant can be employed.

A hydrophilic surfactant can be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants can be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants can include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of triglycerides, vegetable oils, and hydrogenated vegetable oils. The polyol can be glycerol, sorbitol, ethylene glycol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of glycerides, vegetable oils, hydrogenated vegetable oils, fatty acids and sterols; oil-soluble vitamins/vitamin derivatives; and mixtures thereof. Within this group, non-limiting examples of lipophilic surfactants include glycerol fatty acid esters, propylene glycol fatty acid esters, and mixtures thereof, or are hydrophobic transesterification products of a polyol with at least one member of vegetable oils, hydrogenated vegetable oils, and triglycerides.

In one embodiment, the pharmaceutical composition can include a solubilizer to ensure good solubilization and/or dissolution of a compound as provided herein and to minimize precipitation of the compound. This can be especially important for pharmaceutical compositions for non-oral use, e.g., pharmaceutical compositions for injection. A solubilizer can also be added to increase the solubility of the hydrophilic drug and/or other components, such as surfactants, or to maintain the pharmaceutical composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, a polyethylene glycol, a polypropylene glycol, a polyvinyl alcohol, hydroxypropylmethyl cellulose, and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkyl pyrrolidone, N-hydroxyalkyl pyrrolidone, N-alkyl piperidone, N-alkyl caprolactam, dimethylacetamide and polyvinyl pyrrolidone; esters such as ethyl propionate, tributylcitrate, acetyl triethyl N-hydroxyethyl yrrolidone citrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers can also be used. Examples include, but not limited to, triacetin, triethylcitrate, ethyl oleate, ethyl caprylate, dimethylacetamide, N-methylpyrrolidone, N-hydroxyethyl pyrrolidone, polyvinyl pyrrolidone, hydroxypropylmethyl cellulose, hydroxypropyl cyclodextrins, ethanol, polyethylene glycol 200-100, glycofurol, transcutol, propylene glycol, and dimethyl isosorbide. In some embodiments, solubilizers include sorbitol, glycerol, triacetin, ethyl alcohol, PEG-400, glycofurol and propylene glycol.

The amount of solubilizer that can be included is not particularly limited. The amount of a given solubilizer can be limited to a bioacceptable amount, which can be readily determined by a person skilled in the art. In some circumstances, it can be advantageous to include amounts of solubilizers far in excess of bioacceptable amounts, for example to maximize the concentration of the drug, with excess solubilizer removed prior to providing the pharmaceutical composition to a subject using conventional techniques, such as distillation or evaporation.

The pharmaceutical composition can further include one or more pharmaceutically acceptable additives and/or excipients. Such an additive and/or an excipient include, without limitation, detackifiers, anti-foaming agents, buffering agents, polymers, antioxidants, preservatives, chelating agents, viscomodulators, tonicifiers, flavorants, colorants, oils, odorants, opacifiers, suspending agents, binders, fillers, plasticizers, lubricants, and mixtures thereof.

Exemplary preservatives can include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, and methylparaben. In certain embodiments, the preservative is an anti-oxidant. In other embodiments, the preservative is a chelating agent.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils also include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

In addition, an acid or a base can be incorporated into the pharmaceutical composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)-aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Examples can include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, parabromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Formulations for Parenteral Administration

In some embodiments, provided herein are pharmaceutical compositions for parenteral administration containing a compound as provided herein, and a pharmaceutical excipient suitable for parenteral administration. In some embodiments, provided herein are pharmaceutical compositions for parenteral administration containing: an effective amount of a disclosed compound; optionally, an effective amount of one or more second agents; and one or more pharmaceutically acceptable carriers and/or excipients suitable for parenteral administration. In some embodiments, the pharmaceutical composition further contains: an effective amount of a third agent.

Aqueous solutions in saline are often used for infusion or injection. The prevention of the action of microorganisms can be brought about by various antibacterial and antifungal agents, for example, parabens, chlorobutanol, phenol, sorbic acid, thimerosal, and the like.

Sterile solutions are prepared by incorporating a compound of Formula (I) in an effective amount in a suitable solvent with various other inactive ingredients as described above, as appropriate, followed by filter sterilization. Generally, dispersions are prepared by incorporating the various sterilized active ingredients into a sterile vehicle which contains the basic dispersion medium and the appropriate other inactive ingredients from those described above. In the case of sterile powders for the preparation of a sterile infusable or injectable solution, certain methods of preparation are vacuum-drying and freeze-drying techniques which yield a powder of the active ingredient plus any additional ingredient from a previously sterile-filtered solution thereof.

The infusible or injectable formulations can be sterilized, for example, by filtration through a microbe-retaining filter, or by incorporating sterilizing agents in the form of sterile solid compositions which can be dissolved or dispersed in sterile water or other sterile injectable medium prior to use. An infusable or injectable pharmaceutical composition can contain from about 0.1% w/w to about 5% w/w of a compound as provided herein.

A pharmaceutical composition as provided herein can be formulated into preparations as a solid, a semi-solid, or a liquid; such as an ointment, a gel, a cream, a lotion, a paste, a slurry, an oil, an emulsion, or a foam. In general, a carrier having a high density is capable of providing an area that maintains prolonged exposure to active ingredients. In contrast, a solution formulation can provide more immediate exposure of the active ingredient to the chosen area.

Topically-administrable formulations can, for example, comprise from about 1% to about 10% (w/w) of a compound provided herein relative to the total weight of the formulation, although the concentration of the compound provided herein in the formulation can be as high as the solubility limit of the compound in the solvent. In some embodiments, topically-administrable formulations can, for example, comprise from about 1% to about 9% (w/w) of a compound provided herein, such as from about 1% to about 8% (w/w), further such as from about 1% to about 7% (w/w), further such as from about 1% to about 6% (w/w), further such as from about 1% to about 5% (w/w), further such as from about 1% to about 4% (w/w), further such as from about 1% to about 3% (w/w), and further such as from about 1% to about 2% (w/w) of a compound provided herein. Formulations for topical administration can further comprise one or more of the additional pharmaceutically acceptable carriers and/or excipients described herein.

Formulations for Inhalation Administration

In some embodiments, provided herein are pharmaceutical compositions for inhalation administration containing a compound as provided herein, and a pharmaceutical excipient suitable for topical administration. In some embodiments, provided herein is a pharmaceutical composition for inhalation administration containing: an effective amount of a compound as provided herein; optionally, an effective amount of one or more second agents; and one or more pharmaceutical acceptable carriers and/or excipients suitable for inhalation administration. In some embodiments, the pharmaceutical composition further contains: an effective amount of a third agent.

A pharmaceutical composition for ingestion may be a solution in which a compound as provided herein is dissolved or suspended in one or more pharmaceutically acceptable, aqueous and/or organic solvents, or a mixture thereof; or a tablet containing compressed powder, a capsule containing granules, or a reconstitutable powder. A pharmaceutical composition in liquid or solid form may contain one or more pharmaceutically acceptable carriers and/or excipients as described herein. It may be administered enterally or parenterally; by an appropriate route selected from among oral (preferred), infusion intravenously, intraperitoneally, or intrathecally, injection subcutaneously or intramuscularly; for a local or a systemic effect.

Formulations for Parenteral Administration

A pharmaceutical composition can be formulated for parenteral administration (e.g., intravenous infusion, intra-arterial or intravesicular, subcutaneous or intramuscular injection, delivery by a catheter or through a port, or any combination thereof). It can contain an effective amount of a compound of Formula (I) and a pharmaceutically acceptable carrier suitable for parenteral administration. A pharmaceutical composition suitable for parenteral administration can be presented as a discrete unit dose, such as a glass vial, a vacuum bottle, or a plastic bag, each containing a predetermined amount of an active ingredient in dry form, dissolved in a solution, in a suspension, or as an emulsion. Systemic administration may be achievable.

A pharmaceutical composition can be prepared by dissolving an active ingredient in a sterile aqueous solution such as water for injection, physiological saline or other saline solution, balance salt solution or other buffering solution, etc., or by combining powder compositions to be dissolved before use. Other carriers include, but are not limited to water soluble polyethers, such as a polyethyene glycol; polyvinyls, such as a polyvinyl alcohol or a povidone; cellulose derivatives, such as a methylcellulose or hydroxypropylmethyl cellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. In some embodiments, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxypropylmethyl cellulose, hydroxyethyl cellulose, carboxymethyl cellulose, hydroxypropyl cellulose or other agents known to those skilled in the art).

In some cases, the colloid particles include at least one cationic agent and at least one non-ionic sufactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quarternary ammonium compound, a cationic lipid, an amino alcohol, a biguanidine salt, a cationic compound or any mixture thereof. In some cases, the cationic agent is a biguanidine salt such as chlorhexidine, polyaminopropyl biguanidine, phenformin, alkylbiguanidine, or any mixture thereof. In some cases, the quaternary ammonium compound is a benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, rnyristylalkonium halide, stearalkonium halide or a mixture of two or more thereof. In some cases, cationic agent is a benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof. In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising poluoxyl-40 hydrogenated castor oil, polyoxyl-60 hydrogenated castor oil or polyoxyl-100 hydrogenated castor oil.

Formulations for Controlled-Release Administration

In some embodiments, provided herein are pharmaceutical compositions for controlled release administration containing a compound as provided herein, and a pharmaceutical excipient suitable for controlled release administration. In some embodiments, provided herein are pharmaceutical compositions for controlled release administration containing: an effective amount of a disclosed compound; optionally, an effective amount of one or more second agents; and one or more pharmaceutical excipients suitable for controlled release administration. In some embodiments, the pharmaceutical composition further contains: an effective amount of a third agent.

Active agents such as a compound of Formula (I) may be administered by sustained, delayed, or other controlled release using a delivery device (e.g., biodegradable polymer, emulsion, encapsulated, enteric coating) or other means known to a person skilled in the art. Such dosage forms can be used to provide controlled release of one or more active agents using, for example, an emulsion, a gel, hydroxypropylmethylcellulose (HPMC), a liposome or a micelle, a multilayer coating, an osmotic system, particles or spheres, a permeable membrane, polylactic acid or another biodegradable polymer, or any combination thereof to provide the desired release profile in varying proportions. Suitable controlled release formulations are known in the art, including those described herein, can be readily selected for use with the active agents provided herein. Thus, the pharmaceutical compositions provided encompass single unit dose suitable for oral administration such as, but not limited to, tablets, caplets, capsules, and gel caps that are adapted for controlled release.

All controlled release pharmaceutical products have a common goal of improving drug therapy over that achieved by their noncontrolled counterparts. In some embodiments, the use of a controlled release preparation in medical treatment is characterized by a minimum of drug substance being employed to cure or control the disease, disorder, or condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

In some embodiments, controlled release formulations are designed to initially release an amount of a compound as provided herein that promptly produces the desired therapeutic effect, and gradually and continually release other amounts of the compound to maintain this level of therapeutic or prophylactic effect over an extended period of time. In order to maintain this constant level of the compound in the body, the compound should be released at a rate that will replace the amount of drug being metabolized and excreted from the body. Controlled release of an active agent can be stimulated by various conditions including, but not limited to, pH, temperature, enzymes, water, or other physiological conditions or compounds.

In certain embodiments, the pharmaceutical composition can be administered using intravenous infusion, an implantable osmotic pump, a transdermal patch, liposomes, or other modes of administration. In one embodiment, a pump can be used (see, Sefton, *CRC Crit. Ref Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, 2:115-138, 1984). Other controlled release systems are discussed in the review by Langer, *Science* 249:1527-1533 (1990). The one or more active agents can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinyl alcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The one or more active agents then diffuse through the outer polymeric membrane in a release rate controlling step. The percentage of active agent in such parenteral compositions is highly dependent on the specific nature thereof, as well as the needs of the subject.

Liposomes

An embodiment to reduce degradation of the active pharmaceutical ingredient and/or to increase its absorption enterally is to encapsulate a compound as provided herein in liposomes. In a distribution of sizes within the population, a majority of the liposomes may have a diameter of less than 400 nm. A majority of the liposomes may have a diameter between about 100 and about 150 nm. The liposomes may be coated or stabilized.

Liposomes are used for drug delivery due to their useful properties. Dissolved hydrophilic solutes cannot readily pass through the lipids. Hydrophobic chemicals can be dissolved into the membrane and, in this way, liposomes can carry both hydrophobic molecules and hydrophilic molecules. To deliver the molecules to sites of action, the lipid bilayer can fuse with other bilayers such as the cell membrane, thus delivering the liposome contents. By preparing the liposomes in a solution comprising a compound as provided herein, they can improve delivery of the compound past cells lining the digestive system.

Another interesting property of liposomes is their ability to target tumor tissues. The endothelial walls of blood vessels are encapsulated by endothelial cells that are bound together by tight junctions. These tight junctions stop any large particles in the blood from leaking out of the vessel. Tumor vessels do not contain the same level of seal between cells and are leaky. Liposomes of certain sizes, typically less than 400 nm, can rapidly enter tumor sites from the blood, but are kept in the bloodstream by the endothelial wall in healthy tissue vasculature.

Liposomes can also be designed to deliver a compound as provided herein in other ways. Liposomes that contain low pH can be constructed such that dissolved aqueous drugs will be charged in solution (i.e., the pH is outside the drug's pl range). As the pH naturally neutralizes within the liposome (protons can pass through some membranes), a compound as provided herein will be neutralized, allowing it to freely pass through a membrane. These liposomes work to deliver drug by diffusion rather than by direct cell fusion. Another strategy for liposome drug delivery is to target endocytosis events. Liposomes can be made in a particular size range that makes them viable targets for natural macrophage phagocytosis. These liposomes may be digested while in the cell's phagosome, thus releasing a compound as provided herein. Liposomes can also be decorated with opsonins and ligands to activate endocytosis in other cell types.

Liposomes may be prepared in accordance with known laboratory techniques. Liposomes can be prepared by dissolving liposomal lipids in a solvent in a container. The container may have a volume ten times greater than the volume of the expected suspension of liposomes. Using a rotary evaporator, the solvent is removed at approximately 40° C. under negative pressure. The solvent normally is removed within about 5 min to 2 hr, depending on the desired volume of the liposomes. The composition can be dried further in a desiccator under vacuum. Dried lipids can be hydrated at about 25 mM-50 mM phospholipid in sterile, pyrogen-free water by shaking until all of the lipid film is resuspended. The aqueous liposomes can then be separated into aliquots, each placed in a vial, lyophilized, and sealed under vacuum.

The lipids may be phospholipids like phosphatidyl ethanolamine and cholesterol. Phospholipids are amphiphilic with the hydrocarbon tail of the molecule being hydrophobic and its polar head hydrophilic. As liposome contact aqueous solutions on both sides, the phospholipids accommodate this by forming a phospholipid bilayer with the hydrophobic tails facing each other. They can carry a net positive charge, a net negative charge, or be neutral. For example, dicetyl phosphate can be used to confer a negative charge on the liposomes while stearylamine can be used to confer a positive charge on the liposomes.

Without limitations the lipid can be selected from the group consisting of sterol lipids, fatty acids, fatty alcohols, glycerolipids (e.g., monoglycerides, diglycerides, and triglycerides), phospholipids, glycerophospholipids, sphingolipids, prenol lipids, saccharolipids, polyketides, or any combination thereof. The lipid can be a polyunsaturated fatty acid or alcohol. The terms polyunsaturated fatty acid and polyunsaturated fatty alcohol means a fatty acid or an alcohol, respectively, with two or more carbon-carbon double bonds in its hydrocarbon chain. The lipid can also be a highly unsaturated fatty acid or alcohol. The terms highly polyunsaturated fatty acid and highly polyunsaturated fatty alcohol means a fatty acid or an alcohol, respectively. having at least 18 carbon atoms and at least 3 double bonds.

The lipid can be selected from the group consisting of cholesterol, 1,3-propanediol dicaprylate/dicaprate; 10-undecenoic acid, 1-dotriacontanol, 1-heptacosanol, 1-nonacosanol, 2-ethyl hexanol, androstanes, arachidic acid, arachidonic acid, arachidyl alcohol, behenic acid, behenyl alcohol, capric acid, capric alcohol, capryl alcohol, caprylic acid, caprylic/capric acid ester of saturated fatty alcohol C12-C18, caprylic/capric triglyceride, caprylic/capric triglyceride, ceramide phosphorylcholine, ceramide phosphorylethanolamine, ceramide phosphorylglycerol, ceroplastic acid, cerotic acid, cerotic acid, ceryl alcohol, cetearyl alcohol, cetyl alcohol, cholanes, cholestanes, cholesterol, cis-11-eicosenoic acid, cis-11-octadecenoic acid, cis-13-docosenoic acid, docosahexaenoic acid, egg lecithin, eicosapentaenoic acid, eicosenoic acid, elaidic acid, elaidolinolenyl alcohol, elaidolinoleyl alcohol, elaidyl alcohol, erucic acid, erucyl alcohol, estranes, ethylene glycol distearate, geddic acid, geddyl alcohol, glycerol tricaprylate/caprate, glycerol tricaprylate/caprate, glyceryl monocaprylate, glyceryl triacetate, glyceryl tricaprylate, glyceryl tricaprylate/caprate/laurate, glyceryl tricaprylate/tricaprate, glyceryl tripalmitate, henatriacontylic acid, heneicosyl alcohol, heneicosylic acid, heptacosylic acid, heptadecanoic acid, heptadecyl alcohol, hexatriacontylic acid, isostearic acid, isostearyl alcohol, lacceroic acid, laurie acid, lauryl alcohol, lignoceric acid, lignoceryl alcohol, linoelaidic acid, linoleic acid, linolenyl alcohol, linoleyl alcohol, margaric acid, melissic acid, melissyl alcohol, montanic acid, montanyl alcohol, myricyl alcohol, myristic acid, myristoleic acid, myristyl alcohol, neodecanoic acid, neoheptanoic acid, neononanoic acid, nervonic, nonacosylic acid, nonadecyl alcohol, nonadecylic acid, nonadecylic acid, oleic acid, oleyl alcohol, palmitic acid, palmitoleic acid, palmitoleyl alcohol, pelargonic acid, pelargonic alcohol, pentacosylic acid, pentadecyl alcohol, pentadecylic acid, phosphatidic acid, phosphatidylcholine, phosphatidylethanolamine, phosphatidylinositol, phosphatidylinositol bisphosphate, phosphatidylinositol phosphate, phosphatidylinositol triphosphate, phosphatidylserine, polyglyceryl-6-distearate, pregnanes, propylene glycol dicaprate, propylene glycol dicaprylocaprate, propylene glycol dicaprylocaprate, psyllic acid, recinoleaic acid, recinoleyl alcohol, sapienic acid, soy lecithin, stearic acid, stearidonic, stearyl alcohol, tricosylic acid, tridecyl alcohol, tridecylic acid, undecyl alcohol, undecylenic acid; undecylic acid, α-linolenic acid, and γ-linolenic acid.

The phospholipid may be one or more of phosphatidyl cholines, phosphatidyl cholines with acyl groups having 6 to 22 carbon atoms, phosphatidyl ethanolamines, phosphatidyl inositols, phosphatidic acids, phosphatidyl serines, sphingomyelin, phosphatidyl glycerols, or any combination thereof. More specifically, the phospholipid may be one or more of phosphatidylcholine, phosphatidylglycerol, lecithin, sphingomyelin, phosphatidylserine, phosphatidic acid, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, distearoylphosphatidylcholine, stearoyl-palmitoyl-phosphatidylcholine, dipalmitoylphosphatidylethanolamine, distearoylphosphatidylethanolamine, dimyristoylphosphatidylserine, dioleylphosphatidylcholine, dimyristoylphosphatidylcholine, dioleoylphosphatidylethanolamine, palmitoyloleoylphosphatidylcholine, egg phosphatidylcholine, distearoylphosphatidylcholine, dioleoylphosphatidylcholine, dipalmitoylphosphatidylcholine, dioleoylphosphatidylglycerol, dipalmitoylphosphatidylglycerol, phosphatidylethanolamine, or any combination thereof.

In some embodiments, the lipid is a lipid conjugated with polyethylene glycol (PEG). The PEG conjugated lipid may any one or more of PEG conjugated diacylglycerols and dialkylglycerols, PEG-conjugated phosphatidylethanolamine and phosphatidic acid, PEG conjugated ceramides, PEG conjugated dialkylamines, PEG conjugated 1,2-diacyloxypropan-3-amines, and any combinations thereof.

Dosages

A compound described herein can be delivered in the form of pharmaceutically acceptable compositions which comprise a therapeutically effective amount of a compound as provided herein and/or one or more additional chemotherapeutic agents, formulated together with one or more pharmaceutically acceptable carriers and/or excipients. In some instances, a compound as provided herein and the additional chemotherapeutic agent are administered in separate pharmaceutical compositions and can (e.g., because of different physical and/or chemical characteristics) be administered by different routes (e.g., one chemotherapeutic agent is administered orally, while the other is administered intravenously). In other instances, a compound as provided herein and the additional chemotherapeutic agent can be administered separately, but via the same route (e.g., both orally or both intravenously). In still other instances, the compound described herein and the additional chemotherapeutic agent can be administered in the same pharmaceutical composition.

The selected dosage level will depend upon a variety of factors including, for example, the activity of the particular compound employed, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

In general, a suitable daily dose of a compound described herein and/or a chemotherapeutic will be that amount of the compound which, in some embodiments, can be the lowest dose effective to produce a therapeutic effect. Such an effective dose will generally depend upon the factors described above. Generally, doses of the compounds described herein for a patient, when used for the indicated effects, will range from about 0.0001 mg to about 100 mg per day, or about 0.001 mg to about 100 mg per day, or about 0.01 mg to about 100 mg per day, or about 0.1 mg to about 100 mg per day, or about 0.0001 mg to about 500 mg per day, or about 0.001 mg to about 500 mg per day, or about 0.01 mg to 1000 mg, or about 0.01 mg to about 500 mg per day, or about 0.1 mg to about 500 mg per day, or about 1 mg to 50 mg per day, or about 5 mg to 40 mg. An exemplary dosage is about 10 to 30 mg per day. In some embodiments, for a 70 kg human, a suitable dose would be about 0.05 to about 7 g/day, such as about 0.05 to about 2.5 g/day. Actual dosage levels of the active ingredients in the pharmaceutical compositions described herein can be varied so as to obtain an amount of the active ingredient which is effective to achieve the desired therapeutic response for a particular patient, composition, and mode of administration, without being toxic to the patient. In some instances, dosage levels below the lower limit of the aforesaid range can be more than adequate, while in other cases still larger doses can be employed without causing any harmful side effect, e.g., by dividing such larger doses into several small doses for administration throughout the day.

In some embodiments, the compounds can be administered daily, every other day, three times a week, twice a week, weekly, or bi-weekly. The dosing schedule can include a "drug holiday," e.g., the drug can be administered for two weeks on, one week off, or three weeks on, one week off, or four weeks on, one week off, etc., or continuously, without a drug holiday. The compounds can be administered orally, intravenously, intraperitoneally, intrathecally, topically, transdermally, intramuscularly, subcutaneously, intranasally, sublingually, or by any other route.

In some embodiments, a compound as provided herein is administered in multiple doses. Dosing can be about once, twice, three times, four times, five times, six times, or more than six times per day. Dosing can be about once a month, about once every two weeks, about once a week, or about once every other day. In another embodiment, a compound as provided herein and another agent are administered together from about once per day to about 6 times per day. In another embodiment, the administration of a compound as provided herein and an agent continues for less than about 7 days. In yet another embodiment, the administration continues for more than about 6 days, about 10 days, about 14 days, about 28 days, about two months, about six months, or about one year. In some cases, continuous dosing is achieved and maintained as long as necessary.

Administration of the pharmaceutical compositions as provided herein can continue as long as necessary. In some embodiments, an agent as provided herein is administered for more than about 1, about 2, about 3, about 4, about 5, about 6, about 7, about 14, about 21, or about 28 days. In some embodiments, an agent as provided herein is administered for less than about 28, about 21, about 14, about 7, about 6, about 5, about 4, about 3, about 2, or about 1 day. In some embodiments, an agent as provided herein is administered for about 1, about 2, about 3, about 4, about 5, about 6, about 7, about 14, about 21, or about 28 days. In some embodiments, an agent as provided herein is administered chronically on an ongoing basis, e.g., for the treatment of chronic effects.

Since the compounds described herein can be administered in combination with other treatments (such as additional chemotherapeutics, radiation or surgery), the doses of each agent or therapy can be lower than the corresponding dose for single-agent therapy. The dose for single-agent therapy can range from, for example, about 0.0001 to about 200 mg, or about 0.001 to about 100 mg, or about 0.01 to about 100 mg, or about 0.1 to about 100 mg, or about 1 to about 50 mg per kilogram of body weight per day.

Kit of Parts

In some embodiments, provided herein are kits. The kits can include a compound or pharmaceutical composition as provided herein, in suitable packaging, and written material that can include instructions for use, discussion of clinical studies, listing of side effects, and the like. Such kits can also include information, such as scientific literature references, package insert materials, clinical trial results, and/or summaries of these and the like, which indicate or establish the activities and/or advantages of the pharmaceutical composition, and/or which describe dosing, administration, side effects, drug interactions, or other information useful to the health care provider. Such information can be based on the results of various studies, for example, studies using experimental animals involving in vivo models and studies based on human clinical trials.

In some embodiments, a memory aid is provided with the kit, e.g., in the form of numbers next to the tablets or capsules whereby the numbers correspond with the days of the regimen which the tablets or capsules so specified should be ingested. A "daily dose" can be a single tablet or capsule or several tablets or capsules to be taken on a given day.

The kit can further contain another agent. In some embodiments, the compound as provided herein and the agent are provided as separate pharmaceutical compositions in separate containers within the kit. In some embodiments, the compound as provided herein and the agent are provided as a single pharmaceutical composition within a container in the kit. Suitable packaging and additional articles for use (e.g., measuring cup for liquid preparations, foil wrapping to minimize exposure to air, and the like) are known in the art and can be included in the kit. In other embodiments, kits can further comprise devices that are used to administer the active agents. Examples of such devices include, but are not limited to, syringes, drip bags, patches, and inhalers. Kits described herein can be provided, marketed and/or promoted to health providers, including physicians, nurses, pharmacists, formulary officials, and the like.

An example of such kits is a blister pack, which are known in the art and used for packaging unit doses (tablets, capsules, and the like) in the pharmaceutical industry. A blister pack may comprise a first sheet of stiff but deformable material, preferably transparent plastic. During packaging, depressions are formed in the plastic sheet. They have the size and shape of the tablets or capsules, which are then positioned in those depressions. The blister pack may also comprise a second sheet of sturdy but tearable material, preferably metal foil or coated paper, having the same size and shape as the first sheet. Next, the sheets are aligned, pressed together, and sealed around edges of the depressions to form opposed top and bottom sides of the blister pack with the tablets or capsules being loosely held in their positions. As a result, the tablets or capsules are packaged into the blister pack. By manually pressing on any depression of the first sheet, that depression is flattened, the tablet or capsule is pushed until meeting resistance from the second sheet, that tablet or capsule tears an opening in the second sheet, and the tablet or capsule is removed through the opening without disturbing the rest of the tablets or capsules.

Kits can further comprise pharmaceutically acceptable carriers that can be used to administer one or more active agents. For example, if an active agent is provided in a solid form that must be reconstituted for parenteral administration, the kit can comprise a sealed container of a suitable carrier in which the active agent can be dissolved to form a particulate-free sterile solution that is suitable for parenteral administration. Examples of pharmaceutically acceptable carriers include, but are not limited to: Water for Injection USP and other aqueous vehicles such as, but not limited to, Sodium Chloride Injection, Ringer's Injection, Dextrose Injection, Dextrose and Sodium Chloride Injection, and Lactated Ringer's Injection.

An anhydrous pharmaceutical composition comprises an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. An anhydrous pharmaceutical composition can be prepared using anhydrous or low moisture containing ingredients and low moisture or low humidity conditions. For example, a pharmaceutical composition that contains lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed container, plastic or the like, unit dose containers, blister packs, and the like.

A subject receiving cancer therapy as described herein may have been diagnosed with a cancer including, but not limited to, one or more of the following: brain cancer (glioblastoma), pancreatic cancer, colorectal cancer, uterine cancer, cervical cancer, ovarian cancer, breast cancer, prostate cancer, testicular cancer, lung cancer, melanoma, osteosarcoma, renal cell carcinoma, soft tissue sarcoma, and thyroid cancer.

More particularly, a solid tumor and/or a metastases thereof benefiting from a cancer therapy as described herein includes, but is not limited to, one or more of the following: soft tissue sarcomas; breast cancers such as an invasive lobular carcinoma, an invasive ductal carcinoma like a tubular carcinoma, a medullary carcinoma, a colloid carcinoma, or a cribriform carcinoma; ovarian cancers such as an epithelial ovarian tumor like an adenocarcinoma; uterine cancers; cervical cancers such as an adenocarcinoma in cervix epithelial including a squamous cell carcinoma and an adenocarcinoma; prostate cancers such as a prostate cancer such as an adenocarcinoma or an adenocarcinoma that has migrated to the bone; pancreatic cancers such as epithelioid carcinoma in the pancreatic duct tissue and an adenocarcinoma in a pancreatic duct; bladder cancers such as a transitional cell carcinoma in urinary bladder, a urothelial carcinoma (a transitional cell carcinoma), a tumor in urothelial cells that line the bladder, a squamous cell carcinoma, an adenocarcinoma, or a small cell cancer; bone cancers such as a chondrosarcoma, a chordoma, an osteosarcoma, a Ewing sarcoma, a malignant fibrous histiocytoma, or a fibrosarcoma; lung cancers such as a non-small cell lung cancer like a squamous cell carcinoma, an adenocarcinoma, and a large cell undifferentiated carcinoma, or a small cell lung cancer; skin cancers such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; Kaposi's Sarcoma; viral-induced cancers including hepatitis B virus (HBV), hepatitis C virus (HCV), and hepatocellular carcinoma; and human papilloma virus (HPV) and cervical cancer; central nervous system cancers (CNS) such as primary brain tumor, which includes a glioma (astrocytoma, anaplastic astrocytoma, or glioblastoma multiforme), an oligodendroglioma, an ependymoma, a meningioma, schwannoma, and a medulloblastoma; peripheral nervous system cancers such as an acoustic neuroma or a malignant peripheral nerve sheath tumor, including a neurofibroma and a schwannoma, a malignant fibrous cytoma, a malignant fibrous histiocytoma, a malignant meningioma, a malignant mesothelioma, or a malignant mixed Müllerian tumor; oral cavity and oopharyngeal cancers such as a hypopharyngeal cancer, a laryngeal cancer, a nasopharyngeal cancer, or an oropharyngeal cancer; stomach cancers such as a gastric stromal tumor or a carcinoid tumor; testicular cancers such as a germ cell tumor, which includes a seminoma and a nonseminoma, and gonadal stromal tumor, which includes a Leydig cell tumor and a Sertoli cell tumor; thymus cancers such as to a thymoma, a thymic carcinoma, or a rectal cancer; and colon cancer.

Combination Therapy

In some embodiments, the compound provided herein is administered in combination with one or more other therapies. For example, provided herein are methods for combination therapies in which an agent known to modulate other pathways, or other components of the same pathway, or even overlapping sets of target enzymes are used in combination with a compound provided herein, or a pharmaceutically acceptable form (e.g., pharmaceutically acceptable salts, hydrates, solvates, isomers, prodrugs, and isotopically labeled derivatives) thereof. In one aspect, such therapy includes, but is not limited to, the combination of the subject compound with chemotherapeutic agents, therapeutic antibodies, and/or radiation treatment, to provide a synergistic or additive therapeutic effect.

By "in combination with," it is not intended to imply that the other therapeutic agent must be administered concurrently and/or formulated for delivery together, although these methods of delivery are within the scope of this disclosure. A compound as provided herein can be administered concurrently with, prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before), or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after), one or more other therapies using one or more other additional agents. In general, each chemotherapeutic agent will be administered at a dose and/or on a time schedule determined for that particular agent. The other chemotherapeutic agent can be administered with the compound provided herein in a single composition or separately in a different composition.

In general, it is expected that additional chemotherapeutic agents employed in combination be utilized at levels that do not exceed the levels at which they are utilized individually. In some embodiments, the levels utilized in combination will be lower than those utilized individually.

In another aspect, provided herein is a pharmaceutical composition for inhibiting abnormal cell growth in a subject, comprising an effective amount of a compound of Formula (I) or a pharmaceutically acceptable form (e.g., a salt, a solvate, a hydrate, a salt of a solvate or a hydrate) thereof, in combination with an amount of an anti-cancer agent (e.g., a chemotherapeutic agent). Many chemical and biologic therapeutics are known in the art, and they can be used in combination with a compound as provided herein.

In some embodiments, one or more other chemotherapeutic agents (e.g., a second agent) may be selected from among the following: antibodies, DNA alkylating and/or intercalating agents, other nonspecific or sequence specific DNA binding agents, nucleoside analogs, platinum compounds, antiandrogens, antiestrogens, other antihormones, antimetabolites, angiogenesis inhibitors, mitotic inhibitors, cell cycle inhibitors, growth factor inhibitors, histone deacetylase inhibitors, kinase inhibitors, poly(ADP-ribose) polymerase inhibitors, proteasome inhibitors, topoisomerase inhibitors, and other enzyme inhibitors.

Nonlimiting examples of other chemotherapeutic agents include alkyl sulfonates (e.g., busulfan, improsulfan, piposulfan); anthracyclines (e.g., anthracenedione, bisantrene, doxorubicin, idarubicin, epirubicin, mitoxantrone, pirarubicin, zorubicin); antiadrenals (e.g., aminoglutethimide, mitotane, trilostane); antibiotics (e.g., aclarubicin, actinomycin, authramycin, azaserine, becatecarin, bleomycin, cactinomycin, calicheamicin, caminomycin, carabicin, carzinophilin, chromomycin, dactinomycin, detorubicin, diazooxonorleucine, esorubicin, esperamicin, marcellomycin, mitomycin, nogalamycin, olivomycin, peplomycin, pixantrone, plicamycin, porfiromycin, potfiromycin, puromycin, quelamycin, rebeccamycin, rodorubicin, streptonigrin, streptozocin, tubercidin, zorubicin); antiestrogens (e.g., acolbifene, afimoxifene, anastrozole, clomifene, epitiostanol, megestrol, mepitiostane, onapristone, tamoxifen, telapristone, toremifene); antifolates (e.g., aminopterin, denopterin, edatrexate, methotrexate, pemetrexed, pralatrexate, pteropterin, ratitrexed, trimetrexate); antiandrogens (e.g., apalutamide, bicalutamide, darolutamide, enzalutamide, flutamide, nilutamide); LHRH agonists (e.g., buserelin, goserelin, leuprolide, triptorelin); aziridines (e.g., benzodopa, carboquone, meturedopa, uredopa); BTK inhibitors (e.g., ibrutinib, ARQ 531, BGB-3111, CC-292, CT-1530, DTRMWXHS-12, GDC-0853, M7583, SNS-062); epipodophyllins (e.g., aminocamptothecin, belotecan, camptothecin, etoposide, exatecan, irinotecan, lurtotecan, rubitecan, teniposide, topotecan); HDAC inhibitors (e.g., abrexinostat, belinostat, entinostat, gavinostat, kevetrin, mocetinostat, panobinostat, pracinostat, quisinostat, resminostat, ricolinostat, romidepsin, panobinostat, valproic acid, vorinostat, 4SC-202, ACY-241, AR-42, CG200745, CHR-2845, CHR-3996, CUDC-101, CXD101, MPT0E028, OBP-801, SHP-141); JAK1/JAK2 or STAT inhibitors (e.g., baricitinib, fostamatinib, itacitinib, lestaurtinib, momelotinib, pacritinib, ruxolitinib phosphate, tofacitinib, AZD1480, BMS-911543, CYT387, GLPG0636, INCB047986, INCB16562, NS-018, TG101348, WP1066, XL019); tyrosine kinase inhibitors (e.g., abemaciclib, afatinib, amuvatinib, axitinib, bosutinib, cediranib, crizotinib, dasatinib, defactinib, dovitinib, erlotinib, gefitinib, ibrutinib, imatinib, lapatinib ditosylate, lestaurtinib, linifanib, neratinib, nilotinib, nintedanib, niraparib, olaparib, palbociclib, pazopanib, ponantinib, rebastinib, regorafenib, ribociclib, rucaparib, sorafenib, staurosporine, sunitinib, tivozanib, toceranib, vandetanib, vatalanib, BMS-777607, CEP-11981, JNJ-26483327, OSI-930, PCI-32765, PF-04217903, XL228); mTOR inhibitors (e.g., dactolisib, everolimus, rapamycin, ridaforolimus, sapanisertib, sirolimus, temsirolimus, AZD8055, BEZ235, BGT226, GDC0980, OSI-027, PF-4691502, SF1126, XL765); nitrogen mustards (e.g., atrimustine, cyclophosphamide, ifosfamide, estramustine, mafosfamide, mannomustine, melphalan, phenamet, phenesterine, thiophosphamide); nitrosoureas (e.g., carmustine, chlorozotocin, fotemustine, lomustine, nimustine, ranimustine, semustine); platinum compounds (e.g., carboplatin, cisplatin, nedaplatin, oxaliplatin, triplatin tetranitrate); purine analogs (e.g., fludarabine, mercaptopurine, thiamiprine, thioguanine); pyrimidine analogs (e.g., ancitabine, azacitidine, azauridine, capecitabine, carmofur, cytarabine, dideoxyuridine, doxifluridine, enocitabine, floxuridine, fludarabine, fluorouracil, gemcitabine, tegafur); taxanes (e.g., cabazitaxel, docetaxel, larotaxel, ortataxel, paclitaxel, tesetaxel); triazines (e.g., altretamine, dacarbazine, procarbazine, temozolomide, triethylenemelamine, trimethylol melamine); vinca alkaloids (e.g., vinblastine, vincristine, vindesine, vinflunine, vinorelbine, vinrosidine); amonafide, apaziquone, brostallicin, demecolcine, diaziquone, elliptinium, epothilone, eribulin, etoglucid, exisulind, ferruginol, lonidamine, mitobronitol, mitoguazone, mitolactol, mopidamol, nitracrine, pipobroman, podophyllinic acid, sizofiran, tenuazonic acid, trabectedin, and vadimezan.

Exemplary biologics include, but are not limited to, cytokines (e.g., tumor necrosis factor alpha), interferons (e.g., an alpha interferon, beta interferon, gamma interferon), hematopoietic growth factors (e.g., erythropoietin, GM-CSF, G-CSF, IL-11), interleukins (e.g., IL-2, IL-4, IL-7, IL-9, IL-12, IL-15, IL-18, IL-21), and antibodies (e.g., abagovomab mimics CA125 tumor antigen to induce immune response, adecatumumab binds EpCAM to trigger immune response, atezolizumab binds PD-L1, avelumab binds PD-L1, anti-VEGF bevacizumab inhibits angiogenesis, cetuximab inhibits EGFR activity, anti-GD2 dinutuximab to trigger immune response, durvalumab binds PD-L1, ipilimumab binds CTLA4, nivolumab binds PD-1, oregovomab binds CA125 tumor antigen to induce immune response, panitumumab inhibits EGFR activity, pembrolizumab binds PD-1, pertuzumab binds HER2, anti-VEGFR2 ramucirumab inhibits angiogenesis, anti-VEGF ranibizumab inhibits angiogenesis, seribantumab inhibits HER3 activity, trastuzumab inhibits HER2 activity, tremelimumab binds CTLA4), cancer vaccines, CAR T cells or tumor infiltrating lymphocytes (TIL), and other cellular treatments.

Additional chemotherapeutic agents, biologics (e.g., antibodies and specific enzyme inhibitors) or small chemical compounds, that can be combined with a compound of the present invention are described and their utility for one or more types of cancer can be found in Bragalone's *Drug Information Handbook for Oncology*, Chu's *Physicians' Cancer Chemotherapy Drug Manual*, Goodman and Gilman's *The Pharmacological Basis of Therapeutics*, and Polovich's *Chemotherapy and Biotherapy Guidelines and Recommendations for Practice*, all of which are incorporated herein by reference in their entirety.

In some embodiments, a process is provided herein for using a compound of Formula (I) or a pharmaceutically acceptable form (e.g., a salt, a solvate, a hydrate, a salt of a solvate or a hydrate) thereof, or a pharmaceutical composition as provided herein in combination with radiation in inhibiting abnormal cell growth or treating cancer in a subject. Protocols for radiation treatment are known (e.g., brachytherapy or external beam therapy), and any one of them can be used as part of combination therapy as provided herein. In combination therapy, a pharmaceutical composition as provided herein can be administered before, during, and/or after radiation treatment.

For therapy of an ovarian cancer or tumor, a compound of Formula (I), or a pharmaceutically acceptable form thereof (e.g., a salt, a solvate, a hydrate, a salt of a solvate or hydrate), or a pharmaceutical composition as provided herein can be combined with another treatment. A standard therapy is surgical removal of the tumor, surgical debulking, or palliative surgery followed by chemotherapy (e.g., carboplatin with paclitaxel, or gemcitabine with cisplatin). Cisplatin may be used instead of carboplatin; docetaxel may be used instead of paclitaxel. A compound as provided herein may be administered before surgical debulking, or during and after chemotherapy. Because de-ethylflavopereirine appears to be nontoxic and is capable of systemic effects when taken orally, enteral administration by the patient of a tablet or capsule once or twice daily is preferred. Alternatively, a compound as provided herein can be infused (intravenously or intraperitoneally) or injected (subcutaneously or intramuscularly). Optionally, an antibody (e.g., bevacizumab, pembrolizumab) and/or a small molecule (e.g., niraparib, olaparib, rucaparib) inhibitor may also be administered over several treatment cycles, with or without a single round of vaccine/immune cell therapy eliciting an immune response against one or more antigens derived from the patient's tumor. Optionally, altretamine, cyclophosphamide, doxorubicin, epirubicin, etoposide, ifosfamide, melphalan, pemetrexed, tamoxifen, thiophosphamide, topotecan, or vinorelbine may also be administered during chemotherapy for ovarian cancer.

For therapy of a pancreatic cancer or tumor, a compound of Formula (I), or a pharmaceutically acceptable form thereof (e.g., a salt, a solvate, a hydrate, a salt of a solvate or hydrate), or a pharmaceutical composition as provided herein can be combined with another treatment. A standard therapy for stage I and stage II pancreatic cancer is surgical removal of the tumor (which may involve other organs of the gastrointestinal tract beside the whole pancreas or a part thereof), followed by chemotherapy with or without radiation treatment. For stage III and stage IV pancreatic cancer, palliative surgery at most is performed. Chemotherapy protocols include, but are not limited to: leucovorin, fluorouracil, irinotecan, and oxaliplatin (FOLFIRINOX); gemcitabine with cisplatin or oxaliplatin; leucovorin, fluorouracil, and oxaliplatin (OFF regimen). A compound as provided herein may be administered during chemoradiation or chemotherapy. Because de-ethylflavopereirine appears to be nontoxic and is capable of systemic effects when taken orally, enteral administration by the patient of a tablet or capsule once or twice daily is preferred. Alternatively, a compound as provided herein can be injected (subcutaneously or intramuscularly) or infused (intravenously or intraabdominally). Optionally, an antibody (e.g., bevacizumab, ipilimumab, nivolumab, pembrolizumab, tremelimumab) and/or a small molecule (e.g., cediranib, erlotinib, everolimus, olaparib, pazopanib, sunitinib, temsirolimus) inhibitor may also be administered over several treatment cycles, with or without a single round of vaccine/immune cell therapy eliciting an immune response against one or more antigens derived from the patient's tumor. Optionally, capecitabine, mitcomycin C, paclitaxel, or streptozocin may also be administered during chemotherapy or chemoradiation for pancreatic cancer.

For therapy of a brain cancer or tumor (glioblastoma), a compound of Formula (I), or a pharmaceutically acceptable form thereof (e.g., a salt, a solvate, a hydrate, a salt of a solvate or hydrate), or a pharmaceutical composition as provided herein can be combined with another treatment. A standard therapy is surgical removal of the tumor, followed by radiation treatment and temozolomide. A compound as provided herein may be started after surgery, then continued during radiation and chemotherapy. Chemotherapy protocols include, but are not limited to: lomustine, procarbazine, and vincristine (PCV). Because de-ethylflavopereirine appears to be nontoxic and is capable of systemic effects when taken orally, enteral administration by the patient of a tablet or capsule once or twice daily is preferred. Alternatively, a compound as provided herein can be injected (subcutaneously or intramuscularly) or infused (intravenously or intrathecally). Optionally, after radiotherapy, an antibody (e.g., bevacizumab, pembrolizumab) and/or a small molecule (e.g., everolimus) inhibitor may be administered with temozolomide over several treatment cycles, with or without a single round of vaccine/immune cell therapy eliciting an immune response against one or more antigens derived from the patient's tumor. Optionally, carmustine may also be administered during chemotherapy for brain cancer.

For therapy of a breast cancer or tumor, a compound of Formula (I), or a pharmaceutically acceptable form thereof (e.g., a salt, a solvate, a hydrate, a salt of a solvate or hydrate), or a pharmaceutical composition as provided herein can be combined with another treatment. A standard therapy is surgical removal of the tumor, followed by radiation treatment (external beam or brachytherapy), hormonal treatment (e.g., anastrozole, exemestane, fulvestrant, letrozole, tamoxifen, toremifene), and a cocktail of two or more chemotherapeutic agents (e.g., bevacizumab, carboplatin, cyclophosphamide, docetaxel or paclitaxel, daunorubicin or doxorubicin, epirubicin, fluorouracil, gemcitabine, methotrexate, neratinib, thiotepa, trastuzumab). A compound as provided herein may be started after surgery, then continued during radiation, hormonal treatment, and chemotherapy. Because de-ethylflavopereirine appears to be nontoxic and is capable of systemic effects when taken orally, enteral administration by the patient of a tablet or capsule once or twice daily is preferred. Alternatively, a compound as provided herein can be injected (subcutaneously or intramuscularly) or infused (intravenously or intraperitoneally). Optionally, abemaciclib, capecitabine, eribulin, everolimus, gemcitabine, ixabepilone, lapatinib, mitomycin, mitoxantrone, palbociclib, pertuzumab, ribociclib, vincristine, or vinorelbine may also be administered alone or in combination during chemotherapy for advanced or metastatic breast cancer.

For therapy of a colorectal cancer or tumor, a compound of Formula (I), or a pharmaceutically acceptable form thereof (e.g., a salt, a solvate, a hydrate, a salt of a solvate or hydrate), or a pharmaceutical composition as provided herein can be combined with another treatment. A standard therapy is surgical removal of the tumor, followed by radiation treatment (external beam or brachytherapy) and a cocktail of two or more chemotherapeutic agents (e.g., bevacizumab, capecitabine, cetuximab, fluorouracil, irinotecan, leucovorin, oxaliplatin, panitumumab, ramucirumab, regorafenib). A compound as provided herein may be started at any time before, during or after surgery, then continued during radiation, chemotherapy, or chemoradiation. Because de-ethylflavopereirine appears to be nontoxic and is capable of systemic effects when taken orally, enteral administration by the patient of a tablet or capsule once or twice daily is preferred. Alternatively, a compound as provided herein can be injected (subcutaneously or intramuscularly) or infused (intravenously or intraperitoneally). Optionally, nivolumab, pembrolizumab, trifluridine/tipiracil may also be administered during chemotherapy or chemoradiation for colorectal cancer.

In combination therapy, the chemotherapeutic agents can be administered simultaneously, sequentially, or separately. For therapy of lung cancer or a tumor, a compound as provided herein, or a pharmaceutically acceptable form thereof (e.g., a salt, a solvate, a hydrate, a salt of a solvate or a hydrate), or a pharmaceutical composition as provided herein can be combined with one or more of bevacizumab, cisplatin or carboplatin, erlotinib, gemcitabine, and pemetrexed. For therapy of renal carcinoma or a tumor, a compound of Formula (I), or a pharmaceutically acceptable form thereof (e.g., a salt, a solvate, a hydrate, a salt of a solvate or hydrate), or a pharmaceutical composition as provided herein can be combined with bevacizumab and/or sorafenib. For therapy of endometrial cancer or a tumor, a compound as provided herein, or a pharmaceutically acceptable form thereof (e.g., a salt, a solvate, a hydrate, a salt of a solvate or a hydrate), or a pharmaceutical composition as provided herein with can be combined with one or more of cisplatin or carboplatin, docetaxel, and doxorubicin. For therapy of breast cancer or a tumor, a compound as provided herein, or a pharmaceutically acceptable form thereof (e.g., a salt, a solvate, a hydrate, a salt of a solvate or a hydrate), or a pharmaceutical composition as provided herein can be combined with one or more of bevacizumab, capecitabine, erlotinib, everolimus, gemcitabine, lapatinib, letrozole, tamoxifen, a taxane, and trastuzumab. For therapy of prostate cancer or a tumor, a compound as provided herein, or a pharmaceutically acceptable form thereof (e.g., a salt, a solvate, a hydrate, a salt of a solvate or a hydrate), or a pharmaceutical composition as provided herein can be combined with one or more of bevacizumab, capecitabine, everolimus, gemcitabine, lapatinib, letrozole, tamoxifen, tarceva, a taxane, and trastuzumab.

The compounds described herein can be used in combination with the agents provided herein or other suitable agents, depending on the condition being treated. Hence, in some embodiments, the compounds as provided herein will be co-administered with other agents as described above. When used in combination therapy, the compounds described herein can be administered with the second agent simultaneously or separately. This administration in combination can include simultaneous administration of the two agents in the same unit dose, simultaneous administration in separate unit doses, and separate administration. That is, a compound described herein and any of the agents described above can be formulated together in the same unit dose and administered simultaneously. Alternatively, a compound as provided herein and any of the agents described above can be simultaneously administered, wherein both the agents are present in separate formulations. In another alternative, a compound as provided herein can be administered just followed by and any of the agents described above, or vice versa. In the separate administration protocol, a compound as provided herein and any of the agents described above can be administered a few minutes apart, or a few hours apart, or a few days apart.

A compound of Formula (I) can be administered by any method (e.g., enteral, parenteral, topical) that enables delivery of the compound to the site of action (e.g., locally or systemically). An effective amount of the compound can be administered in either single or multiple unit doses by any route including, without limitation: oral, buccal, sublingual, rectal, intranasal, transdermal, intravenous, intra-arterial, intramuscular, subcutaneous, intramuscular, or intraperitoneal.

EXAMPLES

Synthesis and Structure of De-Ethylflavopereirine

De-ethylflavopereirine was synthesized and its activity analyzed for two reasons. First, to simplify the structure of flavopereirine by removing the ethyl group thereby removing a possible source of chemical interaction. Second, to maintain the three dimensional form of the compound—both flavopereirine and de-ethylflavopereirine are planar—a property critical to the stacking interactions thought to occur with cancer cell DNA.

Figure 1:
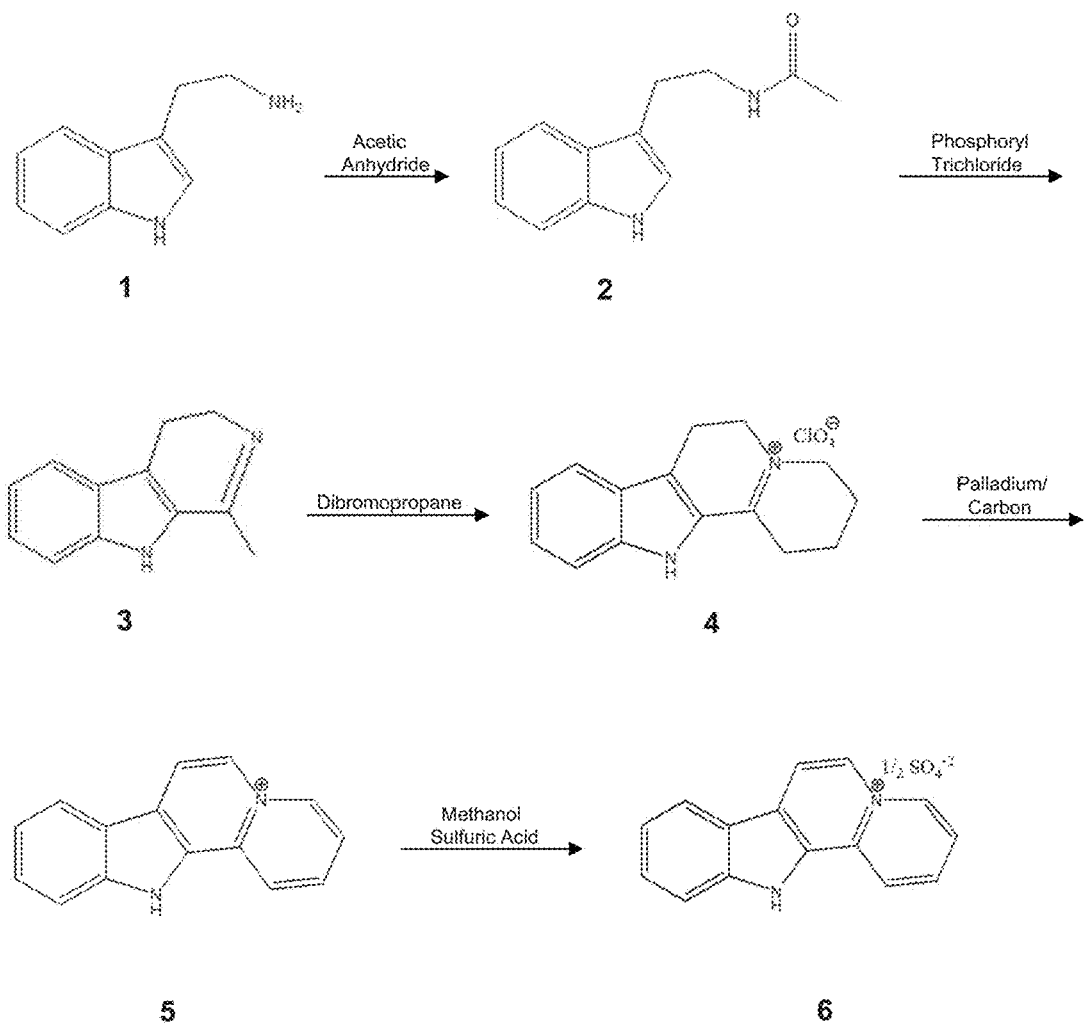
FIG. 1. Steps in the organic synthesis of de-ethylflavopereirine: amine group of tryptamine (1),2-(1H-indol-3-yl)-ethylamine, is acetylated with acetic anhydride to yield N-[2-(1H-indol-3-yl)-ethyl]-acetamide (2); subsequent cyclization mediated by phosphoryl chloride yields 1-methyl-4,9-dihydro-3H-b-carboline (3); a C—N coupling reaction with 1,2-dibromopropane bridge yields the D ring-containing compound 2,3,4,6,7,12-hexahydro-1H-indolo [2,3-a]quinolizin-5-ylium perchlorate salt (4); subsequent oxidation reactions with 10% Pd/C yield de-ethylflavopereirine (5), 12H-indolo[2,3-a]quinolizin-5-ylium; optionally, the sulfate salt 12H-indolo[2,3-a]quinolizin-5-ylium sulfate (6) is generated in methanol/sulfuric acid.
Figure 4:
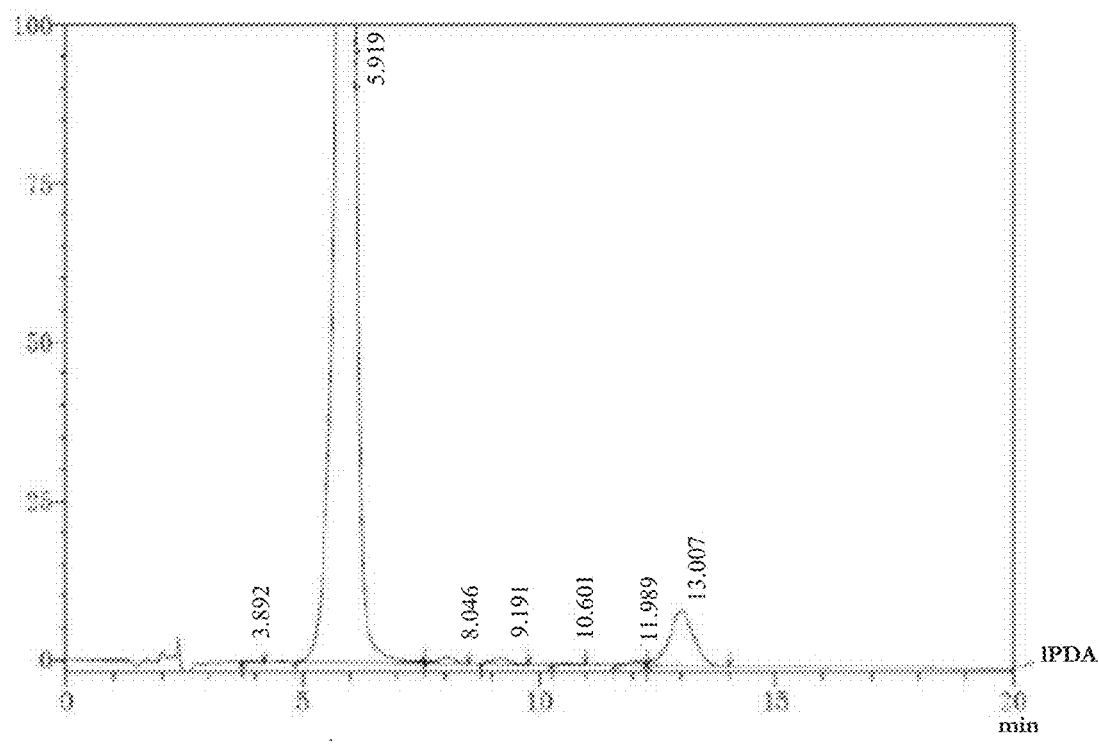
FIG. 4. High-performance liquid chromatography (HPLC) analysis of synthetic de-ethylflavopereirine. Here, the purity of the desired product was greater than 97%.
Figure 5:
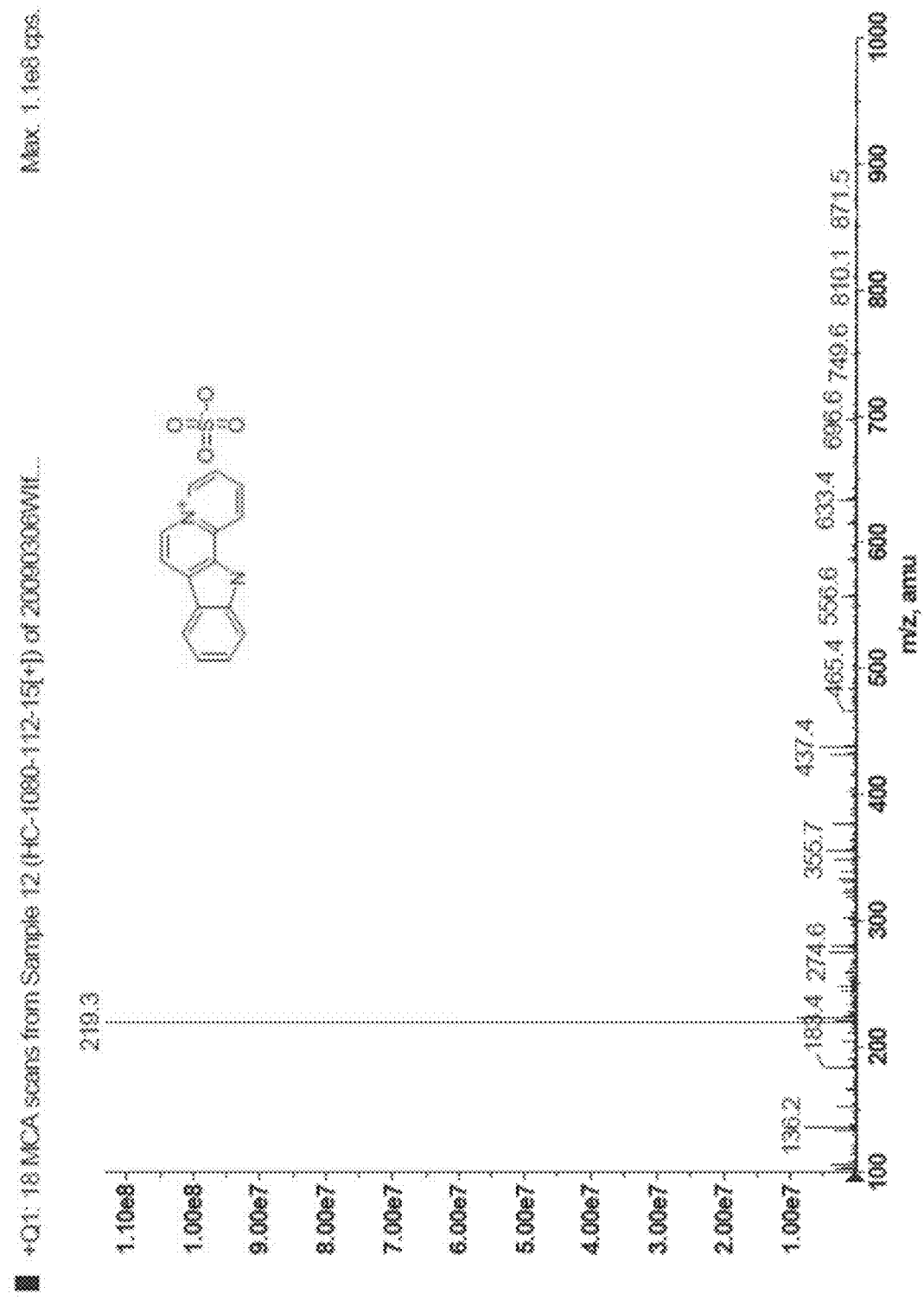
FIG. 5. Mass spectrometry (MS) analysis of synthetic de-ethylflavopereirine. The single prominent peak at m/z=219.3 corresponds to the desired product.

The chemical synthesis, molecular structure and purity of de-ethylflavopereirine are shown in FIGS. 1 to 5. The starting compound for synthesis is tryptamine and purity greater than 97% was obtained using the reaction scheme shown (FIG. 1). The sulfate salt of de-ethylflavopereine was chosen because it is stable and water soluble (FIG. 2). Structure and purity were confirmed by UV absorption spectrometry, high-performance liquid chromatography, and mass spectrometry (FIGS. 3 to 5).

Figure 6:
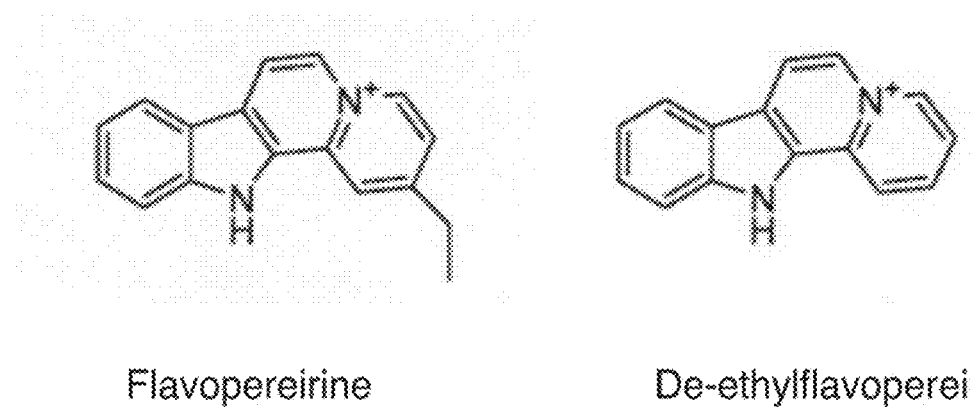
FIG. 6. Comparison of the chemical structures of de-ethylflavopereirine (right) and flavopereirine (left) having the ethyl substituent absent in de-ethylflavopereirine.

The chemical structures of de-ethylflavopereirine and flavopereirine are compared in FIG. 6. In de-ethylflavopereirine, the ethyl group ($-CH_2-CH_3$) present on the D ring of flavopereirine is absent.

De-Ethylflavopereirine Inhibits Cancer Cell Growth at Similar or Lower Concentrations Compared to Flavopereirine The primary goal of synthesizing de-ethylflavopereirine (compound 13-9-1) was to generate a different compound that still retains the anti-cancer cell activity of flavopereirine (compound 13-7-2). Comparison of the effects of the two compounds on proliferation of a variety of cancer cells confirmed that this goal was achieved. For example, the effect of de-ethylflavopereirine on two human breast cancer cell lines and two human prostate cancer cell lines were analyzed. In the case of the breast cancer cells the two compounds inhibit proliferation to the same extent at the same concentration (same IC50s). In the case of the prostate cancer lines, de-ethylflavopereirine was as active as flavopereirine at half the concentration indicating a somewhat more potent suppression of prostate cancer cell growth.

TABLE 1

| Assay | Compound Tested * | Cell Line | Growth Inhibition | Minimum Dose ** |
|---|---|---|---|---|
| Cell Proliferation (anti-cancer) | 13-7-2 | LnCap | Yes | $1 \times 10^{-5}$M |
| Cell Proliferation (anti-cancer) | 13-7-2 | RPWE-1 | Yes | $1 \times 10^{-5}$M |
| Cell Proliferation (anti-cancer) | 13-9-1 | LnCap | Yes | $5 \times 10^{-6}$M |
| Cell Proliferation (anti-cancer) | 13-9-1 | RPWE-1 | Yes | $5 \times 10^{-6}$M |

* Compound 13-9-1 is de-ethylflavopereirine and compound 13-7-2 is flavopereirine.
** Dose (IC50) needed to decrease growth 50% or greater versus control (culture medium alone with supplements) after any period of treatment.

De-Ethylflavopereirine is Significantly Less Toxic than Flavopereirine in Animals
1. Toxicity in Mice: Intraperitoneal Administration Toxicity studies showed that at all doses tested (100 mg/kg, 150 mg/kg, and 200 mg/kg), 50% of mice died after administration of flavopereirine by intraperitoneal (IP) injection. At the same doses, no mice injected IP with de-ethylflavopereirine died: a statistically significant result, P<0.05.

A study with synthetic compounds 13-7-2 (flavopereirine) and 13-9-1 (de-ethylflavopereirine) was conducted to compare the toxicity of the two compounds in animals. The compounds were dissolved in phosphate buffered saline for administration. Both compounds were injected IP in male immunodeficient (homozygous recessive scid/scid, beige/beige) mice. All mice were observed for potential adverse effects at time points of 15 min, 1 hr, 2 hr, 6 hr, 24 hr, and 48 hr after injection of the compound.

Compound 13-7-2 was injected at a dose of 100 mg/kg, 150 mg/kg, and 200 mg/kg in mice divided in groups of two. All mice injected with 150 mg/kg and 200 mg/kg dose exhibited lethargic behavior at 15 min after injection. One mouse injected with 150 mg/kg died at 6 hr whereas one mouse injected with 200 mg/kg dose died at 24 hr. One mouse injected with 100 mg/kg dose died at 48 hr. All mice injected with 150 and 200 mg/kg dose exhibited slowed heart rate, shallow respiration, and hypothermia from 6 hr to the time they were euthanized at 48 hr. The surviving mouse in the 100 mg/kg dose group had a swollen abdomen and was euthanized at 48 hr.

Compound 13-9-1 was injected at a dose of 100 mg/kg, 150 mg/kg, and 200 mg/kg in mice divided in groups of two. None of the mice injected with compound 13-9-1 died. Diarrhea was observed in all dose groups from 24 hr to 48 hr after injection except one mouse in the 150 mg/kg group which did not display this effect after 32 hr.

2. Toxicity in Mice: Oral Administration

De-ethylflavopereirine is well-tolerated in mice when given by oral administration: even at doses of 300 mg/kg. In contrast, flavopereirine is only tolerated at doses up to 100 mg/kg.

To estimate the maximum tolerated dose of compounds 13-7-2 and 13-9-1 in mice, both compounds were dissolved in PBS and given to SCID mice by oral gavage. All mice were observed for any adverse effects at 15 min, 1 hr, 2 hr, 6 hr, 24 hr, and 48 hr after administration of the compound or vehicle alone.

Compound 13-7-2 was administered at a dose of 100 mg/kg, 150 mg/kg, or 200 mg/kg. Each dose group consisted of three mice. In the 150 mg/kg treated group, two mice died 15 min after administration of the compound and one mouse died 48 hr after administration of the compound. The mouse that died at the 48 hr time point exhibited signs of distress, which included bradycardia, hypothermia, crusted shut eyes, and lethargy. In the 200 mg/kg treated group, two mice exhibited signs of distress which included rapid breathing, bradycardia, shut eyes, and lethargy. One mouse from this group died 24 hr after the administration of the compound. No signs of distress were observed in the 100 mg/kg group of mice with the exception of bradycardia 15 min after the administration of the compound in one mouse.

Compound 13-9-1 was administered at a dose of 100 mg/kg, 150 mg/kg, or 200 mg/kg by oral gavage (three mice per dose group). One mouse in the 200 mg/kg group died 15 min after the administration of the compound (apparently due to trauma caused by oral gavage). No signs of distress were observed in any of the other mice in the 100 mg/kg, 150 mg/kg, or 200 mg/kg treated groups.

In a separate dose finding/toxicity test with compound 13-9-1, three mice received escalating doses of 50 mg/kg/day for 3 days, 100 mg/kg/day for 7 days, 200 mg/kg/day for 7 days, and 300 mg/kg/day for 3 days, given by oral gavage. Mice were monitored closely for toxic signs. No abnormality was observed. At necropsy, no abnormality was found with peritoneal organs. These results indicated low toxic effect of oral 13-9-1 in mice.

3. Toxicity in Mice: Intravenous Administration

At 20 mg/kg and 40 mg/kg doses, intravenous administration of compound 13-9-1 in mice was well-tolerated. The 20 mg/kg dose provides sufficient serum concentration for the compound to exert its anti-tumor effect.

Anti-Cancer Activity of De-Ethylflavopereirine: Cell-Based Studies

De-ethylflavopereirine was tested for its activity against ovarian, pancreatic, brain, and colon cancer cell lines. The results are shown in FIGS. 7 to 10. In each case, the data demonstrate anti-cancer activity and also reveal additional details about the behavior of this anti-cancer agent. Cytotoxicity is assayed by reducing a yellow tetrazolium dye, 3-(4,5-dimethylthiazol-2-yl)-2,5-diphenyltetrazolium bromide (MTT), to insoluble purple formazan. The MTT assay is a colorimetric assay for determining the number of viable cells.

Figure 7:
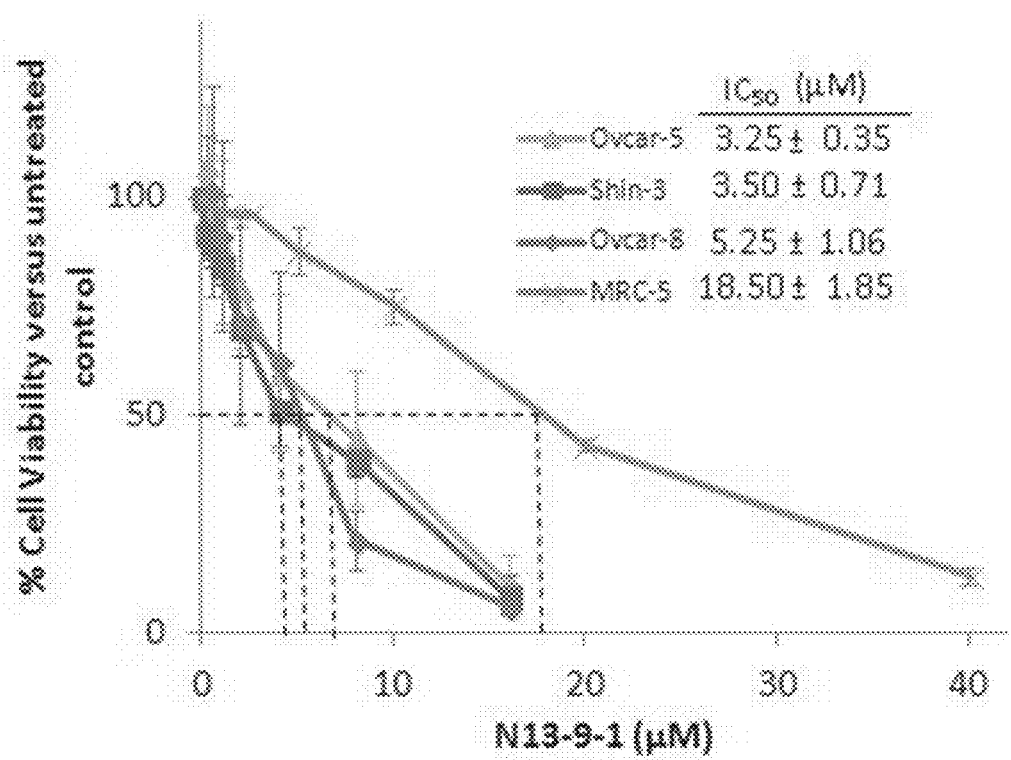

The results for ovarian cancer cell lines are shown in FIG. 7. The results for pancreatic cancer lines are shown in FIG. 8. There is a dose-dependent decrease in cancer cell viability as the concentration of de-ethylflavopereirine (compound 13-9-1) is increased. In contrast, the compound is significantly less toxic to the noncancerous epithelial cell line MRC-5. This is an important point: de-ethylflavopereirine selectively targets the ovarian and pancreatic cancer cells, but not normal cells.

FIG. 9 shows the effect of de-ethylflavopereirine (compound 13-9-1) on glioblastoma cell lines U-87MG, DBTRG-05, A172, and AM-38. Increasing compound 13-9-1 concentration yields a dose-dependent decrease in glioblastoma cell viability. The dose-response curves for the anti-brain cancer drug temozolomide are shown for comparison. For most of the glioblastoma cell lines the concentration at which 50% of the cells are killed (IC50) is 1.4- to 2.8-times higher for compound 13-9-1 than it is for temozolomide. The exception is AM38 for which the IC50 for compound 13-9-1 is lower than the IC50 for temozolomide (0.66 times). These dose-response curves show that, in a direct comparison, the activity of compound 13-9-1 against glioblastoma cell lines is similar to the well-known anti-brain cancer drug temozolomide.

The results for the colon cancer cell line HT-29 are shown in FIG. 10. A bioluminescent line was used enabling viability to be assessed by luminescence. In this case, the activity of compound 13-9-1 was compared with a Pao pereira extract containing flavopereirine and at least one other anti-cancer compound. As expected, the pure synthetic compound is active at much lower concentrations than the plant extract.

De-Ethylflavopereirine Induces Apoptosis in Cancer Cells

The results of flow cytometric analysis shown in FIG. 11 demonstrate that one mechanism of action that the synthetic compound 13-9-1 can use to kill cancer cells is by inducing apoptosis. The induction is dose dependent; the higher the concentration of the compound, the higher the percentage of pancreatic cancer cells undergoing apoptosis. Compared to the control consisting of untreated cells, the difference is statistically significant ($p<0.01$).

Induction of apoptosis was also shown by detection of Caspase-8, Caspase-3, and PARP cleavage products. The cleaved protein products are identified in FIG. 12 by arrows adjacent to the right panel. The accumulation of these proteolytic fragments is a biochemical signature for apoptotic cell death.

Induction of apoptosis is also the mechanism of action seen in ovarian and colon cancer cells.

De-Ethylflavopereirine Completely Inhibits Colony Formation of Pancreatic Cancer Cells Anchorage independent colony formation assay in soft agar was used to test long-term survival (20 days) of tumorigenic pancreatic cancer cells after exposure to de-ethylflavopereirine. PANC-1 cells formed colonies at the rate of 12% when untreated. De-ethylflavopereirine completely inhibited formation of PANC-1 colonies is soft agar. No tumorigenic cancer cells survived after exposure to compound 13-9-1 (FIG. 13).

Combining De-Ethylflavopereirine with Gemcitabine Leads to 100% Death of Pancreatic Cancer Cells that are Resistant to Gemcitabine One of the most powerful strategies for effective anti-cancer treatment is employing drug combinations. Because de-ethylflavopereirine can induce apoptosis of cancer cells by specifically targeting the damaged DNA structure of these cells, potentially synergistic combinations can be formed with the long list of anti-cancer drugs with a wide variety of mechanisms of action.

The dose-response curves shown in FIG. 14 show the results of combining de-ethylflavopereirine with gemcitabine, the drug in common use for pancreatic cancer. The curves for gemcitabine used alone show that all four of the pancreatic cancer cell lines are resistant to the drug. When combined with de-ethylflavopereirine drug resistance is effectively reversed and 100% of the cancer cells are killed. These data indicate a synergistic effect for the de-ethylflavopereirine/gemcitabine combination and provide a strong basis for further evaluation of de-ethylflavopereirine drug combinations.

In Vivo Studies: Pharmacokinetics

Administration of Compound 13-9-1 in Mice

Preliminary tests to establish optimal route of administration and dosing range in mice demonstrated IV administration was well-tolerated at 20 mg/kg and 40 mg/kg while oral administration was well-tolerated at 100 mg/kg, 200 mg/kg, and even 300 mg/kg (FIG. 15). Oral administration was chosen for the mouse experiments because administration is simplified by avoiding the need for tail vein injections.

Tissue Distribution of De-Ethylflavopereirine

After oral administration (200 mg·kg), compound 13-9-1 was found in all tested organs and tissues, including the brain. The highest concentrations (highest $C_{max}$) were found in kidney, colon and spleen. Highest AUC was found with the lung, followed by spleen, colon, and kidney.

Lung had the largest AUC and the fastest $T_{max}$. In the lung, $C_{max}$ was reached in 2 hours ($T_{max}=2$ hr), while in most of the other organs $T_{max}$ was 4 hours. Compound 13-9-1 was accumulated in the lung relatively fast, and was eliminated relatively slowly. The concentration was maintained in lung for a long time relative to other organs. At 24 hr, the concentration in the lung was still 6.67 nmoles/mg protein, 38% of the peak of 17.50 at 2 hr.

Colon had the second highest $C_{max}$ among all the organs tested, and an AUC only less than lung and spleen. The same fast distribution and slow elimination was seen in colon as in the lung. $T_{max}$ was 3 hr. At 24 hr, the concentration was 9.31 nmoles/mg protein, 29% of the peak of 31.63.

TABLE 2

| Organ | AUC (0-24 hr) | $C_{max}$ (nmoles/mg of protein) | $T_{max}$ (hr) |
| --- | --- | --- | --- |
| lung | 258.70 | 17.50 | 2 |
| spleen | 241.49 | 30.01 | 4 |
| colon | 194.72 | 31.63 | 3 |
| kidney | 185.07 | 55.69 | 4 |
| liver | 102.14 | 22.21 | 4 |
| adrenal gland | 74.80 | 17.62 | 4 |
| pancreas | 63.41 | 16.95 | 4 |
| heart | 53.21 | 7.82 | 4 |
| ovary | 42.48 | 11.17 | 4 |
| muscle | 19.54 | 5.67 | 4 |
| brain | 7.91 | 1.20 | 4 |

AUC = area under curve

Tissue distribution data showed that lung, spleen, colon, kidney, and liver had the best exposure to the compound. It is important to note that the levels attained in pancreas following 200 mg/kg provide a highly significant anti-cancer effect (see next section).

De-Ethylflavopereirine Suppresses PANC-1 Tumor Growth In Vivo

Mouse models for testing the activity of anti-cancer compounds have proven to be extremely powerful and provide an excellent basis for predicting the effectiveness of the compounds in human cancer patients. This is especially true when the xenografts of human cancer cells are transplanted orthotopically—meaning that the tumors grow in the organ they are associated with and the physiological environment mimics the clinical condition in humans.

Human PANC-1 pancreatic cancer cells were transfected with the luciferase gene to enable imaging in vivo. These cells were transplanted into the pancreas of nude mice and, after 10 days, tumors were established in the mice and they were treated with de-ethylflavopereirine by oral gavage. Longitudinal tumor progress was followed by live-animal imaging. The results of this experiment are depicted in FIGS. 16 to 21.

FIG. 16 shows the anti-tumor effect of de-ethylflavopereirine was significant by quantification of all images in the animals treated with the de-ethylflavopereirine compared to all images from the untreated control group. FIGS. 17 and 18 show representative images at the conclusion of the trial for untreated mice compared to mice treated with de-ethylflavopereirine.

FIG. 19 shows longitudinal images of two mice (2/9 or 22%) whose tumors were completely abolished by treatment with de-ethylflavopereirine. For other mice, tumor sizes were significantly reduced in the treated as compared to the untreated control group. FIG. 20A compares final tumor weights for treated or untreated animals to confirm the statistically significant reduction caused by de-ethylflavopereirine. FIG. 20B shows that metastatic lesions were also reduced by de-ethylflavopereirine.

The absence of toxic effect of de-ethylflavopereirine is indicated in FIG. 21. The body weights of mice in the treated group were indistinguishable from the body weights of mice in the untreated control group. Both groups showed normal weight gain over the course of the trial. Examination of the internal organs of the two groups also failed to reveal any toxic effects.

De-Ethylflavopereirine is Active Against Pancreatic Cancer Stem Cells

Cancer patients treated by radiation and chemotherapy often enter a remission following treatment. Remission may last months or years, but it is common for the cancer to return, metastasize, and eventually become more aggressive despite continued treatment. Cancer stem cells provide the basis for chemoresistance, radioresistance, and recurrence. A subset of tumor cells, cancer stem cells, are able to resist the destructive effects of anti-cancer treatments, persist over time, and then enable tumor regrowth. An agent with demonstrated anti-cancer stem cell activity would be helpful in developing new and successful cancer therapies.

Several experiments were performed showing the activity of de-ethylflavopereirine against pancreatic cancer stem cells.

In vitro, cancer stem cells form spheroids: clusters of cancer cells surrounding a cancer stem cell. Inhibition of spheroid formation is a test for anti-cancer stem cell activity of a compound. De-ethylflavopereirine showed potent anti-pancreatic cancer stem cell activity (FIGS. 22 and 23). The compound significantly inhibited primary spheroid formation at 5 µM and 10 µM concentrations. Secondary spheroids were completely inhibited at 5 µM and 10 µM, while 2.5 µM showed significant inhibition.

Cancer stem cells can be identified by specific cell-surface markers. A combination of three markers CD24, CD44, and EpCam is used for detection of pancreatic cancer stem cells. These markers can be labeled by different fluorophores and detected simultaneously by flow cytometry. Triple positive cells (i.e., cells that express all three markers) are regarded as pancreatic cancer stem cells. De-ethylflavopereirine reduced the percentage of pancreatic cancer stem cells in pancreatic cancer cell populations. PANC-1 cells were treated with 2.5 µM, 5.0 µM, and 10 µM concentrations of the compound for 24 hours or 48 hours. Triple positive cells were identified in quadrant Q2 ("Triple+") of the flow cytometry output. Reduction of the triple positive ($CD24^+$/$CD44^+$/$EpCam^+$) cancer stem cell population was seen at 24 hours (FIG. 24). At 48 hours, the reduction was statistically significant (FIG. 25).

In vivo, cancer stem cells are the primary source of tumor formation and growth. Thus, the rates of tumor formation and growth are indicators of cancer stem cell activity. When animals are inoculated with limited numbers of cancer cells, rates of tumor formation and growth can be accurately measured. It can then be determined whether a prospective agent slows the formation and growth rates of tumors, which is an indication of whether it acts against cancer stem cells. PANC-1 cancer cells were grown in suspension and pre-treated with de-ethylflavopereirine at 10 µM concentration before inoculation into mice. As a negative control, PANC-1 cancer cells were not pretreated with the compound. Following inoculation, the rates of tumor formation and growth were measured.

1) After $10^6$ PANC-1 cells were inoculated, tumors formed in 87% of the mice in the control group and 80% of the mice in the treated group. De-ethylflavopereirine significantly inhibited the growth of the PANC-1 tumors formed (FIG. 26A).
2) After $2 \times 10^5$ PANC-1 cells were inoculated, 80% of the mice formed tumors (control). De-ethylflavopereirine reduced tumor formation rate to 60%, indicating inhibition of pancreatic cancer stem cells. The single dose of de-ethylflavopereirine also slowed the growth rate of the tumors that formed (FIG. 26B).
3) After inoculation of $2 \times 10^4$ PANC-1 cells, 20% of mice formed tumors in both the control and the treated groups. Growth rates of the tumors in the two groups were not significantly different (FIG. 26C).

De-Ethylflavopereirine Suppresses PANC-1 Tumor Formation In Vivo: Anti-Cancer Stem Cell Activity FIG. 27 shows the effect of de-ethylflavopereirine on pancreatic tumor formation in mice following injection of PANC-1 cells that had been treated with the compound. Mice were then treated with de-ethylflavopereirine for 20 days after injection. After 20 days, tumor formation was observed in 55% of the animals injected with PANC-1 treated with compound 13-9-1 whereas tumor formation occurred in 100% of the animals in the control (untreated) group. Maximum tumor formation rate reached 80% at day 39, which is a highly significant difference compared to control (P=0.001 by log-rank test). This experiment demonstrates that de-ethylflavopereirine inhibits the defining activity of PANC-1 cancer stem cells: their ability to form new tumors.

De-Ethylflavopereirine Targets Wnt Signaling Pathway in Pancreatic Cancer Cells

Healthy stem cells normally represent a small population of the cells in an organ. They are specialized somatic cells, which are capable of self-renewal as well as differentiation so they regulate the growth and maintenance of tissues. Stem cells are controlled by a biochemical pathway called Wnt signaling.

Cancer stem cells have hijacked the normal stem cell control mechanism: the Wnt signaling pathway is aberrantly activated in cancer stem cells enabling initiation of tumors, persistence of cancers and metastases. The ability to safely target the Wnt signaling pathway offers enormous therapeutic promise for cancer.

Wnt pathway activation involves translocation of β-catenin from the cytoplasm into the nucleus and subsequent changes in transcription of targeted genes. Suppression of Wnt activation occurs when the translocation of β-catenin into the nucleus is suppressed. FIG. 28 shows that de-ethylflavopereirine suppresses Wnt activation by reducing the translocation of β-catenin from cytoplasm to nucleus. So de-ethylflavopereirine inhibits the growth of pancreatic cancer stem cells in part because it specifically suppresses Wnt signaling.

Anti-Inflammatory Effect of De-Ethylflavopereirine: Protection of Pancreatic Tissues from Chronic Inflammation Supports a Potential for Prevention of Pancreatic Cancer Chronic inflammation is a trigger for many types of cancer. Chronic inflammation of the pancreas, known as chronic pancreatitis, has been linked to a significantly higher risk of pancreatic cancer. For this reason, the anti-inflammatory activity of de-ethylflavopereirine was tested to see if it could suppress pancreatitis and therefore have the potential to prevent the transition from chronic inflammation to pancreatic cancer. The results were positive: de-ethylflavopereirine has a significant anti-inflammatory effect on pancreatitis, which justifies its use for the prevention of pancreatic cancer in patients with pancreatitis or other cancer risk factors.

Pancreatitis results from damage to exocrine, endocrine, and ductal cells of the pancreas. In humans, this condition is most often caused by excessive alcohol consumption. The tissue damage associated with pancreatitis is substantially augmented by the inflammatory response as infiltrating leukocytes cause further damage to pancreatic acinar cells. Such chronic inflammation contributes to pancreatic cancer in humans.

Alcohol-induced pancreatitis was studied in an animal model to test de-ethylflavopereirine for its potential to suppress the condition and to identify which inflammatory pathways are involved.

Daily administration of ethanol to mice was followed by a binge of ethanol administration, a regimen relevant to human consumption. In the experimental group, de-ethylflavopereirine was included in the daily diet throughout the course of the experiment. There were two control groups: animals that were given no alcohol (negative control) and animals given alcohol without receiving the compound 13-9-1 (positive control). Following 10 days of alcohol treatment, the animals were gavaged with alcohol for 8 hours then euthanized, and their pancreatic tissues were collected. Pancreatic tissue sections were analyzed for histology and isolated RNA was used for quantitative PCR.

Compared with healthy samples (FIG. 29A left panel) the pancreatic tissues from animals administered the alcohol regimen showed edema and infiltration of inflammatory cells (FIG. 29A center panel). The tissue damage seen in the pancreatic tissues from animals administered alcohol was prevented in animals that also received compound 13-9-1 (FIG. 29A right panel). The protective effect of de-ethylflavopereirine was also shown by the injury score that quantitates tissue damage. Treatment with de-ethylflavopereirine completely prevented injury, maintaining the healthy score seen in the tissues of animals that did not receive any alcohol (FIG. 29B).

De-ethylflavopereirine also lowered the infiltration of inflammatory cells in the pacreata of animals that received alcohol (FIG. 29C). Ly6G, a marker for neutrophils, is elevated four-fold in the pancreas of alcohol recipients; adding de-ethylflavopereirine as a therapeutic compound gives a completely normal Ly6G level meaning that the neutrophil counts in these alcohol-exposed tissues is normal.

The data demonstrate protection of the pancreas from the inflammatory effects of alcohol—the tissues are not injured by alcohol if de-ethylflavopereirine is present and the damage to the cells caused by alcohol-induced infiltration of neutrophils is prevented. Dethyl-flavopereirine affords tissue protection and direct anti-inflammatory action. De-ethylflavopereirine can reduce pancreatitis caused by alcohol consumption and therefore impede the progression of chronic pancreatitis to pancreatic cancer.

De-Ethylflavopereirine Suppresses HT-29 Colon Cancer Tumor Growth In Vivo

De-ethylflavopereirine reduced HT-29 tumor volumes in mice that received subcutaneous xenografts of these human colon cancer cells as shown in FIG. 30. In this example, the anti-tumor activity of de-ethylflavopereirine was compared with the activity of IFL (a combination of irinotecan, fluorouracil, and leucovorin). IFL has been routinely used in the treatment of colorectal cancer, but is associated with significant toxicity. The toxicity is so severe that some have encapsulated irinotecan in liposomes to reduce negative side effects.

IFL is more effective at reducing the HT-29 tumor volumes and functions more aggressively than de-ethylflavopereirine, but IFL was also severely toxic to the mice. De-ethylflavopereirine, while acting more slowly against the tumors, did not have toxic effects on the mice.

A comparison of the direct impact of de-ethylflavopereirine and IFL on tumors is depicted in FIGS. 32 and 33. Terminal deoxynucleotidyl transferase dUTP nick-end labeling (TUNEL) is a method for detecting DNA fragmentation by labeling the 3'-hydroxyl termini in the double-strand DNA breaks generated during apoptosis. Tumor sections from the two groups and an untreated control group were immunostained by the TUNEL method to specifically identify cells undergoing apoptosis. Tumor sections from untreated animals (FIG. 31) do not show TUNEL staining because apoptosis was not induced. Cells on the periphery of tumor sections from mice administered IFL showed more extensive damage; there are some cells that are TUNEL stained, cells on the periphery were destroyed. In FIG. 32, tumor sections from mice treated with de-ethylflavopereirine show that cells on the periphery were undergoing apoptosis induced by the compound.

REFERENCES

American Cancer Society. www.cancer.org
https://training.seer.cancer.gov/disease/cancer/
Abramovitch R. A., Shapiro D. "880. Tryptamines, carbolines, and related compounds. Part II. A convenient synthesis of tryptamines and β-carbolines" *J. Chem. Soc.* 4589-4592 (1956).
Beljanski M., Le Goff L., Beljsanski M. S. "Differential susceptibility of cancer and normal DNA templates allows the detection of carcinogens and anticancer drugs. Third NCI-EORTC Symposium on new drugs in cancer therapy" Institut Bordet, Brussels (1981).
Beljanski M., Bourgarel P., Beljanski M. S. "Correlation between in vitro DNA synthesis, DNA strand separation and in vivo multiplication of cancer cells" *Exp. Cell Biol.* 49:220-231 (1981).
Beljanski M., Beljanski M. S. "Selective inhibition of in vitro synthesis of cancer DNA by alkaloids of β-carboline class" *Exp. Cell Biol.* 50:79-87 (1982).
Beljanski M., Beljanski M. S. "Three alkaloids as selective destroyers of the proliferative capacity of cancer cells"*IRCS Med. Sci.* 12:587-588 (1984).
Beljanski M., Beljanski M. S. "Three alkaloids as selective destroyers of cancer cells in mice. Synergy with classic anticancer drugs" *Oncology* 43:198-203 (1986).
Beljanski M. "The anticancer agent pB-100, selectively active on malignant cells, inhibits multiplication of sixteen malignant cell lines, even multidrug resistant" *Genet. Mol. Biol.* 23:29-33 (2000).
Herve C. "Flavopereirine is an intercalating agent for non-supercoiled DNA" *Cancer Detect. Prev.* 22 (suppl. 1) (1998).
Denayer T., Stöhr T., Van Roy M. "Animal models in translational medicine: Validation and prediction" *New Horiz. Transl. Med.* 2:5-11 (2014).
Fürstner A., Ernst A. "Syntheses of camalexin, indolopyridocoline and flavopereirine" *Tetrahedron* 51:773-786 (1995).
Kraus G. A., Malpert J. H. "Synthesis of indolo[2,3-a] quinolizine alkaloids via nucleophilic additions of metallated pyridines" *Synlett* 107-108 (1997).
Malins D. C., Gunselman S. J. "Fourier-transform infrared spectroscopy and gas chromatography-mass spectrometry reveal a remarkable degree of structural damage in the DNA of wild fish exposed to toxic chemicals" *Proc. Nat'l Acad. Sci. USA* 91:13038-13041 (1994).
Malins D. C., Polissar N. L., Gunselman S. J. "Infrared spectral models demonstrate that exposure to environmental chemicals leads to new forms of DNA" *Proc. Nat'l Acad. Sci. USA* 94:3611-3615 (1997).
Malins D. C., Polissar N. L., Schaefer S., Su Y., Vinson M. "A unified theory of carcinogenesis based on order-disorder transitions in DNA structure as studied in the human ovary and breast" *Proc. Nat'l Acad. Sci. USA* 95:7637-7642 (1998).
Malins D. C., Polissar N. L., Gunselman S. J. "Tumor progression to the metastatic state involves structural modifications in DNA markedly different from those associated with primary tumor formation" *Proc. Nat'l Acad. Sci. USA* 93:14047-14052 (1996).
Malins D. C., Polissar, N. L., Gunselman, S. J. "Models of DNA structure achieve almost perfect discrimination between normal prostate, benign prostatic hyperplasia (BPH), and adenocarcinoma and have a high potential for predicting BPH and prostate cancer" *Proc. Nat'l Acad. Sci. USA* 94:259-264 (1997).
Malins D. C., Johnson P. M., Barker E. A., Polissar N. L., Wheeler T. M., Anderson K. M. "Cancer-related changes in prostate DNA as men age and early identification of metastasis in primary prostate tumors" *Proc. Nat'l Acad. Sci. USA* 100:5401-5406 (2003).

The invention claimed is:

1. A therapeutic method comprising administering a de-ethylflavopereirine compound in one or more doses to a subject afflicted with or at elevated risk for cancer; wherein the compound is de-ethylflavopereirine, a salt thereof, a solvate thereof, a hydrate thereof, or a salt of the solvate or the hydrate.

2. A method for treating a subject afflicted with cancer or chronic inflammation; the method comprising administering to the subject a pharmaceutical composition or a medical device; wherein the pharmaceutical composition or the medical device comprises a de-ethylflavopereirine compound selected from the group consisting of de-ethylflavopereirine, salts of de-ethylflavopereirine, solvates of de-ethylflavopereirine, salts of the solvates, hydrates of de-ethylflavopereirine, and salts of the hydrates.

3. A pharmaceutical composition or a medical device, including a kit of parts, manufactured by a process comprising incorporating at least one de-ethylflavopereirine compound selected from the group consisting of de-ethylflavopereirine, salts thereof, solvates thereof, hydrates thereof, salts of the solvates, and salts of the hydrates in the pharmaceutical composition or the medical device.

4. The method according to claim 2, wherein the pharmaceutical composition is administered systemically.

5. The method according to claim 2, wherein the pharmaceutical composition is administered locally.

6. The method according to claim 2, wherein the pharmaceutical composition is administered at least enterally.

7. The method according to claim 2, wherein the pharmaceutical composition is administered at least parenterally.

8. The method according to claim 2, wherein the pharmaceutical composition is formulated for at least topical application, inhalation, ophthalmic administration, or sublingual administration.

9. The method according to claim 2, wherein the medical device is implantable.

10. The method according to claim 2, further comprising administering an agent other than a de-ethylflavopereirine compound, wherein the agent is active in the treatment of cancer and is administered by the same or a different route as the de-ethylflavopereirine compound.

11. The method according to claim 1, wherein the cancer is characterized as at least one disease selected from the group consisting of carcinomas, sarcomas, melanomas, leukemias, and lymphomas.

12. The method according to claim 1, wherein the cancer is selected from the group consisting of lung, spleen, colon, kidney, liver, pancreatic, and ovarian cancers.

13. A method of treating inflammation and preventing resultant tissue damage comprising administering in one or more doses to a subject in need thereof a de-ethylflavopereirine compound selected from the group consisting of de-ethylflavopereirine, salts of de-ethylflavopereirine, solvates of de-ethylflavopereirine, salts of the solvates, hydrates of de-ethylflavopereirine, and salts of the hydrates in an amount effective to reduce inflammation and thereby prevent tissue damage by infiltrating leukocytes.

14. A therapeutic method comprising administering perorally an effective amount of a compound in solid form and packaged into one or more unit doses to a human patient afflicted with cancer to eliminate cells of a malignant tumor and/or metastasis; wherein the compound is selected from the group consisting of de-ethylflavopereirine, salts of de-ethylflavopereirine, solvates of de-ethylflavopereirine, salts of the solvates, hydrates of de-ethylflavopereirine, and salts of the hydrates.

15. The method according to claim 14, further comprising co-administering simultaneously or sequentially an effective amount of a chemotherapeutic agent other than the compound, wherein the chemotherapeutic agent is also active in the treatment of cancer.

16. The method according to claim 14, wherein the cancer cells eliminated include a cancer stem cell.

\* \* \* \* \*